(12) United States Patent
Usuda et al.

(10) Patent No.: US 7,060,475 B2
(45) Date of Patent: Jun. 13, 2006

(54) POLYNUCLEOTIDES ENCODING POLYPEPTIDES INVOLVED IN INTERMEDIATES METABOLISM OF CENTRAL METABOLIC PATHWAY IN METHYLOPHILUS METHYLOTROPHUS

(75) Inventors: Yoshihiro Usuda, Kawasaki (JP); Yousuke Nishio, Kawasaki (JP); Hisashi Yasueda, Kawasaki (JP); Shinichi Sugimoto, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 117 days.

(21) Appl. No.: 10/375,266

(22) Filed: Feb. 28, 2003

(65) Prior Publication Data

US 2004/0170987 A1    Sep. 2, 2004

(51) Int. Cl.
*C12N 9/04* (2006.01)
*C07K 1/00* (2006.01)

(52) U.S. Cl. .................. 435/190; 435/183; 435/252.3; 435/320.1; 530/350; 536/23.1; 536/23.2

(58) Field of Classification Search ............... 435/183, 435/190, 320.1, 6, 252.3; 536/23.1, 23.2
See application file for complete search history.

(56) References Cited

U.S. PATENT DOCUMENTS

| | | | |
|---|---|---|---|
| 2004/0091891 A1 | 5/2004 | Iomantas et al. | 435/6 |
| 2004/0170985 A1 | 9/2004 | Usuda et al. | 435/6 |
| 2004/0170986 A1 | 9/2004 | Usuda et al. | 435/6 |

FOREIGN PATENT DOCUMENTS

| | | |
|---|---|---|
| EP | 0035831 | 9/1981 |
| EP | 0037273 | 10/1981 |
| EP | 0066994 | 12/1982 |
| EP | 1188822 | 3/2002 |
| WO | WO 02/38777 | 5/2002 |

OTHER PUBLICATIONS

Ngo et al., Computational Complexity, Protein Structure Prediction, and the Levinthal Paradox, in The Protein Folding Problem and Tertiary Structure Prediction, 1994, Merz et al. (ed.), Birkhauser, Boston, MA, pp. 433 and 492-495.*
U.S. Appl. No. 09/926,299, filed Oct. 9, 2001, Gunji et al.

* cited by examiner

*Primary Examiner*—Richard Hutson
(74) *Attorney, Agent, or Firm*—Cermak & Kenealy, LLP; Shelly Guest Cermak

(57) ABSTRACT

The present invention provides polypeptides and polynucleotides involved in central intermediates metabolism in *Methylophilus methylotrophus* and methods of producing amino acids in microorganisms having enhanced or attenuated expression of these polypeptides and/or polynucleotides.

20 Claims, No Drawings

POLYNUCLEOTIDES ENCODING POLYPEPTIDES INVOLVED IN INTERMEDIATES METABOLISM OF CENTRAL METABOLIC PATHWAY IN METHYLOPHILUS METHYLOTROPHUS

BACKGROUND OF THE INVENTION

1. Field of the Invention

The present invention relates to novel polynucleotides encoding proteins involved in intermediates metabolism of central metabolic pathway, derived from microorganisms belonging to methylotrophic bacteria and fragments thereof, polypeptides encoded by the polynucleotides and fragments thereof, polynucleotide arrays comprising the polynucleotides and fragments thereof.

2. Discussion of the Background

Amino acids such as L-lysine, L-glutamic acid, L-threonine, L-leucine, L-isoleucine, L-valine and L-phenylalanine are industrially produced by fermentation by using microorganisms that belong to the genus *Brevibacterium, Corynebacterium, Bacillus, Escherichia, Streptomyces, Pseudomonas, Arthrobacter, Serratia, Penicillium, Candida* or the like. In order to improve the productivity of amino acids, strains of the aforementioned microorganisms that have been isolated from nature or artificial mutants thereof have been used. Various techniques have also been disclosed for enhancing activities of L-amino acid biosynthetic enzymes by using recombinant DNA techniques to increase the L-amino acid-producing ability.

L-amino acid production has been increased considerably by breeding of microorganisms such as those mentioned above and by improvements in production methods. However, in order to meet a future increase in the demand for L-amino acids, development of methods for more efficiently producing L-amino acids at lower cost are still desired.

Conventional methods for producing amino acids by fermentation using methanol, which is a raw fermentation material available in large quantities at a low cost, employ *Achromobacter* or *Pseudomonas* microorganisms (Japanese Patent Publication (Kokoku) No. 45-25273/1970), *Protaminobacter* microorganisms (Japanese Patent Application Laid-open (Kokai) No. 49-125590/1974), *Protaminobacter* or *Methanomonas* microorganisms (Japanese Patent Application Laid-open (Kokai) No. 50-25790/1975), *Microcyclus* microorganisms (Japanese Patent Application Laid-open (Kokai) No. 52-18886/1977), *Methylobacillus* microorganisms (Japanese Patent Application Laid-open (Kokai) No. 4-91793/1992), *Bacillus* microorganisms (Japanese Patent Application Laid-open (Kokai) No. 3-505284/1991) and others.

However, only a few methods have been described for producing L-amino acids using *Methylophilus* bacteria in conjunction with recombinant DNA technology. Although methods described in EP 0 035 831 A, EP 0 037 273 A and EP 0 066 994 A have been described as methods for transforming *Methylophilus* bacteria using recombinant DNA, applying recombinant DNA techniques to improvement of amino acid productivity of *Methylophilus* bacteria has not been described. Only WO 00/61723 and WO 02/38777 disclose the improved production of lysine and phenylalanine, respectively, using genes involved in each amino acid biosynthesis.

Therefore, prior to the present invention genes isolated from *Methylophilus* bacteria that are involved in intermediates metabolism of central metabolic pathway and which can be used to improve the yield of amino acids in cultured microorganisms remain elusive and undisclosed.

SUMMARY OF THE INVENTION

An object of the present invention is to provide novel measures for the improved production of amino acids or an amino acid, where these amino acids include asparagine, threonine, serine, glutamate, glycine, alanine, cysteine, valine, methionine, isoleucine, leucine, tyrosine, phenylalanine, histidine, lysine, tryptophan, arginine and the salts thereof. In a preferred embodiment the amino acids are L-amino acids.

Such a process includes bacteria, which express a protein comprising an amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42.

In one embodiment the polypeptides are encoded by a polynucleotide selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41. In another embodiment the polypeptides are encoded by other polynucleotides which have substantial identity to the herein described polynucleotides or those which hybridize under stringent conditions.

Another object of the invention is to provide polynucleotide sequences selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41; as well as those polynucleotides that have substantial identity to these nucleotide sequences, preferably at least 95% identity.

Another object of the invention is to provide isolated polypeptides having a sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42; as well as those polypeptides that have substantial identity to these amino acid sequences, preferably at least 95% identity.

A further object of the invention is a method for producing a protein or proteins by culturing host cells containing the herein described polynucleotides under conditions and for a time suitable for expression of the protein and collecting the protein produced thereby.

Another object is the use of host cells having the polynucleotides described herein to produce amino acids, as well as the use of such isolated polypeptides in the production of amino acids.

Other objects of the invention include methods of detecting nucleic acid sequences homologous to at least one of: SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, particularly nucleic acid sequences encoding polypeptides that herein described proteins or polypeptides and methods of making nucleic acids encoding such polypeptides.

The above objects highlight certain aspects of the invention. Additional objects, aspects and embodiments of the invention are found in the following detailed description of the invention.

DETAILED DESCRIPTION OF THE INVENTION

Unless otherwise defined, all technical and scientific terms used herein have the same meaning as commonly understood by one of ordinary skill in the art of molecular biology. Although methods and materials similar or equivalent to those described herein can be used in the practice or testing of the present invention, suitable methods and materials are described herein. All publications, patent applications, patents, and other references mentioned herein are incorporated by reference in their entirety. In addition, the materials, methods, and examples are illustrative only and are not intended to be limiting.

Reference is made to standard textbooks of molecular biology that contain definitions and methods and means for carrying out basic techniques, encompassed by the present invention. See, for example, Sambrook et al., Molecular Cloning: A Laboratory Manual, Third Edition, Cold Spring Harbor Laboratory Press, New York (2001), Current Protocols in Molecular Biology, Ausebel et al (eds.), John Wiley & Sons, New York (2001) and the various references cited therein.

*Methylophilus methylotrophus* (*M. methylotrophus*) is a gram negative ribulose monophosphate cycle methanol-utilizer, which can be used for the large-scale production of a variety of fine chemicals including amino acids, nucleic acids, vitamins, saccharides, and so on. The polynucleotides of this invention, therefore, can be used to identify microorganisms, which can be used to produce fine chemicals, for example, by fermentative processes. Modulation of the expression of the polynucleotides encoding enzymes which are involved in metabolism of central intermediates in central metabolic pathway of the present invention, can be used to modulate the production of one or more fine chemicals from a microorganism (e.g., to improve the yield of production of one or more fine chemicals from *Methylophilus* or *Methylbacillus* species).

The proteins encoded by the polynucleotides of the present invention are capable of, for example, performing a function involved in the metabolism of central intermediates in *M. methylotrophus*, such as fructose 6-phosphate, glucose 6-phosphate, 6-phosphoglucono-1,5-lactone, 6-phosphogluconate, 2-dehydro-3-deoxy-gluconate 6-phosphate, glyceraldehyde 3-phosphate, dihydroxyacetone phosphate, fructose 1,6-bisphosphate, erythrose 4-phosphate, sedoheptulose 7-phosphate, xylulose 5-phosphate, ribose 5-phosphate, ribulose 5-phosphate, glycerate-3-phosphate, glycerate-2-phosphate, or phosphoenolpyruvate.

Given the availability of cloning vectors used in *M. methylotrophus*, such as those disclosed in Methane and Methanol Utilizers, Plenum Press, New York (1992) edited by J. Colin Murrell and Howard Dalton, the nucleic acid molecules of the present invention may be used in the genetic engineering of this organism to make it better or more efficient producer of one or more fine chemicals.

There are a number of mechanisms by which the alteration of a protein of the present invention may affect the yield, production, and/or efficiency of production of a fine chemical from *M. methylotrophus* bacteria, which have the altered protein incorporated. Improving the ability of the cell to synthesize pyruvate (e.g., by manipulating the genes encoding enzymes involved in the conversion of 6-phosphogluconate into pyruvate), one may increase the yield or productivity of desired fine chemicals. Furthermore, by suppressing the activity of enzymes involved in the wasteful pathway such as the conversion of 6-phosphogluconate to ribulose 5-phosphate and carbon dioxide, one may also increase the yield or productivity of desired fine chemicals.

"L-amino acids" or "amino acids" as used herein means one or more amino acids, including their salts, preferably chosen from the following: L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine.

"Isolated" as used herein means separated out of its natural environment.

"Substantial identity" as used herein refers to polynucleotides and polypeptides which are at least 70%, preferably at least 80% and more preferably at least 90% to 95% identical to the polynucleotides and polypeptides, respectively, according to the present invention.

"Polynucleotide" as used herein relates to polyribonucleotides and polydeoxyribonucleotides, it being possible for these to be non-modified RNA or DNA or modified RNA or DNA.

"Polypeptides" as used herein are understood to mean peptides or proteins which comprise two or more amino acids bonded via peptide bonds. In particular, the term refers to polypeptides which are at least 70%, preferably at least 80% and more preferably at least 90% to 95% identical to the polypeptides according to the present invention. Included within the scope of the present invention are polypeptide fragments of the polypeptides having a sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42 or those which are identical to those described herein.

"Polynucleotides which encode the polypeptide" of the invention as used herein is understood to mean the sequences exemplified in this application as well as those sequences which have substantial identity to the nucleic acid sequences at least one of: SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41 and which encode a molecule having one or more of the bioactivities of the associated gene products. Preferably, such polynucleotides are those which are at least 70%, preferably at least 80% and more preferably at least 90% to 95% identical to the nucleic acid sequences at least one of: SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41.

Polynucleotides according to the invention may be employed as probes to isolate and/or identify RNA, cDNA and DNA molecules, e.g., full-length genes or polynucleotides which code for the polypeptides described herein. Likewise, the probes can be employed to isolate nucleic acids, polynucleotides or genes which have a high sequence similarity or identity with the polynucleotides of the invention.

Polynucleotides of the invention may also be used to design primers useful for the polymerase chain reaction to amplify, identify and/or isolate full-length DNA, RNA or other polynucleotides with high sequence homology or identity to the polynucleotides of the invention, as well as, polynucleotides that encode the polypeptides of the invention. Preferably, probes or primers are at least 15, 16, 17, 18, 19, 20, 21, 22, 23, 24, 25, 26, 27, 28, 29 or 30 nucleotides in length. Oligonucleotides with a length of at least 35, 40, 45, 50, 100, 150, 200, 250 or 300 nucleotides may also be used.

Methods of DNA sequencing are described inter alia by Sanger et al. (Proceedings of the National Academy of Sciences of the United States of America USA, 74:5463–5467, (1977)).

A person skilled in the art will find instructions for amplification of DNA sequences with the aid of the polymerase chain reaction (PCR) inter alia in the handbook by Gait: Oligonucleotide Synthesis: A Practical Approach (IRL Press, Oxford, UK, 1984) and in Newton and Graham: PCR $2^{nd}$ Edition (Springer Verlag, New York, 1997).

Additionally, methods employing DNA chips, microarrays or similar recombinant DNA technology that enables high throughput screening of DNA and polynucleotides that encode the herein described proteins or polynucleotides with high sequence homology or identity to the polynucleotides described herein. Such methods are known in the art and are described, for example, in Current Protocols in Molecular Biology, Ausebel et al (eds), John Wiley and Sons, Inc. New York (2000).

The polynucleotides and polypeptides of the present invention are involved in central intermediates metabolism in *M. methylotrophus*. By way of example, the present inventors provide the following cited references (each of which are incorporated herein by reference) demonstrating that assays to assess the enzymatic activity of the polypeptides of the present invention are known and, as such, determination of whether a sequence falls within the scope of the present claims may be readily ascertained. These polynucleotides and polypeptides include:

1. Glucose-6-phosphate isomerase enzyme comprises the amino acid sequence of SEQ ID NO:2 and is encoded by the pgi gene which comprises the polynucleotide SEQ ID NO:1 (Schreyer, R. and Bock, A., Arch. Microbiol. (1980) 127:289–298);
2. Glucose-6-phosphate 1-dehydrogenase enzyme comprises the amino acid sequence of SEQ ID NO:4 and is encoded by a zwf gene which comprises the polynucleotide SEQ ID NO:3 (Duffiieux, F. et al., J. Biol. Chem. (2000) 275: 27559–27565);
3. 6-phosphogluconolactonase enzyme comprises the amino acid sequence of SEQ ID NO:6 and is encoded by a pgl gene which comprises the polynucleotide SEQ ID NO:5 (Duffiieux, F. et al., J. Biol. Chem. (2000) 275: 27559–27565);
4. Phosphogluconate dehydratase enzyme comprises the amino acid sequence of SEQ ID NO:8 and is encoded by a edd gene which comprises the polynucleotide SEQ ID NO:7 (Egan, S. E. et. al. J. Bacteriol. (1992) 174:4638–46);
5. 2-keto-3-deoxy-6-phosphogluconate aldolase enzyme comprises the amino acid sequence of SEQ ID NO:10 and is encoded by a eda gene comprising SEQ ID NO:9 (Egan, S. E. et. al. J. Bacteriol. (1992) 174:4638–46);
6. Ribosephosphate isomerase enzyme comprises the amino acid sequence of SEQ ID NO:12 and is encoded by a rpi gene comprising SEQ ID NO:11 (Hove-Jensen, B. and Maigaard, M., J. Bacteriol. (1993) 175:5628–5635);
7. Ribulose-5-phosphate 3-epimerase enzyme comprises the amino acid sequence of SEQ ID NO:14 and is encoded by a rpe gene comprising SEQ ID NO:13 (Kiely, M. E. et. al., Biochim. Biophys. Acta (1973) 293:534–541);
8. Transketolase enzyme comprises the amino acid sequence of SEQ ID NO:16 and is encoded by a tkt gene comprising SEQ ID NO:15 (Sprenger, G. A. et. al. Eur. J. Biochem. (1995) 230:525–532);
9. Transaldolase enzyme comprises the amino acid sequence of SEQ ID NO:18 and is encoded by a tal gene comprising SEQ ID NO:17 (Sprenger, G. A. et. al. J. Bacteriol. (1995) 177:5930–5936);
10. Fructosebisphosphatase enzyme comprises the amino acid sequence of SEQ ID NO:20 and is encoded by a fbp gene comprising SEQ ID NO:19 (Kelley-Loughnane, N. et. al., Biochim. Biophys. Acta (2002) 1594:6–16);
11. Fructose-1,6-bisphosphate aldolase enzyme comprises the amino acid sequence of SEQ ID NO:22 and is encoded by a fba gene comprising SEQ ID NO:21 (Baldwin, S. A. et. al. Biochemical. J. (1978) 169:633–641);
12. Triose phosphate isomerase 1 enzyme comprises the amino acid sequences of SEQ ID NO:24 and is encoded by a tpi1 gene comprising SEQ ID NO:23 (Anderson, A. and Cooper, R. A., FEBS Lett. (1969) 4:19–20);
13. Triose phosphate isomerase 2 enzyme comprises the amino acid sequences of SEQ ID NO:26 and is encoded by a tpi2 gene comprising SEQ ID NO:25 (Anderson, A. and Cooper, R. A., FEBS Lett. (1969) 4:19–20);
14. Triose phosphate isomerase 3 enzyme comprises the amino acid sequences of SEQ ID NO:28 and is encoded by a tpi3 gene comprising SEQ ID NO:27 (Anderson, A. and Cooper, R. A., FEBS Lett. (1969) 4:19–200);
15. Glyceraldehyde-3-phosphate dehydrogenase 1 enzyme comprises the amino acid sequences of SEQ ID NO:30 and is encoded by a gap1 gene comprising SEQ ID NO:29 (Seta, F. D. et. al., J. Bacteriol. (1997) 179:5218–5221);
16. Glyceraldehyde-3-phosphate dehydrogenase 2 enzyme comprises the amino acid sequences of SEQ ID NO:32 and is encoded by a gap2 gene comprising SEQ ID NO:31 (Seta, F. D. et. al., J. Bacteriol. (1997) 179:5218–5221);
17. Phosphoglycerate kinase enzyme comprises the amino acid sequence of SEQ ID NO:34 and is encoded by a pgk gene comprising SEQ ID NO:33 (Bentahir, M. et. al., J. Biol. Chem. (2000) 275:11147–11153);
18. Phosphoglycerate mutase enzyme comprises the amino acid sequence of SEQ ID NO:36 and is encoded by a pgm gene comprising SEQ ID NO:35 (Fraser, H. I. et. al. FEBS Lett. (1999) 455:344–348);
19. Enolase enzyme comprises the amino acid sequence of SEQ ID NO:38 and is encoded by a eno gene comprising SEQ ID NO:37 (Spring, T. G. and Wold, F., Methods Enzymol. (1975) 42:323–329);
20. 6-phosphogluconate dehydrogenase 1 enzyme comprises the amino acid sequence of SEQ ID NO:40 and is encoded by a gnd1 gene comprising SEQ ID NO:39 (de Silva, A. O., Fraenkel, D. G., J. Biol. Chem. (1979) 254: 10237–10242);

21. 6-phosphogluconate dehydrogenase 2 enzyme comprises the amino acid sequence of SEQ ID NO:42 and is encoded by a gnd2 gene comprising SEQ ID NO:41 (de Silva, A. O., Fraenkel, D. G., J. Biol. Chem. (1979) 254: 10237–10242).

The terms "stringent conditions" or "stringent hybridization conditions" includes reference to conditions under which a polynucleotide will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing).

Typically, stringent conditions will be those in which the salt concentration is less than approximately 1.5 M Na ion, typically about 0.01 to 1.0 M Na ion (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions also may be achieved with the addition of destabilizing agents such as formamide. Exemplary low stringency conditions include hybridization with a buffer solution of 30 to 35% formamide, 1 M NaCl, 1% SDS (w/v; sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the Tm can be approximated from the equation of Meinkoth and Wahl (Anal. Biochem., 138:267–284, 1984): Tm=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The Tm is the temperature (under defined ionic strength and pH) at which 50% of a complementary target sequence hybridizes to a perfectly matched probe. Tm is reduced by about 1° C. for each 1% of mismatching; thus, Tm, hybridization and/or wash conditions can be adjusted to hybridize to sequences of the desired identity. For example, if sequences with approximately 90% identity are sought, the Tm can be decreased 10° C.

Generally, stringent conditions are selected to be about 5° C. lower than the thermal melting point (Tm) for the specific sequence and its complement at a defined ionic strength and pH. However, severely stringent conditions can utilize hybridization and/or wash at 1, 2, 3, or 4° C. lower than the thermal melting point (Tm); moderately stringent conditions can utilize a hybridization and/or wash at 6, 7, 8, 9, or 10° C. lower than the thermal melting point (Tm); low stringency conditions can utilize a hybridization and/or wash at 11, 12, 13, 14, 15, or 20° C. lower than the thermal melting point (Tm). Using the equation, hybridization and wash compositions, and desired Tm, those of ordinary skill will understand that variations in the stringency of hybridization and/or wash solutions are inherently described. If the desired degree of mismatching results in a Tm of less than 45° C. (aqueous solution) or 32° C. (formamide solution), it is preferred to increase the SSC concentration so that a higher temperature can be used. An extensive guide to the hybridization of nucleic acids is found in Tijssen, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, New York (1993); and Current Protocols in Molecular Biology, Chapter 2, Ausubel, et al., Eds., Greene Publishing and Wiley-Interscience, New York (1995).

Stringent hybridization conditions are understood to mean those conditions where hybridization, either in solution or on a solid support, occur between two polynucleotide molecules which are 70% to 100% homologous in nucleotide sequence which include 75%, 80%, 85%, 90%, 95%, 98% and all values and subranges therebetween.

Homology, sequence similarity or sequence identity of nucleotide or amino acid sequences may be determined conventionally by using known software or computer programs. To find the best segment of identity or similarity of sequences, BLAST (Altschul et al (1990) J. Mol. Biol. 215:403–410 and Lipman et al (1990) J. Mol. Biol. 215: 403–410), FASTA (Lipman et al (1985) Science 227:1435–1441), or Smith and Waterman (Smith and Waterman (1981) J. Mol. Biol. 147:195–197) homology search programs can be used. To perform global alignments, sequence alignment programs such as the CLUSTAL W (Thompson et al (1994) Nucleic Acids Research 22:4673–4680) can be used.

The present invention also provides processes for preparing amino acids using bacteria that comprise at least one polynucleotide whose expression is enhanced or attenuated. Likewise, the invention also provides processes for preparing amino acids using bacteria that comprise at least on polypeptide whose activity is enhanced or attenuated. Preferably, a bacterial cell with enhanced or attenuated expression of one or more of the polypeptides and/or polynucleotides described herein will improve amino acid yield at least 1% compared to a bacterial strain not having the enhanced or attenuated expression. For the production of amino acids the *M. methylotrophus* polynucleotides described herein may be used to target expression, either by disruption to turn off or increase or enhance the expression or relative activity of the polypeptide enzymes encoded therein.

The term "enhancement" as used herein means increasing intracellular activity of one or more polypeptides in the bacterial cell, which in turn are encoded by the corresponding polynucleotides described herein. To facilitate such an increase, the copy number of the genes corresponding to the polynucleotides described herein may be increased. Alternatively, a strong and/or inducible promoter may be used to direct the expression of the polynucleotide, the polynucleotide being expressed either as a transient expression vehicle or homologously or heterologously incorporated into the bacterial genome. In another embodiment, the promoter, regulatory region and/or the ribosome binding site upstream of the gene can be altered to achieve the over-expression. The expression may also be enhanced by increasing the relative half-life of the messenger RNA.

In another embodiment, the enzymatic activity of the polypeptide itself may be increased by employing one or more mutations in the polypeptide amino acid sequence, which increases the activity. For example, altering the relative Km of the polypeptide with its corresponding substrate will result in enhanced activity. Likewise, the relative half-life of the polypeptide may be increased.

In either scenario, that being enhanced gene expression or enhanced enzymatic activity, the enhancement may be achieved by altering the composition of the cell culture media and/or methods used for culturing.

"Enhanced expression" or "enhanced activity" as used herein means an increase of at least 10%, 25%, 50%, 75%, 100%, 150%, 200%, 300%, 400% or 500% compared to a wild-type protein, polynucleotide, gene; or the activity and/or the concentration of the protein present before the polynucleotides or polypeptides are enhanced.

The term "attenuation" as used herein means a reduction or elimination of the intracellular activity of the polypeptides in a bacterial cell that are encoded by the corresponding polynucleotide. To facilitate such a reduction or elimination, the copy number of the genes corresponding to the polynucleotides described herein may be decreased or removed. Alternatively, a weak and/or inducible promoter may used to direct the expression of the polynucleotide, the polynucleotide being expressed either as a transient expression vehicle or homologously or heterologously incorporated into the bacterial genome. For example, the endogenous promoter or regulatory region of the gene corresponding to the isolated polynucleotides described herein may be replaced with the aforementioned weak and/or inducible promoter. Alternatively, the promoter or regulatory region may be removed. The expression may also be attenuated by decreasing the relative half-life of the messenger RNA.

In another embodiment, the enzymatic activity of the polypeptide itself may be decreased or deleted by employing one or more mutations in the polypeptide amino acid sequence, which decreases the activity or removes any detectable activity. For example, altering the relative Kd of the polypeptide with its corresponding substrate will result in attenuated activity. Likewise, a decrease in the relative half-life of the polypeptide will result in attenuated activity.

By attenuation measures, the activity or concentration of the corresponding protein is in general reduced to 0 to 75%, 0 to 50%, 0 to 25%, 0 to 10% or 0 to 5% of the activity or concentration of the wild-type protein or of the activity or concentration of the protein in the starting microorganism.

Suitable vectors for carrying M. methylotrophus polynucleotides include those vectors which can direct expression of the gene in bacterial cells as known in the art. One embodiment of the present invention is whereby the vectors contain an inducible or otherwise regulated expression system whereby the M. methylotrophus polynucleotides may be expressed under certain conditions and not expressed under other conditions. Furthermore, in another embodiment of the invention, the M. methylotrophus polynucleotides can be constitutively expressed. Examples of such vectors and suitable cells in which they can be introduced are described in Sambrook et al., Molecular Cloning: A Laboratory Manual, 3rd Ed., Cold Spring Harbor Laboratory Press, Cold Spring Harbor, N.Y. (2001) and Current Protocols in Molecular Biology, Ausebel et al, (Eds.), John Wiley and Sons, Inc., New York, 2000.

Methods of introducing M. methylotrophus polynucleotides or vectors containing the M. methylotrophus polynucleotides include electroporation, conjugation, calcium-mediated transfection, infection with bacteriophage and other methods known in the art. These and other methods are described in Sambrook et al., Molecular Cloning: A Laboratory Manual, 3rd Ed., Cold Spring Harbor Laboratory Press, Cold Spring Harbor, N.Y. (2001) and Current Protocols in Molecular Biology, Ausebel et al, (Eds.), John Wiley and Sons, Inc., New York (2000).

The microorganisms that can be used in the present invention should have the ability to produce amino acids, preferably L-amino acids, from a suitable carbon source, preferably carbon sources such as methanol, glucose, sucrose, lactose, fructose, maltose, molasses, starch, cellulose glycerol or ethanol. The microorganisms can be Methylophilus bacteria, preferably Methylophilus methylotrophus.

Suitable culture conditions for the growth and/or production of M. methylotrophus polynucleotides are dependent on the cell type used. Likewise, culturing cells that contain attenuated or enhanced expression of the M. methylotrophus polynucleotides or polypeptides, as described herein, may be cultured in accordance with methods known in the art. Examples of culture conditions for various cells is described in Sambrook et al., Molecular Cloning: A Laboratory Manual, 3rd Ed., Cold Spring Harbor Laboratory Press, Cold Spring Harbor, N.Y. (2001); Current Protocols in Molecular Biology, Ausebel et al, (Eds.), John Wiley and Sons, Inc., 2000; and Cells: A Laboratory Manual (Vols. 1–3), Spector et al, (Eds.), Cold Spring Harbor Laboratory Press, Cold Spring Harbor, N.Y., (1988).

Following culturing the polypeptide or protein products, which are encoded by the M. methylotrophus polynucleotides, may be purified using known methods of protein purification. These methods include high performance liquid chromatography (HPLC), ion-exchange chromatography, size exclusion chromatography; affinity separations using materials such as beads with exposed heparin, metals, or lipids; or other approaches known to those skilled in the art. These and other methods of protein purification are disclosed in Sambrook et al., Molecular Cloning: A Laboratory Manual, 3rd Ed., Cold Spring Harbor Laboratory Press, Cold Spring Harbor, N.Y. (2001); Current Protocols in Molecular Biology, Ausebel et al, eds., John Wiley and Sons, Inc., 2000 and Protein Purification, Scopes and Cantor, (Eds.), Springer-Verlag, (1994). Likewise, the amino acids produced may be purified by methods known in the art using similar chromatography devices.

The invention also provides antibodies that bind to the polypeptides of the present invention. Antibodies binding to the polypeptides can be either monoclonal or polyclonal, preferably the antibodies are monoclonal. Methods for obtaining antibodies that bind to the polypeptides are known in the art and are described, for example, in Harlow and Lane, Antibodies: A Laboratory Manual, Cold Spring Harbor Laboratory Press, Cold Spring Harbor, N.Y. (1988).

Having generally described this invention, a further understanding can be obtained by reference to certain specific examples which are provided herein for purposes of illustration only, and are not intended to be limiting unless otherwise specified.

EXAMPLES

Whole genome sequencing using random shotgun method is described in Fleischman R. D. et. al. (1995) Science, 269: 496–512.

Example 1

Construction of Genomic Libraries of *Methylophilus methylotrophus*

*M. methylotrophus* AS1 was cultured at 30° C. in the 121 medium described in the Catalogue of Strains (The National Collections of Industrial and Marine Bacteria Ltd., 1994).

Cells were collected by centrifugation. Genomic DNA was isolated using the Genome-tip system (Qiagen K. K., Tokyo, Japan). The genomic DNA was sheared and fragmentized by sonication. The resultant fragments in the 1- to 2-kb size range were purified by gel electrophoresis through 1% low-melting agarose gel, followed by recovery using the Wizard DNA purification kit (Promega KK, Tokyo, Japan). The recovered fragments were ligated to the high-copy number vector pUC118 treated by HincII and bacterial alkaline phosphatase (Takara Shuzo, Kyoto, Japan), and this was designated pUC118 library.

For larger fragments (9- to 11-kb in size), the genomic DNA was partially digested by restriction endonuclease Sau3AI, followed by 0.6% agarose gel electrophoresis. The DNA fragments corresponding 9-kb to 11-kb in size were excised from gel and were recovered using the DNACELL (Daiichi Pure Chemicals, Tokyo, Japan). The recovered fragments were ligated into the low-coy number vector pMW118 (Nippon Gene, Toyama, Japan), which is a derivative of the pSC101 (Bernaidi, A. and Bernardi, F. (1984) Nucleic Acids Res. 12, 9415–9426). This library composed of large DNA fragments was designated pMW118 library.

General DNA manipulation was performed according to previously described methods (Sambrook et. al. (1989) "Molecular Cloning: A Laboratory Manual/Second Edition", Cold Spring Harbor Laboratory Press).

Example 2

DNA Sequencing and Sequence Assembly

The pUC118 library were transformed into *Escherichia coli* DH5α and plated on Luria-Bertani medium containing 100 μg/ml ampicillin and 40 μg/ml 5-bromo-4-chloro-3-indolyl-α-D-galactoside (X-Gal). The white colonies were picked up and cultured in Luria-Bertani medium containing 100 μg/ml ampicillin. The individual colony was cultured in the well of the 96 deep-well plates, and the plasmids were isolated using QIAprep Turbo Kit (Qiagen). The DNA fragments inserted into pUC118 were sequenced using a M13 reverse primer. The shotgun sequencing was performed with the BigDye terminators and 3700 DNA analyzer (Applied Biosystems Japan, Tokyo, Japan). Approximately 50,000 samples from pUC118 library corresponding to coverage of approximately 8-fold to the genome size were analyzed and the sequences were assembled by Phred/Phrap software (CodonCode, Mass., USA). This assembly treatment yielded 60 contigs with more than 5 kb in size.

As for pMW118 library, 2,000 clones corresponding to coverage of approximately 5-fold were sequenced using both M13 forward and reverse primers. The end-sequence data were analyzed and the linking clones between contigs were selected from pMW118 library. The inserted fragments of selected clones were amplified by the polymerase chain reaction (PCR) using LA Taq polymerase (Takara Shuzo) and *M. methylotrophus* genomic DNA as a template. These products of PCR were entirely sequenced as described in Example 1, and the gap DNA sequences between contigs were determined. By the additional sequence information, the Phrap assembly software reduced the number of contigs with more than 5 kb in size to 24. Then the 48 DNA primers with sequences complementary to the end-sequences of the 24 contigs were prepared. All possible pairwise combination of the primers were tested by PCR to amplify the DNA fragments of *M. methylotrophus* genomic DNA. The amplified products were sequenced directly. In several cases, the additional primers complementary to different sequences at the end of the contig were used. This strategy could close all of the remaining physical gaps and resulted in a single circular contig. Several regions that had been sequenced in only one direction and had postulated secondary structure were confirmed. By this research, the genome of *M. methylotrophus* was found to be a single circular with the size of 2,869,603 bases and GC content of 49.6%.

Example 3

Sequence Analysis and Annotation

Sequence analysis and annotation was managed using the Genome Gambler software (Sakiyama, T. et. al. (2000) Biosci. Biotechnol. Biochem. 64: 670–673). All open reading frames of more than 150 bp in length were extracted and the translated amino acid sequences were searched against non-redundant protein sequences in GenBank using the BLAST program (Altschul, S. F. et. al. (1990) J. Mol. Biol. 215, 403–410). Of putative polynucleotide encoding sequences with significant similarities to the sequences in public databases (BLASTP scores of more than 100), the genes involved in biosynthesis of amino acids were selected. Start codons (AUG or GUG) were putatively identified by similarity of the genes and their proximity to the ribosome binding sequences (Shine, J. and Dalgarno, L. (1975) Eur. J. Biochem. 57: 221–230). Careful assignment of gene function resulted in the identification of the glucose-6-phosphate isomerase gene (pgi), the glucose-6-phosphate 1-dehydrogenase gene (zwf), the 6-phosphogluconolactonase gene (pgl), the 6-phosphogluconate dehydrogenase genes (gnd1 and gnd2), the fructosebisphosphatase gene (fbp), and the fructose-1,6-bisphosphate aldolase gene (fba). The two enzymes of the Entner-Doudoroff pathway, phosphogluconate dehydratase gene (edd) and 2-keto-3-deoxy-6-phosphogluconate aldolase gene (eda) were found probably in operon. The ribosephosphate isomerase gene (rpi), ribulose-5-phosphate 3-epimerase gene (rpe), transketolase gene (tkt), and the transaldolase gene (tal) in the reversible reaction on Pentose-Phosphate cycles were identified. The glyceraldehyde-3-phosphate dehydrogenase genes (gap1 and gap2), phosphoglycerate kinase gene (pgk) the phosphoglycerate mutase (pgm), the enolase gene (eno), and the triose phosphate isomerase genes (tpi1, tpi2, and tpi3) were also identified.

Obviously, numerous modifications and variations on the present invention are possible in light of the above teachings. It is therefore to be understood that within the scope of the appended claims, the invention may be practiced otherwise than as specifically described herein.

What is claimed is:

1. An isolated polynucleotide encoding a protein comprising the amino acid sequence of SEQ ID NO:40.

2. A vector comprising the isolated polynucleotide of claim 1.

3. A host cell comprising the isolated polynucleotide of claim 1.

4. The host cell of claim 3, which is a *Methylophilus* bacterium.

5. The host cell of claim 4, which is a *Methylophilus methylotrophus* bacterium.

6. A method of making a protein comprising:
culturing the host cell of claim 3 for a time and under conditions suitable for expression of the protein; and
collecting said protein.

7. An isolated polynucleotide comprising the nucleotide sequence of SEQ ID NO:39.

8. A vector comprising the isolated polynucleotide of claim 7.

9. A host cell comprising the isolated polynucleotide of claim 7.

10. The host cell of claim 9, which is a *Methylophilus* bacterium.

11. The host cell of claim 10, which is a *Methylophilus methylotrophus* bacterium.

12. A method for making a protein comprising:
culturing the host cell of claim 9 for a time and under conditions suitable for the expression of the polynucleotide to produce a protein; and
collecting said protein.

13. An isolated polynucleotide, which hybridizes under high stringent conditions to the isolated polynucleotide of claim 7 wherein said high stringent conditions are hybridization in 50% formamide, 1 M NaCl, 1% SDS at 37° C., and a wash in 0.1×SSC at 60° C. to 65° C., and wherein said polynucleotide encodes a protein having 6-phosphogluconate dehydrogenase 1 activity.

14. A vector comprising the isolated polynucleotide of claim 13.

15. A host cell comprising the isolated polynucleotide of claim 13.

16. A method of making a protein comprising:
culturing the host cell of claim 15 for a time and under conditions suitable for the expression of the polynucleotide to produce a protein; and
collecting said protein.

17. An isolated polynucleotide, which is at least 95% identical to the polynucleotide of claim 7, and wherein said polynucleotide encodes a protein having 6-phosphogluconate dehydrogenase 1 activity.

18. A vector comprising the isolated polynucleotide of claim 17.

19. A host cell comprising the isolated polynucleotide of claim 17.

20. A method of making a protein comprising:

culturing the host cell of claim 19 for a time and under conditions suitable for the expression of the polynucleotide to produce a protein; and collecting said protein.

* * * * *

SEQUENCE LISTING

<160> NUMBER OF SEQ ID NOS: 42

<210> SEQ ID NO 1
<211> LENGTH: 1653
<212> TYPE: DNA
<213> ORGANISM: Methylophilus methylotrophus
<220> FEATURE:
<221> NAME/KEY: CDS
<222> LOCATION: (1)..(1653)
<223> OTHER INFORMATION:

<400> SEQUENCE: 1

| | | | | | | | | | | | | | | | | |
|---|---|---|---|---|---|---|---|---|---|---|---|---|---|---|---|---|
| atg | gca | aaa | tta | acc | aca | cac | ccg | agc | tgg | cac | gcg | ctg | aac | cag | cat | 48 |
| Met | Ala | Lys | Leu | Thr | Thr | His | Pro | Ser | Trp | His | Ala | Leu | Asn | Gln | His | |
| 1 | | | | 5 | | | | | 10 | | | | | 15 | | |
| caa | att | gaa | atg | cgc | aat | gtt | caa | atg | cgc | gac | ctg | ttc | aaa | caa | aac | 96 |
| Gln | Ile | Glu | Met | Arg | Asn | Val | Gln | Met | Arg | Asp | Leu | Phe | Lys | Gln | Asn | |
| | | | 20 | | | | | 25 | | | | | 30 | | | |
| ccg | aaa | cga | ttt | gaa | gag | ttc | agc | ctc | acc | gta | gaa | gat | gtc | ctg | ctt | 144 |
| Pro | Lys | Arg | Phe | Glu | Glu | Phe | Ser | Leu | Thr | Val | Glu | Asp | Val | Leu | Leu | |
| | 35 | | | | | 40 | | | | | 45 | | | | | |
| gac | tac | tcc | aaa | cac | cgc | att | aca | aaa | gaa | acc | tta | gca | cac | ctg | ttt | 192 |
| Asp | Tyr | Ser | Lys | His | Arg | Ile | Thr | Lys | Glu | Thr | Leu | Ala | His | Leu | Phe | |
| 50 | | | | | 55 | | | | | 60 | | | | | | |
| caa | ctg | gcg | cgt | gac | tcc | aat | att | gag | cac | tgg | cgc | agc | cgc | atg | ttc | 240 |
| Gln | Leu | Ala | Arg | Asp | Ser | Asn | Ile | Glu | His | Trp | Arg | Ser | Arg | Met | Phe | |
| 65 | | | | | 70 | | | | | 75 | | | | | 80 | |
| agc | ggt | gaa | aaa | atc | aat | atc | acc | gaa | aat | cgc | gcc | gta | ctg | cat | acc | 288 |
| Ser | Gly | Glu | Lys | Ile | Asn | Ile | Thr | Glu | Asn | Arg | Ala | Val | Leu | His | Thr | |
| | | | | 85 | | | | | 90 | | | | | 95 | | |
| gca | cta | cgc | aac | cgt | agc | aac | aca | cct | gtg | tat | gtc | gat | ggc | aag | gat | 336 |
| Ala | Leu | Arg | Asn | Arg | Ser | Asn | Thr | Pro | Val | Tyr | Val | Asp | Gly | Lys | Asp | |
| | | | 100 | | | | | 105 | | | | | 110 | | | |
| gtg | atg | cca | gaa | gtg | aat | gcg | gtt | ctc | gca | caa | atg | cgt | agc | ttt | act | 384 |
| Val | Met | Pro | Glu | Val | Asn | Ala | Val | Leu | Ala | Gln | Met | Arg | Ser | Phe | Thr | |
| | | 115 | | | | | 120 | | | | | 125 | | | | |
| gag | cag | gtg | cgt | agc | ggt | cag | tgg | act | ggt | tac | act | ggc | aag | cga | att | 432 |
| Glu | Gln | Val | Arg | Ser | Gly | Gln | Trp | Thr | Gly | Tyr | Thr | Gly | Lys | Arg | Ile | |
| | 130 | | | | | 135 | | | | | 140 | | | | | |
| acc | gat | atc | gtg | aat | att | ggt | atc | ggc | ggc | tcc | gat | ttg | ggg | cct | gtc | 480 |
| Thr | Asp | Ile | Val | Asn | Ile | Gly | Ile | Gly | Gly | Ser | Asp | Leu | Gly | Pro | Val | |
| 145 | | | | | 150 | | | | | 155 | | | | | 160 | |
| atg | gct | tgc | gat | gcc | ttg | aaa | cct | tac | gcc | agt | ccg | gat | tta | aaa | gcg | 528 |
| Met | Ala | Cys | Asp | Ala | Leu | Lys | Pro | Tyr | Ala | Ser | Pro | Asp | Leu | Lys | Ala | |
| | | | | 165 | | | | | 170 | | | | | 175 | | |
| cat | ttt | gtt | tcc | aac | att | gat | ggt | gcg | cac | ctg | atg | cgt | gta | ctg | gaa | 576 |
| His | Phe | Val | Ser | Asn | Ile | Asp | Gly | Ala | His | Leu | Met | Arg | Val | Leu | Glu | |
| | | | 180 | | | | | 185 | | | | | 190 | | | |
| acc | tgt | cat | ccg | gaa | act | acc | ctg | ttt | att | gtg | gcg | tcg | aaa | aca | ttc | 624 |
| Thr | Cys | His | Pro | Glu | Thr | Thr | Leu | Phe | Ile | Val | Ala | Ser | Lys | Thr | Phe | |
| | | 195 | | | | | 200 | | | | | 205 | | | | |
| acc | acg | cag | gaa | acc | atg | acc | aac | gcc | cac | tcc | gcg | cgc | cgc | tgg | ttc | 672 |
| Thr | Thr | Gln | Glu | Thr | Met | Thr | Asn | Ala | His | Ser | Ala | Arg | Arg | Trp | Phe | |
| | 210 | | | | | 215 | | | | | 220 | | | | | |
| cta | aac | gca | gcc | cag | caa | gac | caa | cat | gtg | gcc | aaa | cat | ttt | gtg | gct | 720 |
| Leu | Asn | Ala | Ala | Gln | Gln | Asp | Gln | His | Val | Ala | Lys | His | Phe | Val | Ala | |
| 225 | | | | | 230 | | | | | 235 | | | | | 240 | |
| tta | tcc | acc | aat | gcc | aaa | gcg | gta | cag | gca | ttc | ggc | ata | gat | acc | aac | 768 |
| Leu | Ser | Thr | Asn | Ala | Lys | Ala | Val | Gln | Ala | Phe | Gly | Ile | Asp | Thr | Asn | |
| | | | | 245 | | | | | 250 | | | | | 255 | | |

```
aac atg ttt gct ttc tgg gac tgg gtg ggt ggc cgt tac tcc ttg tgg       816
Asn Met Phe Ala Phe Trp Asp Trp Val Gly Gly Arg Tyr Ser Leu Trp
        260                 265                 270 tca gcc atc ggt tta tcg atc gca ttg tat gtg ggc atg gac aac ttt       864
Ser Ala Ile Gly Leu Ser Ile Ala Leu Tyr Val Gly Met Asp Asn Phe
    275                 280                 285 gaa caa atg ttg gct ggt gga cac gcc atg gac cag cac ttc cag act       912
Glu Gln Met Leu Ala Gly Gly His Ala Met Asp Gln His Phe Gln Thr
290                 295                 300 gcg ccg ttg gaa cag aac atg cct gtt atc atg gca ttg ctc ggc atc       960
Ala Pro Leu Glu Gln Asn Met Pro Val Ile Met Ala Leu Leu Gly Ile
305                 310                 315                 320 tgg tat aac aac ttc ttc cat gtg gat act cac gcg atc ttg cct tac      1008
Trp Tyr Asn Asn Phe Phe His Val Asp Thr His Ala Ile Leu Pro Tyr
                325                 330                 335 gac cag ggg atg tct cgt ttt gca gct tat ttg cag caa gcc gat atg      1056
Asp Gln Gly Met Ser Arg Phe Ala Ala Tyr Leu Gln Gln Ala Asp Met
            340                 345                 350 gaa agt aac ggt aaa ttc att tgc cgt gac ggc agc cgc gtc agc tat      1104
Glu Ser Asn Gly Lys Phe Ile Cys Arg Asp Gly Ser Arg Val Ser Tyr
        355                 360                 365 aaa act gga cca gtc atc tgg ggt gaa gct ggc acc aac ggt cag cac      1152
Lys Thr Gly Pro Val Ile Trp Gly Glu Ala Gly Thr Asn Gly Gln His
370                 375                 380 gca ttc tat cag ctg ata cat cag ggt acg caa atg gtg ccc gct gat      1200
Ala Phe Tyr Gln Leu Ile His Gln Gly Thr Gln Met Val Pro Ala Asp
385                 390                 395                 400 ttc ctg atg cca gct aat agc cat tac aaa gta ggt agc ccg gat gac      1248
Phe Leu Met Pro Ala Asn Ser His Tyr Lys Val Gly Ser Pro Asp Asp
                405                 410                 415 cag cac cac aaa atc ctg ctg gcc aat ttc ctg gct caa aca cag gca      1296
Gln His His Lys Ile Leu Leu Ala Asn Phe Leu Ala Gln Thr Gln Ala
            420                 425                 430 ttg atg ctg ggt aag acc cgt gaa gaa gcg cgt gca gaa ctc gaa aaa      1344
Leu Met Leu Gly Lys Thr Arg Glu Glu Ala Arg Ala Glu Leu Glu Lys
        435                 440                 445 cag gga ctg agt ggc gaa gca ctg gaa gac ttg tta ccg cac aaa gta      1392
Gln Gly Leu Ser Gly Glu Ala Leu Glu Asp Leu Leu Pro His Lys Val
450                 455                 460 ttc gaa ggt aac cgt cct acg acc tcc atc ctg ttc aaa cag ctg acc      1440
Phe Glu Gly Asn Arg Pro Thr Thr Ser Ile Leu Phe Lys Gln Leu Thr
465                 470                 475                 480 cct tat acc ctg ggc aag ctg att gcc ctg tat gag cac aag att ttt      1488
Pro Tyr Thr Leu Gly Lys Leu Ile Ala Leu Tyr Glu His Lys Ile Phe
                485                 490                 495 gtg cag ggt att atc tgg gac atc aac agt tac gac caa tgg ggt gtg      1536
Val Gln Gly Ile Ile Trp Asp Ile Asn Ser Tyr Asp Gln Trp Gly Val
            500                 505                 510 gaa tac ggc aag caa atc gcc agc caa atc ttg cca caa ttg aat aca      1584
Glu Tyr Gly Lys Gln Ile Ala Ser Gln Ile Leu Pro Gln Leu Asn Thr
        515                 520                 525 cca gaa gcg gtg aca ggg ttt gac agc tca acc aac ggc tta atc aat      1632
Pro Glu Ala Val Thr Gly Phe Asp Ser Ser Thr Asn Gly Leu Ile Asn
530                 535                 540 tac gcg aag aaa ata tcg taa                                          1653
Tyr Ala Lys Lys Ile Ser
545                 550
```

<210> SEQ ID NO 2

-continued

```
<211> LENGTH: 550
<212> TYPE: PRT
<213> ORGANISM: Methylophilus methylotrophus

<400> SEQUENCE: 2

Met Ala Lys Leu Thr Thr His Pro Ser Trp His Ala Leu Asn Gln His
1               5                   10                  15

Gln Ile Glu Met Arg Asn Val Gln Met Arg Asp Leu Phe Lys Gln Asn
            20                  25                  30

Pro Lys Arg Phe Glu Glu Phe Ser Leu Thr Val Glu Asp Val Leu Leu
        35                  40                  45

Asp Tyr Ser Lys His Arg Ile Thr Lys Glu Thr Leu Ala His Leu Phe
    50                  55                  60

Gln Leu Ala Arg Asp Ser Asn Ile Glu His Trp Arg Ser Arg Met Phe
65                  70                  75                  80

Ser Gly Glu Lys Ile Asn Ile Thr Glu Asn Arg Ala Val Leu His Thr
                85                  90                  95

Ala Leu Arg Asn Arg Ser Asn Thr Pro Val Tyr Val Asp Gly Lys Asp
            100                 105                 110

Val Met Pro Glu Val Asn Ala Val Leu Ala Gln Met Arg Ser Phe Thr
        115                 120                 125

Glu Gln Val Arg Ser Gly Gln Trp Thr Gly Tyr Thr Gly Lys Arg Ile
    130                 135                 140

Thr Asp Ile Val Asn Ile Gly Ile Gly Gly Ser Asp Leu Gly Pro Val
145                 150                 155                 160

Met Ala Cys Asp Ala Leu Lys Pro Tyr Ala Ser Pro Asp Leu Lys Ala
                165                 170                 175

His Phe Val Ser Asn Ile Asp Gly Ala His Leu Met Arg Val Leu Glu
            180                 185                 190

Thr Cys His Pro Glu Thr Thr Leu Phe Ile Val Ala Ser Lys Thr Phe
        195                 200                 205

Thr Thr Gln Glu Thr Met Thr Asn Ala His Ser Ala Arg Arg Trp Phe
    210                 215                 220

Leu Asn Ala Ala Gln Gln Asp Gln His Val Ala Lys His Phe Val Ala
225                 230                 235                 240

Leu Ser Thr Asn Ala Lys Ala Val Gln Ala Phe Gly Ile Asp Thr Asn
                245                 250                 255

Asn Met Phe Ala Phe Trp Asp Trp Val Gly Gly Arg Tyr Ser Leu Trp
            260                 265                 270

Ser Ala Ile Gly Leu Ser Ile Ala Leu Tyr Val Gly Met Asp Asn Phe
        275                 280                 285

Glu Gln Met Leu Ala Gly Gly His Ala Met Asp Gln His Phe Gln Thr
    290                 295                 300

Ala Pro Leu Glu Gln Asn Met Pro Val Ile Met Ala Leu Leu Gly Ile
305                 310                 315                 320

Trp Tyr Asn Asn Phe Phe His Val Asp Thr His Ala Ile Leu Pro Tyr
                325                 330                 335

Asp Gln Gly Met Ser Arg Phe Ala Ala Tyr Leu Gln Gln Ala Asp Met
            340                 345                 350

Glu Ser Asn Gly Lys Phe Ile Cys Arg Asp Gly Ser Arg Val Ser Tyr
        355                 360                 365

Lys Thr Gly Pro Val Ile Trp Gly Glu Ala Gly Thr Asn Gly Gln His
    370                 375                 380

Ala Phe Tyr Gln Leu Ile His Gln Gly Thr Gln Met Val Pro Ala Asp
```

```
                385                 390                 395                 400
        Phe Leu Met Pro Ala Asn Ser His Tyr Lys Val Gly Ser Pro Asp Asp
                        405                 410                 415

Gln His His Lys Ile Leu Leu Ala Asn Phe Leu Ala Gln Thr Gln Ala
                        420                 425                 430

Leu Met Leu Gly Lys Thr Arg Glu Glu Ala Arg Ala Glu Leu Glu Lys
                        435                 440                 445

Gln Gly Leu Ser Gly Glu Ala Leu Glu Asp Leu Leu Pro His Lys Val
                450                 455                 460

Phe Glu Gly Asn Arg Pro Thr Thr Ser Ile Leu Phe Lys Gln Leu Thr
        465                 470                 475                 480

Pro Tyr Thr Leu Gly Lys Leu Ile Ala Leu Tyr Glu His Lys Ile Phe
                        485                 490                 495

Val Gln Gly Ile Ile Trp Asp Ile Asn Ser Tyr Asp Gln Trp Gly Val
                        500                 505                 510

Glu Tyr Gly Lys Gln Ile Ala Ser Gln Ile Leu Pro Gln Leu Asn Thr
                        515                 520                 525

Pro Glu Ala Val Thr Gly Phe Asp Ser Ser Thr Asn Gly Leu Ile Asn
                530                 535                 540

Tyr Ala Lys Lys Ile Ser
        545                 550

<210> SEQ ID NO 3
<211> LENGTH: 1479
<212> TYPE: DNA
<213> ORGANISM: Methylophilus methylotrophus
<220> FEATURE:
<221> NAME/KEY: CDS
<222> LOCATION: (1)..(1479)
<223> OTHER INFORMATION:

<400> SEQUENCE: 3 atg acg aat aaa att gat cca tgc acc ctg gta ttg ttt ggc gcg agt         48
Met Thr Asn Lys Ile Asp Pro Cys Thr Leu Val Leu Phe Gly Ala Ser
1               5                   10                  15 ggc aac ctg gcc cgc gta aaa cta tat cct ggt ttg ttc agg cta gac         96
Gly Asn Leu Ala Arg Val Lys Leu Tyr Pro Gly Leu Phe Arg Leu Asp
            20                  25                  30 atg ctg ggc cgc ctg cca gat gac atg aaa att atc ggc gtt ggc cgc        144
Met Leu Gly Arg Leu Pro Asp Asp Met Lys Ile Ile Gly Val Gly Arg
        35                  40                  45 caa gtg gtt gat ctg gac gcc tgg cgt gca gac atc aaa tcc atg ctg        192
Gln Val Val Asp Leu Asp Ala Trp Arg Ala Asp Ile Lys Ser Met Leu
    50                  55                  60 gat acc aag ttt aaa aaa ggc tat gac cag aaa gtg ttc gag cgt ttt        240
Asp Thr Lys Phe Lys Lys Gly Tyr Asp Gln Lys Val Phe Glu Arg Phe
65                  70                  75                  80 atc gcc cgt aac ttc tac cat gcc aac ccg ccg acc gat cca gat gct        288
Ile Ala Arg Asn Phe Tyr His Ala Asn Pro Pro Thr Asp Pro Asp Ala
                85                  90                  95 ttc aaa aaa ctg aaa gcg acc ctg agc gac gaa aaa gta ttc ccg cag        336
Phe Lys Lys Leu Lys Ala Thr Leu Ser Asp Glu Lys Val Phe Pro Gln
            100                 105                 110 aac ctg gct tac ttc ctg tct gta cgt ccc gtt gac ttt gcc cca gtg        384
Asn Leu Ala Tyr Phe Leu Ser Val Arg Pro Val Asp Phe Ala Pro Val
        115                 120                 125 gtg gaa tcc ctg gca aat gtt ggc ctg act cag gaa gac aaa tac tgg        432
Val Glu Ser Leu Ala Asn Val Gly Leu Thr Gln Glu Asp Lys Tyr Trp
    130                 135                 140
```

-continued

| | |
|---|---|
| cgt cgt gta gtg atc gag aaa cca ttc ggt act gac ctg cca tct gcg<br>Arg Arg Val Val Ile Glu Lys Pro Phe Gly Thr Asp Leu Pro Ser Ala<br>145                    150                    155                    160 | 480 |
| aaa gag ctg cag gct gcg atc acc aag cac ctc aaa gaa agc caa atc<br>Lys Glu Leu Gln Ala Ala Ile Thr Lys His Leu Lys Glu Ser Gln Ile<br>                  165                    170                    175 | 528 |
| tac cgt atc gac cac tac ctg ggt aaa tct gcc ttg cag aac att ctg<br>Tyr Arg Ile Asp His Tyr Leu Gly Lys Ser Ala Leu Gln Asn Ile Leu<br>              180                    185                    190 | 576 |
| ctg caa cgt ttt acc aat acc gtg tta gag ccg atc tgg aac aat cag<br>Leu Gln Arg Phe Thr Asn Thr Val Leu Glu Pro Ile Trp Asn Asn Gln<br>        195                    200                    205 | 624 |
| tat atc gac cac gta caa atc acc aac acc gaa atg ctg ggt gta ggc<br>Tyr Ile Asp His Val Gln Ile Thr Asn Thr Glu Met Leu Gly Val Gly<br>210                    215                    220 | 672 |
| gac cgt aca cag ttc tat gac agc act ggc gca ttg cgt gac atg cta<br>Asp Arg Thr Gln Phe Tyr Asp Ser Thr Gly Ala Leu Arg Asp Met Leu<br>225                    230                    235                    240 | 720 |
| caa agc cat att ttg caa aca ttg gct tta acc gcc atg gag cag cca<br>Gln Ser His Ile Leu Gln Thr Leu Ala Leu Thr Ala Met Glu Gln Pro<br>                  245                    250                    255 | 768 |
| aaa gac ctg tct cct gaa ggc gtg cgt gat gcg aaa atc aaa ttg ctt<br>Lys Asp Leu Ser Pro Glu Gly Val Arg Asp Ala Lys Ile Lys Leu Leu<br>                  260                    265                    270 | 816 |
| gaa gaa att cgc cca att cca gtt aaa gag ctg gaa aaa cac gca ttc<br>Glu Glu Ile Arg Pro Ile Pro Val Lys Glu Leu Glu Lys His Ala Phe<br>        275                    280                    285 | 864 |
| cgt gca caa tac gct gct ggc gaa atc aac ggc gaa aaa gtc cct ggc<br>Arg Ala Gln Tyr Ala Ala Gly Glu Ile Asn Gly Glu Lys Val Pro Gly<br>290                    295                    300 | 912 |
| tac ctg gaa gaa tta ggc aac aag gac agc gtc gtt gaa acc tat gca<br>Tyr Leu Glu Glu Leu Gly Asn Lys Asp Ser Val Val Glu Thr Tyr Ala<br>305                    310                    315                    320 | 960 |
| gcg ttg aaa ctg ttt atc gat aat ccg cgc tgg aaa ggt gta ccg ttc<br>Ala Leu Lys Leu Phe Ile Asp Asn Pro Arg Trp Lys Gly Val Pro Phe<br>                  325                    330                    335 | 1008 |
| tat atc cgt acg gca aaa cgc ctg cac gaa gcc gac aca cgc att tcc<br>Tyr Ile Arg Thr Ala Lys Arg Leu His Glu Ala Asp Thr Arg Ile Ser<br>                  340                    345                    350 | 1056 |
| atc cgc ttc aag aag gca cct ttg caa atc aat gac cag gac cag aac<br>Ile Arg Phe Lys Lys Ala Pro Leu Gln Ile Asn Asp Gln Asp Gln Asn<br>        355                    360                    365 | 1104 |
| tgg ctc att atc ggc atc cag cct cgc gag tgt atc aag ctg gaa atc<br>Trp Leu Ile Ile Gly Ile Gln Pro Arg Glu Cys Ile Lys Leu Glu Ile<br>370                    375                    380 | 1152 |
| cag tcc aag att cct ggc ctg gac gtg caa aca cgt acc atc cag ctg<br>Gln Ser Lys Ile Pro Gly Leu Asp Val Gln Thr Arg Thr Ile Gln Leu<br>385                    390                    395                    400 | 1200 |
| gat gcg gct aac cgt tgg gat agc gac gac acc gta gat gct tac gaa<br>Asp Ala Ala Asn Arg Trp Asp Ser Asp Asp Thr Val Asp Ala Tyr Glu<br>                  405                    410                    415 | 1248 |
| gcc ctg ttg ctt aac ctg atg caa ggt gac aac tcc aac tat ctg cat<br>Ala Leu Leu Leu Asn Leu Met Gln Gly Asp Asn Ser Asn Tyr Leu His<br>                  420                    425                    430 | 1296 |
| att tct gaa gct gaa gcc caa tgg cgc ctg gtc gac cca gtc gtg aaa<br>Ile Ser Glu Ala Glu Ala Gln Trp Arg Leu Val Asp Pro Val Val Lys<br>435                    440                    445 | 1344 |
| gct tgg gcg gaa gac aag cgc cct gtg cat cag tac cct gct ggc agc<br>Ala Trp Ala Glu Asp Lys Arg Pro Val His Gln Tyr Pro Ala Gly Ser | 1392 |

```
          450                 455                 460
cgt gat ccg att gaa tcc aaa gtg att ttt gaa ggt gaa gac cag ttc    1440
Arg Asp Pro Ile Glu Ser Lys Val Ile Phe Glu Gly Glu Asp Gln Phe
465                 470                 475                 480 tgg cgt tac agc att gaa ctg ggc ggc gac aag ttt tag                1479
Trp Arg Tyr Ser Ile Glu Leu Gly Gly Asp Lys Phe
                485                 490
```

<210> SEQ ID NO 4
<211> LENGTH: 492
<212> TYPE: PRT
<213> ORGANISM: Methylophilus methylotrophus

<400> SEQUENCE: 4

```
Met Thr Asn Lys Ile Asp Pro Cys Thr Leu Val Leu Phe Gly Ala Ser
1               5                   10                  15

Gly Asn Leu Ala Arg Val Lys Leu Tyr Pro Gly Leu Phe Arg Leu Asp
                20                  25                  30

Met Leu Gly Arg Leu Pro Asp Met Lys Ile Ile Gly Val Gly Arg
            35                  40                  45

Gln Val Val Asp Leu Asp Ala Trp Arg Ala Asp Ile Lys Ser Met Leu
    50                  55                  60

Asp Thr Lys Phe Lys Lys Gly Tyr Asp Gln Lys Val Phe Glu Arg Phe
65              70                  75                  80

Ile Ala Arg Asn Phe Tyr His Ala Asn Pro Pro Thr Asp Pro Asp Ala
                85                  90                  95

Phe Lys Lys Leu Lys Ala Thr Leu Ser Asp Glu Lys Val Phe Pro Gln
            100                 105                 110

Asn Leu Ala Tyr Phe Leu Ser Val Arg Pro Val Asp Phe Ala Pro Val
        115                 120                 125

Val Glu Ser Leu Ala Asn Val Gly Leu Thr Gln Glu Asp Lys Tyr Trp
130                 135                 140

Arg Arg Val Val Ile Glu Lys Pro Phe Gly Thr Asp Leu Pro Ser Ala
145                 150                 155                 160

Lys Glu Leu Gln Ala Ala Ile Thr Lys His Leu Lys Glu Ser Gln Ile
                165                 170                 175

Tyr Arg Ile Asp His Tyr Leu Gly Lys Ser Ala Leu Gln Asn Ile Leu
            180                 185                 190

Leu Gln Arg Phe Thr Asn Thr Val Leu Glu Pro Ile Trp Asn Asn Gln
        195                 200                 205

Tyr Ile Asp His Val Gln Ile Thr Asn Thr Glu Met Leu Gly Val Gly
    210                 215                 220

Asp Arg Thr Gln Phe Tyr Asp Ser Thr Gly Ala Leu Arg Asp Met Leu
225                 230                 235                 240

Gln Ser His Ile Leu Gln Thr Leu Ala Leu Thr Ala Met Glu Gln Pro
                245                 250                 255

Lys Asp Leu Ser Pro Glu Gly Val Arg Asp Ala Lys Ile Lys Leu Leu
            260                 265                 270

Glu Glu Ile Arg Pro Ile Pro Val Lys Glu Leu Glu Lys His Ala Phe
        275                 280                 285

Arg Ala Gln Tyr Ala Ala Gly Glu Ile Asn Gly Glu Lys Val Pro Gly
    290                 295                 300

Tyr Leu Glu Glu Leu Gly Asn Lys Asp Ser Val Val Glu Thr Tyr Ala
305                 310                 315                 320

Ala Leu Lys Leu Phe Ile Asp Asn Pro Arg Trp Lys Gly Val Pro Phe
```

-continued

```
                    325                 330                 335
Tyr Ile Arg Thr Ala Lys Arg Leu His Glu Ala Asp Thr Arg Ile Ser
                340                 345                 350

Ile Arg Phe Lys Lys Ala Pro Leu Gln Ile Asn Asp Gln Asp Gln Asn
            355                 360                 365

Trp Leu Ile Ile Gly Ile Gln Pro Arg Glu Cys Ile Lys Leu Glu Ile
        370                 375                 380

Gln Ser Lys Ile Pro Gly Leu Asp Val Gln Thr Arg Thr Ile Gln Leu
385                 390                 395                 400

Asp Ala Ala Asn Arg Trp Asp Ser Asp Thr Val Asp Ala Tyr Glu
                405                 410                 415

Ala Leu Leu Leu Asn Leu Met Gln Gly Asp Asn Ser Asn Tyr Leu His
            420                 425                 430

Ile Ser Glu Ala Glu Ala Gln Trp Arg Leu Val Asp Pro Val Val Lys
        435                 440                 445

Ala Trp Ala Glu Asp Lys Arg Pro Val His Gln Tyr Pro Ala Gly Ser
    450                 455                 460

Arg Asp Pro Ile Glu Ser Lys Val Ile Phe Glu Gly Glu Asp Gln Phe
465                 470                 475                 480

Trp Arg Tyr Ser Ile Glu Leu Gly Gly Asp Lys Phe
                485                 490
```

<210> SEQ ID NO 5
<211> LENGTH: 687
<212> TYPE: DNA
<213> ORGANISM: Methylophilus methylotrophus
<220> FEATURE:
<221> NAME/KEY: CDS
<222> LOCATION: (1)..(687)
<223> OTHER INFORMATION:

<400> SEQUENCE: 5

```
atg tct ttg aat gct caa acc cgt tgg ctc aca ttt caa tcc cag caa      48
Met Ser Leu Asn Ala Gln Thr Arg Trp Leu Thr Phe Gln Ser Gln Gln
1               5                   10                  15 gaa att aat caa gct gcc ctg aac aga att tta gct gct gct gat gcg      96
Glu Ile Asn Gln Ala Ala Leu Asn Arg Ile Leu Ala Ala Ala Asp Ala
            20                  25                  30 gcg att gcc aaa tat ggc agc ttt ctc att gta cta gcc ggt ggc agt     144
Ala Ile Ala Lys Tyr Gly Ser Phe Leu Ile Val Leu Ala Gly Gly Ser
        35                  40                  45 acc ccc aaa gcc gtt tat cag ttg ctg gca aag gct aat gcc gac tgg     192
Thr Pro Lys Ala Val Tyr Gln Leu Leu Ala Lys Ala Asn Ala Asp Trp
    50                  55                  60 gct aac tgg cat gtg tat cac aat gat gac cgc tgc ttg ccg gtc gat     240
Ala Asn Trp His Val Tyr His Asn Asp Asp Arg Cys Leu Pro Val Asp
65                  70                  75                  80 cat gcc gaa cgc aac agc aag atg gca cgc gac gcc tgg tta agc cat     288
His Ala Glu Arg Asn Ser Lys Met Ala Arg Asp Ala Trp Leu Ser His
                85                  90                  95 gtg cct atc cca gaa aat cag att cac gat att cct gcc gag ctg ggc     336
Val Pro Ile Pro Glu Asn Gln Ile His Asp Ile Pro Ala Glu Leu Gly
            100                 105                 110 aat gtg gaa ggc gcc aaa gcc tat gct caa act ctc aaa ggt gtg cgt     384
Asn Val Glu Gly Ala Lys Ala Tyr Ala Gln Thr Leu Lys Gly Val Arg
        115                 120                 125 act ttt gac ctg gtg att ctt ggc ctg ggt gaa gat ggc cat acc gcc     432
Thr Phe Asp Leu Val Ile Leu Gly Leu Gly Glu Asp Gly His Thr Ala
    130                 135                 140
```

```
agc ctg ttc cct ggg caa ctt gtg gac aac tct gct gat gcg gtc cct    480
Ser Leu Phe Pro Gly Gln Leu Val Asp Asn Ser Ala Asp Ala Val Pro
145                 150                 155                 160 gtc tac aac tcc ccc aaa ccg cct gca gac cgt att acc atc agt caa    528
Val Tyr Asn Ser Pro Lys Pro Pro Ala Asp Arg Ile Thr Ile Ser Gln
                165                 170                 175 cat cgc ctc aac aat aca cat gaa gtc atg ttc ctg gtg acc ggg gca    576
His Arg Leu Asn Asn Thr His Glu Val Met Phe Leu Val Thr Gly Ala
            180                 185                 190 ggt aaa caa gag gcg gtc gat cag tgg cgt agc ggg gtt gca atc ccg    624
Gly Lys Gln Glu Ala Val Asp Gln Trp Arg Ser Gly Val Ala Ile Pro
        195                 200                 205 gca aca ttg att caa tcc ccc aat ggt gtg gat gtc tat tgt ttt ggt    672
Ala Thr Leu Ile Gln Ser Pro Asn Gly Val Asp Val Tyr Cys Phe Gly
    210                 215                 220 gtc gag ttg aaa taa                                                687
Val Glu Leu Lys
225

<210> SEQ ID NO 6
<211> LENGTH: 228
<212> TYPE: PRT
<213> ORGANISM: Methylophilus methylotrophus

<400> SEQUENCE: 6

Met Ser Leu Asn Ala Gln Thr Arg Trp Leu Thr Phe Gln Ser Gln Gln
1               5                   10                  15

Glu Ile Asn Gln Ala Ala Leu Asn Arg Ile Leu Ala Ala Ala Asp Ala
            20                  25                  30

Ala Ile Ala Lys Tyr Gly Ser Phe Leu Ile Val Leu Ala Gly Gly Ser
        35                  40                  45

Thr Pro Lys Ala Val Tyr Gln Leu Leu Ala Lys Ala Asn Ala Asp Trp
    50                  55                  60

Ala Asn Trp His Val Tyr His Asn Asp Asp Arg Cys Leu Pro Val Asp
65              70                  75                  80

His Ala Glu Arg Asn Ser Lys Met Ala Arg Asp Ala Trp Leu Ser His
            85                  90                  95

Val Pro Ile Pro Glu Asn Gln Ile His Asp Ile Pro Ala Glu Leu Gly
        100                 105                 110

Asn Val Glu Gly Ala Lys Ala Tyr Ala Gln Thr Leu Lys Gly Val Arg
    115                 120                 125

Thr Phe Asp Leu Val Ile Leu Gly Leu Gly Glu Asp Gly His Thr Ala
130                 135                 140

Ser Leu Phe Pro Gly Gln Leu Val Asp Asn Ser Ala Asp Ala Val Pro
145                 150                 155                 160

Val Tyr Asn Ser Pro Lys Pro Pro Ala Asp Arg Ile Thr Ile Ser Gln
                165                 170                 175

His Arg Leu Asn Asn Thr His Glu Val Met Phe Leu Val Thr Gly Ala
            180                 185                 190

Gly Lys Gln Glu Ala Val Asp Gln Trp Arg Ser Gly Val Ala Ile Pro
        195                 200                 205

Ala Thr Leu Ile Gln Ser Pro Asn Gly Val Asp Val Tyr Cys Phe Gly
    210                 215                 220

Val Glu Leu Lys
225
```

-continued

<210> SEQ ID NO 7
<211> LENGTH: 1815
<212> TYPE: DNA
<213> ORGANISM: Methylophilus methylotrophus
<220> FEATURE:
<221> NAME/KEY: CDS
<222> LOCATION: (1)..(1815)
<223> OTHER INFORMATION:

<400> SEQUENCE: 7

```
atg aaa caa tct cac att gaa gta aca gaa cgc atc atc gag cgt agc      48
Met Lys Gln Ser His Ile Glu Val Thr Glu Arg Ile Ile Glu Arg Ser
1               5                   10                  15 cgt ccg aca cgt aag gcg tat ttg cag cgt att gat gat tac ctg aac      96
Arg Pro Thr Arg Lys Ala Tyr Leu Gln Arg Ile Asp Asp Tyr Leu Asn
            20                  25                  30 cgc gaa aag ggc ccg gat cgt ctg ggc tgc gcc aac gtg gcg cac gca     144
Arg Glu Lys Gly Pro Asp Arg Leu Gly Cys Ala Asn Val Ala His Ala
        35                  40                  45 ttt gcg gct atg cca cag aac gac aag ttc aag att tac gcc gaa aag     192
Phe Ala Ala Met Pro Gln Asn Asp Lys Phe Lys Ile Tyr Ala Glu Lys
    50                  55                  60 cct acc cat gtg ggt atc gtc acc gcg tac aac gaa atg ctg tct gcg     240
Pro Thr His Val Gly Ile Val Thr Ala Tyr Asn Glu Met Leu Ser Ala
65                  70                  75                  80 cat cag cca tat gtc aat tat cca gac att atc cgt gat gaa gca cgc     288
His Gln Pro Tyr Val Asn Tyr Pro Asp Ile Ile Arg Asp Glu Ala Arg
                85                  90                  95 aag cat ggt gcc act gtg cag gtt gct ggt ggt gtg cca gcc atg tgc     336
Lys His Gly Ala Thr Val Gln Val Ala Gly Gly Val Pro Ala Met Cys
            100                 105                 110 gac ggc att acc cag ggt gag cca ggc atg gag ttg agt ctg ttc agc     384
Asp Gly Ile Thr Gln Gly Glu Pro Gly Met Glu Leu Ser Leu Phe Ser
        115                 120                 125 cgc gat acc att gcc atg agt act gct gtg gct tta tct cat gat gta     432
Arg Asp Thr Ile Ala Met Ser Thr Ala Val Ala Leu Ser His Asp Val
    130                 135                 140 ttt gac gct gca tta ctg ttg ggc gtg tgt gac aag att gtg ccg ggg     480
Phe Asp Ala Ala Leu Leu Leu Gly Val Cys Asp Lys Ile Val Pro Gly
145                 150                 155                 160 ctg ctg att ggt gcc ttg cac ttt ggc cat ttg cct tgt gtg ttt gtc     528
Leu Leu Ile Gly Ala Leu His Phe Gly His Leu Pro Cys Val Phe Val
                165                 170                 175 ccc gct ggg ccg atg agc acc ggc att gat aac acc tcc aaa tcc aaa     576
Pro Ala Gly Pro Met Ser Thr Gly Ile Asp Asn Thr Ser Lys Ser Lys
            180                 185                 190 gta cgc gaa aaa tac gcg caa ggt ctg tgt gac cgt gat gaa ttg cta     624
Val Arg Glu Lys Tyr Ala Gln Gly Leu Cys Asp Arg Asp Glu Leu Leu
        195                 200                 205 gca agt gag tca gcg gca tat cac ggc gca ggt act tgc acc ttc tac     672
Ala Ser Glu Ser Ala Ala Tyr His Gly Ala Gly Thr Cys Thr Phe Tyr
    210                 215                 220 gga aca gcc aac agt aac cag atg ctg ctg gaa gcc atg ggt ctg cat     720
Gly Thr Ala Asn Ser Asn Gln Met Leu Leu Glu Ala Met Gly Leu His
225                 230                 235                 240 gtg cca gga gca gcg ttt att cac ccg cat gat ggc atg cgt gag gac     768
Val Pro Gly Ala Ala Phe Ile His Pro His Asp Gly Met Arg Glu Asp
                245                 250                 255 ttg acc cgt gag gct gtg cgc ttg gta ttg caa aat gcc aag aaa gac     816
Leu Thr Arg Glu Ala Val Arg Leu Val Leu Gln Asn Ala Lys Lys Asp
            260                 265                 270
```

```
                                          -continued aaa ttt gtg ccg att ggc cga ctg gta gat gag cac gtg att gtg aat      864
Lys Phe Val Pro Ile Gly Arg Leu Val Asp Glu His Val Ile Val Asn
            275                 280                 285 gcc atg gtg gcc ttg ctg gct acc ggt ggt tct acc aat cat ttg atc      912
Ala Met Val Ala Leu Leu Ala Thr Gly Gly Ser Thr Asn His Leu Ile
        290                 295                 300 cac tgg gta gca gtc gcc cgt gca gcc ggt atc atc att gac tgg act      960
His Trp Val Ala Val Ala Arg Ala Ala Gly Ile Ile Ile Asp Trp Thr
305                 310                 315                 320 gat ttc cac tac ctg gca aaa gcc aca ccg tta ctg gca agt gtg tat     1008
Asp Phe His Tyr Leu Ala Lys Ala Thr Pro Leu Leu Ala Ser Val Tyr
                325                 330                 335 cct aac ggt aag gct gac gtc aac gag ttc cag acc gct gga ggt cct     1056
Pro Asn Gly Lys Ala Asp Val Asn Glu Phe Gln Thr Ala Gly Gly Pro
            340                 345                 350 ggt ttt gtg atc cgt gaa ctg att gag ggg ggc tac atg tac cct gat     1104
Gly Phe Val Ile Arg Glu Leu Ile Glu Gly Gly Tyr Met Tyr Pro Asp
        355                 360                 365 gtc tac act gtt gat ggt ggc gat tta cgt tct tat ggc aaa aaa cct     1152
Val Tyr Thr Val Asp Gly Gly Asp Leu Arg Ser Tyr Gly Lys Lys Pro
370                 375                 380 gaa aaa gaa ggt gac aag ctg gtc tgg aag gac tac ccg gca gaa agc     1200
Glu Lys Glu Gly Asp Lys Leu Val Trp Lys Asp Tyr Pro Ala Glu Ser
                385                 390                 395                 400 ggt gac gaa acc atc gtc cgt acc gca gca cat ccg ttc aat gag tca     1248
Gly Asp Glu Thr Ile Val Arg Thr Ala Ala His Pro Phe Asn Glu Ser
            405                 410                 415 ggt ggc ctg cgt ttg ctt aaa ggt aat tta ggc cgt agc gtg atc aag     1296
Gly Gly Leu Arg Leu Leu Lys Gly Asn Leu Gly Arg Ser Val Ile Lys
        420                 425                 430 att tct gcg gtg cca gaa gac cgt cat att att gaa gcg cct gcg att     1344
Ile Ser Ala Val Pro Glu Asp Arg His Ile Ile Glu Ala Pro Ala Ile
                435                 440                 445 gtg ttt gat gca cag gaa gag ctg ctg gca gcc ttc gac cgt ggt gag     1392
Val Phe Asp Ala Gln Glu Glu Leu Leu Ala Ala Phe Asp Arg Gly Glu
450                 455                 460 ctg gaa aaa gac ttt gtt gcc gtg gtg cgt ttc cag ggc cct aaa gcc     1440
Leu Glu Lys Asp Phe Val Ala Val Val Arg Phe Gln Gly Pro Lys Ala
465                 470                 475                 480 aat ggt atg cca gag ctg cat aaa ctg aca cca ccg ctg gct gta ttg     1488
Asn Gly Met Pro Glu Leu His Lys Leu Thr Pro Pro Leu Ala Val Leu
            485                 490                 495 cag aac aag ggt ttc cgc gta gcg att gtg aca gat gga cgt atg agt     1536
Gln Asn Lys Gly Phe Arg Val Ala Ile Val Thr Asp Gly Arg Met Ser
        500                 505                 510 ggc gct tcc ggc aag atc ccg gca gca att cac ttg agt cct gaa gca     1584
Gly Ala Ser Gly Lys Ile Pro Ala Ala Ile His Leu Ser Pro Glu Ala
                515                 520                 525 agc gct gga ggc ccc att gcg aaa atc cgc aac ggc gac att atc cgc     1632
Ser Ala Gly Gly Pro Ile Ala Lys Ile Arg Asn Gly Asp Ile Ile Arg
530                 535                 540 ttg aat ggt acc gtc ggt cag ttg aat gtg ctg gtt gat gaa gac acc     1680
Leu Asn Gly Thr Val Gly Gln Leu Asn Val Leu Val Asp Glu Asp Thr
545                 550                 555                 560 tgg gct gag cgc gag gct gaa gag tta agc gat gcc aag cgt cat tac     1728
Trp Ala Glu Arg Glu Ala Glu Glu Leu Ser Asp Ala Lys Arg His Tyr
            565                 570                 575 aac gca cat ggc ttg ggc cgt gag ttg ttt ggt ggc atg cgc agg aat     1776
Asn Ala His Gly Leu Gly Arg Glu Leu Phe Gly Gly Met Arg Arg Asn
        580                 585                 590
```

-continued

```
gtg ttg tca gcc gaa gag ggc gca gtt act tgg ctg taa          1815
Val Leu Ser Ala Glu Glu Gly Ala Val Thr Trp Leu
    595                 600
```

<210> SEQ ID NO 8
<211> LENGTH: 604
<212> TYPE: PRT
<213> ORGANISM: Methylophilus methylotrophus

<400> SEQUENCE: 8

```
Met Lys Gln Ser His Ile Glu Val Thr Glu Arg Ile Ile Glu Arg Ser
 1               5                  10                  15

Arg Pro Thr Arg Lys Ala Tyr Leu Gln Arg Ile Asp Asp Tyr Leu Asn
            20                  25                  30

Arg Glu Lys Gly Pro Asp Arg Leu Gly Cys Ala Asn Val Ala His Ala
        35                  40                  45

Phe Ala Ala Met Pro Gln Asn Asp Lys Phe Lys Ile Tyr Ala Glu Lys
    50                  55                  60

Pro Thr His Val Gly Ile Val Thr Ala Tyr Asn Glu Met Leu Ser Ala
65                  70                  75                  80

His Gln Pro Tyr Val Asn Tyr Pro Asp Ile Ile Arg Asp Glu Ala Arg
                85                  90                  95

Lys His Gly Ala Thr Val Gln Val Ala Gly Val Pro Ala Met Cys
            100                 105                 110

Asp Gly Ile Thr Gln Gly Glu Pro Gly Met Glu Leu Ser Leu Phe Ser
        115                 120                 125

Arg Asp Thr Ile Ala Met Ser Thr Ala Val Ala Leu Ser His Asp Val
    130                 135                 140

Phe Asp Ala Ala Leu Leu Leu Gly Val Cys Asp Lys Ile Val Pro Gly
145                 150                 155                 160

Leu Leu Ile Gly Ala Leu His Phe Gly His Leu Pro Cys Val Phe Val
                165                 170                 175

Pro Ala Gly Pro Met Ser Thr Gly Ile Asp Asn Thr Ser Lys Ser Lys
            180                 185                 190

Val Arg Glu Lys Tyr Ala Gln Gly Leu Cys Asp Arg Asp Glu Leu Leu
        195                 200                 205

Ala Ser Glu Ser Ala Ala Tyr His Gly Ala Gly Thr Cys Thr Phe Tyr
    210                 215                 220

Gly Thr Ala Asn Ser Asn Gln Met Leu Leu Glu Ala Met Gly Leu His
225                 230                 235                 240

Val Pro Gly Ala Ala Phe Ile His Pro His Asp Gly Met Arg Glu Asp
                245                 250                 255

Leu Thr Arg Glu Ala Val Arg Leu Val Leu Gln Asn Ala Lys Lys Asp
            260                 265                 270

Lys Phe Val Pro Ile Gly Arg Leu Val Asp Glu His Val Ile Val Asn
        275                 280                 285

Ala Met Val Ala Leu Leu Ala Thr Gly Gly Ser Thr Asn His Leu Ile
    290                 295                 300

His Trp Val Ala Val Ala Arg Ala Ala Gly Ile Ile Ile Asp Trp Thr
305                 310                 315                 320

Asp Phe His Tyr Leu Ala Lys Ala Thr Pro Leu Leu Ala Ser Val Tyr
                325                 330                 335

Pro Asn Gly Lys Ala Asp Val Asn Glu Phe Gln Thr Ala Gly Gly Pro
            340                 345                 350
```

```
Gly Phe Val Ile Arg Glu Leu Ile Glu Gly Gly Tyr Met Tyr Pro Asp
            355                 360                 365

Val Tyr Thr Val Asp Gly Gly Asp Leu Arg Ser Tyr Gly Lys Lys Pro
        370                 375                 380

Glu Lys Glu Gly Asp Lys Leu Val Trp Lys Asp Tyr Pro Ala Glu Ser
385                 390                 395                 400

Gly Asp Glu Thr Ile Val Arg Thr Ala Ala His Pro Phe Asn Glu Ser
                405                 410                 415

Gly Gly Leu Arg Leu Leu Lys Gly Asn Leu Gly Arg Ser Val Ile Lys
            420                 425                 430

Ile Ser Ala Val Pro Glu Asp Arg His Ile Ile Glu Ala Pro Ala Ile
        435                 440                 445

Val Phe Asp Ala Gln Glu Leu Leu Ala Ala Phe Asp Arg Gly Glu
    450                 455                 460

Leu Glu Lys Asp Phe Val Ala Val Arg Phe Gln Gly Pro Lys Ala
465                 470                 475                 480

Asn Gly Met Pro Glu Leu His Lys Leu Thr Pro Pro Leu Ala Val Leu
                485                 490                 495

Gln Asn Lys Gly Phe Arg Val Ala Ile Val Thr Asp Gly Arg Met Ser
            500                 505                 510

Gly Ala Ser Gly Lys Ile Pro Ala Ala Ile His Leu Ser Pro Glu Ala
        515                 520                 525

Ser Ala Gly Gly Pro Ile Ala Lys Ile Arg Asn Gly Asp Ile Ile Arg
    530                 535                 540

Leu Asn Gly Thr Val Gly Gln Leu Asn Val Leu Val Asp Glu Asp Thr
545                 550                 555                 560

Trp Ala Glu Arg Glu Ala Glu Leu Ser Asp Ala Lys Arg His Tyr
                565                 570                 575

Asn Ala His Gly Leu Gly Arg Glu Leu Phe Gly Gly Met Arg Arg Asn
            580                 585                 590

Val Leu Ser Ala Glu Glu Gly Ala Val Thr Trp Leu
        595                 600

<210> SEQ ID NO 9
<211> LENGTH: 630
<212> TYPE: DNA
<213> ORGANISM: Methylophilus methylotrophus
<220> FEATURE:
<221> NAME/KEY: CDS
<222> LOCATION: (1)..(630)
<223> OTHER INFORMATION:

<400> SEQUENCE: 9 atg agc aca tta gag tta gct aac cat ggc ccg gtg att ccg gtc att      48
Met Ser Thr Leu Glu Leu Ala Asn His Gly Pro Val Ile Pro Val Ile
1               5                   10                  15 gtc atc aac aaa gtg gaa gat gct gtg cct atg gca gaa gcc ctg ctg      96
Val Ile Asn Lys Val Glu Asp Ala Val Pro Met Ala Glu Ala Leu Leu
                20                  25                  30 gaa ggc ggt ata aag gtg ctg gaa gtg act ttg cgt tca cca gtg gct     144
Glu Gly Gly Ile Lys Val Leu Glu Val Thr Leu Arg Ser Pro Val Ala
            35                  40                  45 ttg cat gcc atg gag gaa att gcc aaa cat gtg cca gat gcg att tta     192
Leu His Ala Met Glu Glu Ile Ala Lys His Val Pro Asp Ala Ile Leu
        50                  55                  60 ggt tcc ggc acc gtg cgt aat ctc aag gat gct aag aac tca aaa gat     240
Gly Ser Gly Thr Val Arg Asn Leu Lys Asp Ala Lys Asn Ser Lys Asp
65                  70                  75                  80
```

```
gca ggt tgc cag ttt gca gtg agt cca ggc tac acc agc gag ttg ggt      288
Ala Gly Cys Gln Phe Ala Val Ser Pro Gly Tyr Thr Ser Glu Leu Gly
             85                  90                  95 aaa tat gcc cgt gaa att ggt ttg cca tta ctg cca ggc gtg tct aca      336
Lys Tyr Ala Arg Glu Ile Gly Leu Pro Leu Leu Pro Gly Val Ser Thr
        100                 105                 110 ggc tca gag atc atg atg gcg aat gcg gat gat tac tac ttc ctg aaa      384
Gly Ser Glu Ile Met Met Ala Asn Ala Asp Asp Tyr Tyr Phe Leu Lys
    115                 120                 125 ctg ttc cca gcc gta gcg gtg ggt ggc att aac ctg ctt aaa ggc ttt      432
Leu Phe Pro Ala Val Ala Val Gly Gly Ile Asn Leu Leu Lys Gly Phe
130                 135                 140 gcc ggg ccg ttt gct gat gtg aaa ttc tgc cca aca ggt ggc gtg agc      480
Ala Gly Pro Phe Ala Asp Val Lys Phe Cys Pro Thr Gly Gly Val Ser
145                 150                 155                 160 gtt gaa agt gca cca cag ttc ttg gca ctg cca aat gtg gtt gtg tgt      528
Val Glu Ser Ala Pro Gln Phe Leu Ala Leu Pro Asn Val Val Val Cys
                165                 170                 175 ggt ggt acc tgg ttg acg cct gca gat gcc gtc gca aac aaa gat tgg      576
Gly Gly Thr Trp Leu Thr Pro Ala Asp Ala Val Ala Asn Lys Asp Trp
            180                 185                 190 gcg cat atc acc aag ctg gcg aaa gaa gca tcg gcg att gtc gct gcg      624
Ala His Ile Thr Lys Leu Ala Lys Glu Ala Ser Ala Ile Val Ala Ala
        195                 200                 205 aaa taa                                                              630
Lys

<210> SEQ ID NO 10
<211> LENGTH: 209
<212> TYPE: PRT
<213> ORGANISM: Methylophilus methylotrophus

<400> SEQUENCE: 10

Met Ser Thr Leu Glu Leu Ala Asn His Gly Pro Val Ile Pro Val Ile
1               5                   10                  15

Val Ile Asn Lys Val Glu Asp Ala Val Pro Met Ala Glu Ala Leu Leu
            20                  25                  30

Glu Gly Gly Ile Lys Val Leu Glu Val Thr Leu Arg Ser Pro Val Ala
        35                  40                  45

Leu His Ala Met Glu Glu Ile Ala Lys His Val Pro Asp Ala Ile Leu
    50                  55                  60

Gly Ser Gly Thr Val Arg Asn Leu Lys Asp Ala Lys Asn Ser Lys Asp
65                  70                  75                  80

Ala Gly Cys Gln Phe Ala Val Ser Pro Gly Tyr Thr Ser Glu Leu Gly
                85                  90                  95

Lys Tyr Ala Arg Glu Ile Gly Leu Pro Leu Leu Pro Gly Val Ser Thr
            100                 105                 110

Gly Ser Glu Ile Met Met Ala Asn Ala Asp Asp Tyr Tyr Phe Leu Lys
        115                 120                 125

Leu Phe Pro Ala Val Ala Val Gly Gly Ile Asn Leu Leu Lys Gly Phe
    130                 135                 140

Ala Gly Pro Phe Ala Asp Val Lys Phe Cys Pro Thr Gly Gly Val Ser
145                 150                 155                 160

Val Glu Ser Ala Pro Gln Phe Leu Ala Leu Pro Asn Val Val Val Cys
                165                 170                 175

Gly Gly Thr Trp Leu Thr Pro Ala Asp Ala Val Ala Asn Lys Asp Trp
            180                 185                 190
```

```
Ala His Ile Thr Lys Leu Ala Lys Glu Ala Ser Ala Ile Val Ala Ala
        195                 200                 205

Lys

<210> SEQ ID NO 11
<211> LENGTH: 669
<212> TYPE: DNA
<213> ORGANISM: Methylophilus methylotrophus
<220> FEATURE:
<221> NAME/KEY: CDS
<222> LOCATION: (1)..(669)
<223> OTHER INFORMATION:

<400> SEQUENCE: 11 atg gcg atg gat aaa gca caa caa gac gca ctt aaa ctg gaa gtg gcg      48
Met Ala Met Asp Lys Ala Gln Gln Asp Ala Leu Lys Leu Glu Val Ala
1               5                   10                  15 aaa gcg gct gta acc tat gtg aaa gat ggc att atc ggc gtt ggc act      96
Lys Ala Ala Val Thr Tyr Val Lys Asp Gly Ile Ile Gly Val Gly Thr
            20                  25                  30 ggc tcg act gcc aac ttt ttt att gat gaa ctg gcc aag gtc aaa cac     144
Gly Ser Thr Ala Asn Phe Phe Ile Asp Glu Leu Ala Lys Val Lys His
        35                  40                  45 aaa att act ggc gca gtt gcc agc tcc gaa gcc acc gcg caa cgc ctg     192
Lys Ile Thr Gly Ala Val Ala Ser Ser Glu Ala Thr Ala Gln Arg Leu
    50                  55                  60 cgt aac cac ggt atc gaa gta ttc gat ttg aac agt gta gac agc ctg     240
Arg Asn His Gly Ile Glu Val Phe Asp Leu Asn Ser Val Asp Ser Leu
65                  70                  75                  80 gat att tat gta gac ggc gcg gat gaa atc acc gaa cac atg cat atg     288
Asp Ile Tyr Val Asp Gly Ala Asp Glu Ile Thr Glu His Met His Met
                85                  90                  95 ctt aaa ggc ggc ggt ggt gcg ttg acc cga gaa aag atc gtg gca gct     336
Leu Lys Gly Gly Gly Gly Ala Leu Thr Arg Glu Lys Ile Val Ala Ala
            100                 105                 110 gtg gcc aaa tct ttc atc tgt atc tgt gac gaa agc aaa ttc gta ccc     384
Val Ala Lys Ser Phe Ile Cys Ile Cys Asp Glu Ser Lys Phe Val Pro
        115                 120                 125 gtc ttg ggc aag ttt ccc ctg cca gta gaa gta tta ccg atg gca cgc     432
Val Leu Gly Lys Phe Pro Leu Pro Val Glu Val Leu Pro Met Ala Arg
    130                 135                 140 agc cat gtg gca cgt gaa ctg gtg aaa ctg ggt ggt caa cca cag ttg     480
Ser His Val Ala Arg Glu Leu Val Lys Leu Gly Gly Gln Pro Gln Leu
145                 150                 155                 160 cgt gac ttc acg acg gat aac ggc aac ctg att ctg gac gtg cat ggt     528
Arg Asp Phe Thr Thr Asp Asn Gly Asn Leu Ile Leu Asp Val His Gly
                165                 170                 175 tta acc atc agt gac cca atc gcc atg gaa gcc aaa atc aac cag atc     576
Leu Thr Ile Ser Asp Pro Ile Ala Met Glu Ala Lys Ile Asn Gln Ile
            180                 185                 190 gtc ggc gtg gtg acc aat ggt tta ttt gct gcc cgt cca gcc aat gta     624
Val Gly Val Val Thr Asn Gly Leu Phe Ala Ala Arg Pro Ala Asn Val
        195                 200                 205 ctc ctg ttg gcg act cca acc ggc gtc aaa acg ctg aca aaa taa         669
Leu Leu Leu Ala Thr Pro Thr Gly Val Lys Thr Leu Thr Lys
    210                 215                 220

<210> SEQ ID NO 12
<211> LENGTH: 222
<212> TYPE: PRT
<213> ORGANISM: Methylophilus methylotrophus
```

<400> SEQUENCE: 12

```
Met Ala Met Asp Lys Ala Gln Gln Asp Ala Leu Lys Leu Glu Val Ala
1               5                   10                  15

Lys Ala Ala Val Thr Tyr Val Lys Asp Gly Ile Ile Gly Val Gly Thr
            20                  25                  30

Gly Ser Thr Ala Asn Phe Phe Ile Asp Glu Leu Ala Lys Val Lys His
        35                  40                  45

Lys Ile Thr Gly Ala Val Ala Ser Ser Glu Ala Thr Ala Gln Arg Leu
50                  55                  60

Arg Asn His Gly Ile Glu Val Phe Asp Leu Asn Ser Val Asp Ser Leu
65                  70                  75                  80

Asp Ile Tyr Val Asp Gly Ala Asp Glu Ile Thr Glu His Met His Met
                85                  90                  95

Leu Lys Gly Gly Gly Gly Ala Leu Thr Arg Glu Lys Ile Val Ala Ala
            100                 105                 110

Val Ala Lys Ser Phe Ile Cys Ile Cys Asp Glu Ser Lys Phe Val Pro
        115                 120                 125

Val Leu Gly Lys Phe Pro Leu Pro Val Glu Val Leu Pro Met Ala Arg
    130                 135                 140

Ser His Val Ala Arg Glu Leu Val Lys Leu Gly Gly Gln Pro Gln Leu
145                 150                 155                 160

Arg Asp Phe Thr Thr Asp Asn Gly Asn Leu Ile Leu Asp Val His Gly
                165                 170                 175

Leu Thr Ile Ser Asp Pro Ile Ala Met Glu Ala Lys Ile Asn Gln Ile
            180                 185                 190

Val Gly Val Val Thr Asn Gly Leu Phe Ala Ala Arg Pro Ala Asn Val
        195                 200                 205

Leu Leu Leu Ala Thr Pro Thr Gly Val Lys Thr Leu Thr Lys
    210                 215                 220
```

<210> SEQ ID NO 13
<211> LENGTH: 708
<212> TYPE: DNA
<213> ORGANISM: Methylophilus methylotrophus
<220> FEATURE:
<221> NAME/KEY: CDS
<222> LOCATION: (1)..(708)
<223> OTHER INFORMATION:

<400> SEQUENCE: 13

```
atg gac aaa act ttt cgc att gcc cca agt att ctt tct gcc aac ttt      48
Met Asp Lys Thr Phe Arg Ile Ala Pro Ser Ile Leu Ser Ala Asn Phe
1               5                   10                  15 gcc aaa cta ggc cag gaa atc gaa aac gtc att aaa tct ggc aca gac      96
Ala Lys Leu Gly Gln Glu Ile Glu Asn Val Ile Lys Ser Gly Thr Asp
            20                  25                  30 atc gtt cac ttt gac gtc atg gat aat cac tat gtg cct aac ctg act     144
Ile Val His Phe Asp Val Met Asp Asn His Tyr Val Pro Asn Leu Thr
        35                  40                  45 atc ggc cca ttg gtc tgt gat gcg att cgt gat ctg tca cac aat gta     192
Ile Gly Pro Leu Val Cys Asp Ala Ile Arg Asp Leu Ser His Asn Val
    50                  55                  60 ggc gcc ctg att gat gtg cac ctg atg gtc aaa cca gta gac cgc atc     240
Gly Ala Leu Ile Asp Val His Leu Met Val Lys Pro Val Asp Arg Ile
65                  70                  75                  80 att cct gac ttt gcc aaa gcg ggt gct gac atc atc aca ttc cac ccg     288
Ile Pro Asp Phe Ala Lys Ala Gly Ala Asp Ile Ile Thr Phe His Pro
```

-continued

```
                    85                  90                  95
gaa gcc tct gac cac att gac cgt agc ctg gcc ttg atc cgc gat agc     336
Glu Ala Ser Asp His Ile Asp Arg Ser Leu Ala Leu Ile Arg Asp Ser
            100                 105                 110 ggt tgc aag tct ggc ctg gta ttt aac cca gcc aca ccg ttg cat tac     384
Gly Cys Lys Ser Gly Leu Val Phe Asn Pro Ala Thr Pro Leu His Tyr
                115                 120                 125 ctg gat tac gta atg gat aaa gtg gac atg att ttg ctg atg tcg gtg     432
Leu Asp Tyr Val Met Asp Lys Val Asp Met Ile Leu Leu Met Ser Val
    130                 135                 140 aac ccg ggg ttt ggt ggc cag aaa ttc att cca tcc acc ttg gat aaa     480
Asn Pro Gly Phe Gly Gly Gln Lys Phe Ile Pro Ser Thr Leu Asp Lys
145                 150                 155                 160 ctg aaa cag gcc cgt gcc cgc att gac gct tat tac gaa aaa act ggc     528
Leu Lys Gln Ala Arg Ala Arg Ile Asp Ala Tyr Tyr Glu Lys Thr Gly
                165                 170                 175 cgc cag atc tgg ctg gaa gta gat ggt ggc gtc aac gca aac aac att     576
Arg Gln Ile Trp Leu Glu Val Asp Gly Gly Val Asn Ala Asn Asn Ile
            180                 185                 190 gca gag atc gca aaa gcc ggg gct gat acc ttc gtc gca ggt agt gcg     624
Ala Glu Ile Ala Lys Ala Gly Ala Asp Thr Phe Val Ala Gly Ser Ala
        195                 200                 205 att ttc ggt tca cct aaa gac acc gat cct aac cgt tac gat aca gtt     672
Ile Phe Gly Ser Pro Lys Asp Thr Asp Pro Asn Arg Tyr Asp Thr Val
    210                 215                 220 gtg gcg gcg atg cgt gct tcc tta gcc act gtt taa                     708
Val Ala Ala Met Arg Ala Ser Leu Ala Thr Val
225                 230                 235
```

<210> SEQ ID NO 14
<211> LENGTH: 235
<212> TYPE: PRT
<213> ORGANISM: Methylophilus methylotrophus

<400> SEQUENCE: 14

```
Met Asp Lys Thr Phe Arg Ile Ala Pro Ser Ile Leu Ser Ala Asn Phe
1               5                   10                  15

Ala Lys Leu Gly Gln Glu Ile Glu Asn Val Ile Lys Ser Gly Thr Asp
                20                  25                  30

Ile Val His Phe Asp Val Met Asp Asn His Tyr Val Pro Asn Leu Thr
            35                  40                  45

Ile Gly Pro Leu Val Cys Asp Ala Ile Arg Asp Leu Ser His Asn Val
        50                  55                  60

Gly Ala Leu Ile Asp Val His Leu Met Val Lys Pro Val Asp Arg Ile
65                  70                  75                  80

Ile Pro Asp Phe Ala Lys Ala Gly Ala Asp Ile Ile Thr Phe His Pro
                85                  90                  95

Glu Ala Ser Asp His Ile Asp Arg Ser Leu Ala Leu Ile Arg Asp Ser
            100                 105                 110

Gly Cys Lys Ser Gly Leu Val Phe Asn Pro Ala Thr Pro Leu His Tyr
        115                 120                 125

Leu Asp Tyr Val Met Asp Lys Val Asp Met Ile Leu Leu Met Ser Val
    130                 135                 140

Asn Pro Gly Phe Gly Gly Gln Lys Phe Ile Pro Ser Thr Leu Asp Lys
145                 150                 155                 160

Leu Lys Gln Ala Arg Ala Arg Ile Asp Ala Tyr Tyr Glu Lys Thr Gly
                165                 170                 175
```

```
Arg Gln Ile Trp Leu Glu Val Asp Gly Gly Val Asn Ala Asn Asn Ile
        180                 185                 190

Ala Glu Ile Ala Lys Ala Gly Ala Asp Thr Phe Val Ala Gly Ser Ala
    195                 200                 205

Ile Phe Gly Ser Pro Lys Asp Thr Asp Pro Asn Arg Tyr Asp Thr Val
        210                 215                 220

Val Ala Ala Met Arg Ala Ser Leu Ala Thr Val
225                 230                 235

<210> SEQ ID NO 15
<211> LENGTH: 1986
<212> TYPE: DNA
<213> ORGANISM: Methylophilus methylotrophus
<220> FEATURE:
<221> NAME/KEY: CDS
<222> LOCATION: (1)..(1986)
<223> OTHER INFORMATION:

<400> SEQUENCE: 15 atg gca act cgt gtc gac ttg tgc aac gcc atc cgt gct ctg agc atg      48
Met Ala Thr Arg Val Asp Leu Cys Asn Ala Ile Arg Ala Leu Ser Met
1               5                   10                  15 gac gct gta caa aaa gca aac tcc ggc cac cca ggc gca cct atg ggc      96
Asp Ala Val Gln Lys Ala Asn Ser Gly His Pro Gly Ala Pro Met Gly
            20                  25                  30 atg gct gaa att gct gaa gta ttg tgg aac cac aat ctg agc cac aac     144
Met Ala Glu Ile Ala Glu Val Leu Trp Asn His Asn Leu Ser His Asn
        35                  40                  45 cca aac aac cca caa tgg gct aac cgt gat cgt ttc gta ttg tcc aac     192
Pro Asn Asn Pro Gln Trp Ala Asn Arg Asp Arg Phe Val Leu Ser Asn
    50                  55                  60 ggc cat ggc tcc atg ctg att tac tcc ttg ctg cac ctg act ggt tac     240
Gly His Gly Ser Met Leu Ile Tyr Ser Leu Leu His Leu Thr Gly Tyr
65                  70                  75                  80 gat gtg acc atg gac gac atc aag tca ttc cgt caa ctg cac tcc cgt     288
Asp Val Thr Met Asp Asp Ile Lys Ser Phe Arg Gln Leu His Ser Arg
                85                  90                  95 tgc gct ggt cac cca gag tac ggc tac gca cct ggc gtt gaa aca acc     336
Cys Ala Gly His Pro Glu Tyr Gly Tyr Ala Pro Gly Val Glu Thr Thr
            100                 105                 110 acg ggt ccg ttg ggc caa ggt att gcg aac ggc gtt ggt ttt gcc atg     384
Thr Gly Pro Leu Gly Gln Gly Ile Ala Asn Gly Val Gly Phe Ala Met
        115                 120                 125 gca gaa aaa ctg ctg gct agc caa ttc aac aag cca ggc cac gac atc     432
Ala Glu Lys Leu Leu Ala Ser Gln Phe Asn Lys Pro Gly His Asp Ile
    130                 135                 140 gtt gac cac tac aca tac gtg ttc ctg ggc gac ggc tgt atg atg gaa     480
Val Asp His Tyr Thr Tyr Val Phe Leu Gly Asp Gly Cys Met Met Glu
145                 150                 155                 160 ggc gtt tct cac gaa gct tgt gca ctt gct ggt aca tgg ggc ctg ggc     528
Gly Val Ser His Glu Ala Cys Ala Leu Ala Gly Thr Trp Gly Leu Gly
                165                 170                 175 aaa ctg atc gct ttc tgg gat gac aac ggt att tct atc gac ggc cac     576
Lys Leu Ile Ala Phe Trp Asp Asp Asn Gly Ile Ser Ile Asp Gly His
            180                 185                 190 atc gaa ggc tgg tac aca gac gac acc gca ggc cgc ttc aaa gct tac     624
Ile Glu Gly Trp Tyr Thr Asp Asp Thr Ala Gly Arg Phe Lys Ala Tyr
        195                 200                 205 ggc tgg cac gtt gtt tca gta gat ggt cac gac cag gct gcg att cag     672
Gly Trp His Val Val Ser Val Asp Gly His Asp Gln Ala Ala Ile Gln
    210                 215                 220
```

```
aaa gct atc gac gaa gct aaa tca gtg act gac aaa cca tca ctg atc    720
Lys Ala Ile Asp Glu Ala Lys Ser Val Thr Asp Lys Pro Ser Leu Ile
225             230                 235                 240 tgc tgc aaa acc atc att ggt aaa ggt tca cca aac aag tgc ggt tca    768
Cys Cys Lys Thr Ile Ile Gly Lys Gly Ser Pro Asn Lys Cys Gly Ser
                245                 250                 255 cac gac tgc cac ggt tcc gca tta ggc gaa gct gaa gtt gct gca acc    816
His Asp Cys His Gly Ser Ala Leu Gly Glu Ala Glu Val Ala Ala Thr
            260                 265                 270 cgt gaa gcc atc ggc tgg cca cac gca cct ttt gaa att cct gct gac    864
Arg Glu Ala Ile Gly Trp Pro His Ala Pro Phe Glu Ile Pro Ala Asp
        275                 280                 285 gta tac gaa ggc tgg aac caa aaa gac aaa ggt gca aaa cgc gaa gct    912
Val Tyr Glu Gly Trp Asn Gln Lys Asp Lys Gly Ala Lys Arg Glu Ala
    290                 295                 300 gac tgg aac gcg aag ttt gac gct tac gct aaa gcc tac cca gca gaa    960
Asp Trp Asn Ala Lys Phe Asp Ala Tyr Ala Lys Ala Tyr Pro Ala Glu
305                 310                 315                 320 gct gca gaa ttc aaa cgc cgt atg gcc ggt gaa ttg cca gct aac tgg   1008
Ala Ala Glu Phe Lys Arg Arg Met Ala Gly Glu Leu Pro Ala Asn Trp
                325                 330                 335 aag tca ctg act gac gca atc atc gct gaa acc aac gaa aaa gct gag   1056
Lys Ser Leu Thr Asp Ala Ile Ile Ala Glu Thr Asn Glu Lys Ala Glu
            340                 345                 350 aaa ttg gct act cgt caa gct tca caa aaa gca att aca gcg ttg gcg   1104
Lys Leu Ala Thr Arg Gln Ala Ser Gln Lys Ala Ile Thr Ala Leu Ala
        355                 360                 365 cca atc ttg cca gaa ttc ctg ggc ggt tca gct gac ttg aca ggt tct   1152
Pro Ile Leu Pro Glu Phe Leu Gly Gly Ser Ala Asp Leu Thr Gly Ser
    370                 375                 380 aac ctg aca tcc tct aaa gac ttc aaa cac gtg agt ggt aaa gag cca   1200
Asn Leu Thr Ser Ser Lys Asp Phe Lys His Val Ser Gly Lys Glu Pro
385                 390                 395                 400 ggc aac tac atc tct tac ggt gta cgt gag ttc ggt atg gct gca atc   1248
Gly Asn Tyr Ile Ser Tyr Gly Val Arg Glu Phe Gly Met Ala Ala Ile
                405                 410                 415 atg aac ggt atg gca ttg cac ggt ggc ttg ttg cct tac ggc ggt acc   1296
Met Asn Gly Met Ala Leu His Gly Gly Leu Leu Pro Tyr Gly Gly Thr
            420                 425                 430 ttc cac atg ttc tct gac tac atg aaa aac ggc atg cgt atg tct gcg   1344
Phe His Met Phe Ser Asp Tyr Met Lys Asn Gly Met Arg Met Ser Ala
        435                 440                 445 ttg atg cat caa cgt gtg atc tac gtg ctg acc cat gac tct atc ggt   1392
Leu Met His Gln Arg Val Ile Tyr Val Leu Thr His Asp Ser Ile Gly
    450                 455                 460 caa ggt gaa gat ggt cct aca cac caa cca gtt gaa aac act gct ggt   1440
Gln Gly Glu Asp Gly Pro Thr His Gln Pro Val Glu Asn Thr Ala Gly
465                 470                 475                 480 ctg cgt atg att cct cgt atg gat gta tgg cgt cca gct gac tct aca   1488
Leu Arg Met Ile Pro Arg Met Asp Val Trp Arg Pro Ala Asp Ser Thr
                485                 490                 495 gaa aca acc gtt gca tgg gtt gct gca gta gag cgc act gaa ggc cca   1536
Glu Thr Thr Val Ala Trp Val Ala Ala Val Glu Arg Thr Glu Gly Pro
            500                 505                 510 acc agc ttg gta ttg agc cgt caa gct gtg cca ggc atc aag cac gat   1584
Thr Ser Leu Val Leu Ser Arg Gln Ala Val Pro Gly Ile Lys His Asp
        515                 520                 525 gct aaa gac ttt gaa ctg atc cgc aag ggt ggt tat gta ttc tca gac   1632
Ala Lys Asp Phe Glu Leu Ile Arg Lys Gly Gly Tyr Val Phe Ser Asp
```

-continued

```
                       530                 535                 540
gct gca ggt aaa gcg gat gtg atc atc att gct aac ggt tcc gag ttg         1680
Ala Ala Gly Lys Ala Asp Val Ile Ile Ile Ala Asn Gly Ser Glu Leu
545                 550                 555                 560 gat ctg gcg att caa gcg gct gct gaa ttg aac gct gcg ggt act aaa         1728
Asp Leu Ala Ile Gln Ala Ala Ala Glu Leu Asn Ala Ala Gly Thr Lys
                565                 570                 575 gtg cgt gtg gtt tcc atg cca tcc acc aac gta ttc gac cgt caa gac         1776
Val Arg Val Val Ser Met Pro Ser Thr Asn Val Phe Asp Arg Gln Asp
            580                 585                 590 cag gct tac aaa gac agc gta ttg act cca ggc gtt aaa cgc gtg gct         1824
Gln Ala Tyr Lys Asp Ser Val Leu Thr Pro Gly Val Lys Arg Val Ala
        595                 600                 605 gtt gaa gct gct cac cca gat ttc tgg cgt aag tat gtt ggt ctg gaa         1872
Val Glu Ala Ala His Pro Asp Phe Trp Arg Lys Tyr Val Gly Leu Glu
    610                 615                 620 ggt gca gtt gtt ggt atc gat acc ttc ggc gaa tcc gca cca ggc ggc         1920
Gly Ala Val Val Gly Ile Asp Thr Phe Gly Glu Ser Ala Pro Gly Gly
625                 630                 635                 640 gca ctg ttc aaa cac ttc ggc ttc aca gtt gaa aac gta gtc aac aca         1968
Ala Leu Phe Lys His Phe Gly Phe Thr Val Glu Asn Val Val Asn Thr
                645                 650                 655 gtt aaa tcc gta ctg taa                                                 1986
Val Lys Ser Val Leu
            660

<210> SEQ ID NO 16
<211> LENGTH: 661
<212> TYPE: PRT
<213> ORGANISM: Methylophilus methylotrophus

<400> SEQUENCE: 16

Met Ala Thr Arg Val Asp Leu Cys Asn Ala Ile Arg Ala Leu Ser Met
1               5                  10                  15

Asp Ala Val Gln Lys Ala Asn Ser Gly His Pro Gly Ala Pro Met Gly
            20                  25                  30

Met Ala Glu Ile Ala Glu Val Leu Trp Asn His Asn Leu Ser His Asn
        35                  40                  45

Pro Asn Asn Pro Gln Trp Ala Asn Arg Asp Arg Phe Val Leu Ser Asn
    50                  55                  60

Gly His Gly Ser Met Leu Ile Tyr Ser Leu Leu His Leu Thr Gly Tyr
65                  70                  75                  80

Asp Val Thr Met Asp Asp Ile Lys Ser Phe Arg Gln Leu His Ser Arg
                85                  90                  95

Cys Ala Gly His Pro Glu Tyr Gly Tyr Ala Pro Gly Val Glu Thr Thr
            100                 105                 110

Thr Gly Pro Leu Gly Gln Gly Ile Ala Asn Gly Val Gly Phe Ala Met
        115                 120                 125

Ala Glu Lys Leu Leu Ala Ser Gln Phe Asn Lys Pro Gly His Asp Ile
    130                 135                 140

Val Asp His Tyr Thr Tyr Val Phe Leu Gly Asp Gly Cys Met Met Glu
145                 150                 155                 160

Gly Val Ser His Glu Ala Cys Ala Leu Ala Gly Thr Trp Gly Leu Gly
                165                 170                 175

Lys Leu Ile Ala Phe Trp Asp Asp Asn Gly Ile Ser Ile Asp Gly His
            180                 185                 190

Ile Glu Gly Trp Tyr Thr Asp Asp Thr Ala Gly Arg Phe Lys Ala Tyr
```

-continued

```
            195                 200                 205
Gly Trp His Val Ser Val Asp Gly His Asp Gln Ala Ala Ile Gln
210                 215                 220
Lys Ala Ile Asp Glu Ala Lys Ser Val Thr Asp Lys Pro Ser Leu Ile
225                 230                 235                 240
Cys Cys Lys Thr Ile Ile Gly Lys Gly Ser Pro Asn Lys Cys Gly Ser
                245                 250                 255
His Asp Cys His Gly Ser Ala Leu Gly Glu Ala Glu Val Ala Ala Thr
            260                 265                 270
Arg Glu Ala Ile Gly Trp Pro His Ala Pro Phe Glu Ile Pro Ala Asp
            275                 280                 285
Val Tyr Glu Gly Trp Asn Gln Lys Asp Lys Gly Ala Lys Arg Glu Ala
    290                 295                 300
Asp Trp Asn Ala Lys Phe Asp Ala Tyr Ala Lys Ala Tyr Pro Ala Glu
305                 310                 315                 320
Ala Ala Glu Phe Lys Arg Arg Met Ala Gly Glu Leu Pro Ala Asn Trp
                325                 330                 335
Lys Ser Leu Thr Asp Ala Ile Ile Ala Glu Thr Asn Glu Lys Ala Glu
            340                 345                 350
Lys Leu Ala Thr Arg Gln Ala Ser Gln Lys Ala Ile Thr Ala Leu Ala
            355                 360                 365
Pro Ile Leu Pro Glu Phe Leu Gly Gly Ser Ala Asp Leu Thr Gly Ser
    370                 375                 380
Asn Leu Thr Ser Ser Lys Asp Phe Lys His Val Ser Gly Lys Glu Pro
385                 390                 395                 400
Gly Asn Tyr Ile Ser Tyr Gly Val Arg Glu Phe Gly Met Ala Ala Ile
                405                 410                 415
Met Asn Gly Met Ala Leu His Gly Gly Leu Leu Pro Tyr Gly Gly Thr
            420                 425                 430
Phe His Met Phe Ser Asp Tyr Met Lys Asn Gly Met Arg Met Ser Ala
            435                 440                 445
Leu Met His Gln Arg Val Ile Tyr Val Leu Thr His Asp Ser Ile Gly
    450                 455                 460
Gln Gly Glu Asp Gly Pro Thr His Gln Pro Val Glu Asn Thr Ala Gly
465                 470                 475                 480
Leu Arg Met Ile Pro Arg Met Asp Val Trp Arg Pro Ala Asp Ser Thr
                485                 490                 495
Glu Thr Thr Val Ala Trp Val Ala Val Glu Arg Thr Glu Gly Pro
            500                 505                 510
Thr Ser Leu Val Leu Ser Arg Gln Ala Val Pro Gly Ile Lys His Asp
            515                 520                 525
Ala Lys Asp Phe Glu Leu Ile Arg Lys Gly Gly Tyr Val Phe Ser Asp
    530                 535                 540
Ala Ala Gly Lys Ala Asp Val Ile Ile Ala Asn Gly Ser Glu Leu
545                 550                 555                 560
Asp Leu Ala Ile Gln Ala Ala Glu Leu Asn Ala Ala Gly Thr Lys
                565                 570                 575
Val Arg Val Val Ser Met Pro Ser Thr Asn Val Phe Asp Arg Gln Asp
            580                 585                 590
Gln Ala Tyr Lys Asp Ser Val Leu Thr Pro Gly Val Lys Arg Val Ala
            595                 600                 605
Val Glu Ala Ala His Pro Asp Phe Trp Arg Lys Tyr Val Gly Leu Glu
    610                 615                 620
```

<210> SEQ ID NO 17
<211> LENGTH: 954
<212> TYPE: DNA
<213> ORGANISM: Methylophilus methylotrophus
<220> FEATURE:
<221> NAME/KEY: CDS
<222> LOCATION: (1)..(954)
<223> OTHER INFORMATION:

<400> SEQUENCE: 17

| | | | | | | | | | | | | | | | | |
|---|---|---|---|---|---|---|---|---|---|---|---|---|---|---|---|---|
| atg | gca | aac | tta | tta | gat | cag | ttg | aaa | gca | atg | aca | acc | atc | gtg | gct | 48 |
| Met | Ala | Asn | Leu | Leu | Asp | Gln | Leu | Lys | Ala | Met | Thr | Thr | Ile | Val | Ala | |
| 1 | | | | 5 | | | | | 10 | | | | | 15 | | |
| gac | act | ggt | gat | gtt | gaa | gca | atc | aaa | agt | gtt | aaa | cct | gtg | gat | gca | 96 |
| Asp | Thr | Gly | Asp | Val | Glu | Ala | Ile | Lys | Ser | Val | Lys | Pro | Val | Asp | Ala | |
| | | | 20 | | | | | 25 | | | | | 30 | | | |
| acc | aca | aac | cca | tct | ctg | gtg | ttg | aaa | gcc | agc | caa | atc | cca | gaa | tac | 144 |
| Thr | Thr | Asn | Pro | Ser | Leu | Val | Leu | Lys | Ala | Ser | Gln | Ile | Pro | Glu | Tyr | |
| | | 35 | | | | | 40 | | | | | 45 | | | | |
| gca | ccg | ttg | att | gac | act | gcc | att | gct | tat | gca | aaa | gca | caa | ggt | ggt | 192 |
| Ala | Pro | Leu | Ile | Asp | Thr | Ala | Ile | Ala | Tyr | Ala | Lys | Ala | Gln | Gly | Gly | |
| | 50 | | | | | 55 | | | | | 60 | | | | | |
| tcc | aaa | gag | caa | caa | att | gaa | aat | gct | gct | gac | aaa | ctg | gca | gta | ttg | 240 |
| Ser | Lys | Glu | Gln | Gln | Ile | Glu | Asn | Ala | Ala | Asp | Lys | Leu | Ala | Val | Leu | |
| 65 | | | | | 70 | | | | | 75 | | | | | 80 | |
| att | ggc | gct | gaa | atc | act | aaa | gtg | gtt | cca | ggc | cgt | att | tct | aca | gaa | 288 |
| Ile | Gly | Ala | Glu | Ile | Thr | Lys | Val | Val | Pro | Gly | Arg | Ile | Ser | Thr | Glu | |
| | | | | 85 | | | | | 90 | | | | | 95 | | |
| gta | gat | gca | cgt | ttg | tct | ttc | aac | atc | gat | gcg | atg | att | gct | aaa | ggc | 336 |
| Val | Asp | Ala | Arg | Leu | Ser | Phe | Asn | Ile | Asp | Ala | Met | Ile | Ala | Lys | Gly | |
| | | | 100 | | | | | 105 | | | | | 110 | | | |
| cgt | aaa | ttg | atc | aag | ttg | tac | gaa | gag | tct | ggc | atc | agc | aaa | gac | cgc | 384 |
| Arg | Lys | Leu | Ile | Lys | Leu | Tyr | Glu | Glu | Ser | Gly | Ile | Ser | Lys | Asp | Arg | |
| | | 115 | | | | | 120 | | | | | 125 | | | | |
| gta | ctg | atc | aaa | ctt | gct | tct | acc | tgg | gaa | ggt | atc | aag | gct | ggt | gag | 432 |
| Val | Leu | Ile | Lys | Leu | Ala | Ser | Thr | Trp | Glu | Gly | Ile | Lys | Ala | Gly | Glu | |
| | 130 | | | | | 135 | | | | | 140 | | | | | |
| cag | ctg | gaa | aaa | gaa | ggt | atc | cag | tgt | aac | ctg | aca | ttg | tta | ttc | ggt | 480 |
| Gln | Leu | Glu | Lys | Glu | Gly | Ile | Gln | Cys | Asn | Leu | Thr | Leu | Leu | Phe | Gly | |
| 145 | | | | | 150 | | | | | 155 | | | | | 160 | |
| ttc | ggc | cag | gcg | cgc | gca | tgt | gct | gaa | gct | ggc | gtg | ttc | ctg | atc | tcc | 528 |
| Phe | Gly | Gln | Ala | Arg | Ala | Cys | Ala | Glu | Ala | Gly | Val | Phe | Leu | Ile | Ser | |
| | | | | 165 | | | | | 170 | | | | | 175 | | |
| cca | ttc | gtt | ggc | cgt | atc | ctg | gac | tgg | tac | aaa | gcg | aaa | aat | cca | ggg | 576 |
| Pro | Phe | Val | Gly | Arg | Ile | Leu | Asp | Trp | Tyr | Lys | Ala | Lys | Asn | Pro | Gly | |
| | | | 180 | | | | | 185 | | | | | 190 | | | |
| act | gag | tac | act | caa | gaa | act | gac | cca | ggt | gta | gtt | tct | gtt | cgt | gca | 624 |
| Thr | Glu | Tyr | Thr | Gln | Glu | Thr | Asp | Pro | Gly | Val | Val | Ser | Val | Arg | Ala | |
| | | 195 | | | | | 200 | | | | | 205 | | | | |
| atc | tac | cag | tac | tac | aaa | gag | cac | ggc | tac | aaa | acc | gtt | gtg | atg | ggt | 672 |
| Ile | Tyr | Gln | Tyr | Tyr | Lys | Glu | His | Gly | Tyr | Lys | Thr | Val | Val | Met | Gly | |
| | 210 | | | | | 215 | | | | | 220 | | | | | |
| gct | tct | ttc | cgt | aac | act | ggt | gaa | ctg | att | gcg | ctg | gct | ggt | tgt | gac | 720 |
| Ala | Ser | Phe | Arg | Asn | Thr | Gly | Glu | Leu | Ile | Ala | Leu | Ala | Gly | Cys | Asp | |

Gly Ala Val Gly Ile Asp Thr Phe Gly Glu Ser Ala Pro Gly Gly
625             630             635             640

Ala Leu Phe Lys His Phe Gly Phe Thr Val Glu Asn Val Val Asn Thr
                645             650             655

Val Lys Ser Val Leu
            660

```
Ala Ser Phe Arg Asn Thr Gly Glu Leu Ile Ala Leu Ala Gly Cys Asp
225                 230                 235                 240 cgt ttg acc gtg tcc cca aac ctg ctg caa gaa ttg gca gcg aca gaa        768
Arg Leu Thr Val Ser Pro Asn Leu Leu Gln Glu Leu Ala Ala Thr Glu
                    245                 250                 255 ggt aca ttg gct caa gtg ttg aaa gac ggt ggc aag act aaa gac gtg        816
Gly Thr Leu Ala Gln Val Leu Lys Asp Gly Gly Lys Thr Lys Asp Val
                260                 265                 270 cca gct aaa atg act gaa gaa gaa ttc cgc ttc cag ttg aat cag gac        864
Pro Ala Lys Met Thr Glu Glu Glu Phe Arg Phe Gln Leu Asn Gln Asp
            275                 280                 285 gcc atg gcg act gaa aaa ctg gca gaa ggt att cgc ggt ttc gtg gct        912
Ala Met Ala Thr Glu Lys Leu Ala Glu Gly Ile Arg Gly Phe Val Ala
        290                 295                 300 gac cag aaa aaa ctg gaa gac gct tta gcc gca aaa ctg taa                954
Asp Gln Lys Lys Leu Glu Asp Ala Leu Ala Ala Lys Leu
305                 310                 315
```

<210> SEQ ID NO 18
<211> LENGTH: 317
<212> TYPE: PRT
<213> ORGANISM: Methylophilus methylotrophus

<400> SEQUENCE: 18

```
Met Ala Asn Leu Leu Asp Gln Leu Lys Ala Met Thr Thr Ile Val Ala
1               5                   10                  15

Asp Thr Gly Asp Val Glu Ala Ile Lys Ser Val Lys Pro Val Asp Ala
                20                  25                  30

Thr Thr Asn Pro Ser Leu Val Leu Lys Ala Ser Gln Ile Pro Glu Tyr
            35                  40                  45

Ala Pro Leu Ile Asp Thr Ala Ile Ala Tyr Ala Lys Ala Gln Gly Gly
        50                  55                  60

Ser Lys Glu Gln Gln Ile Glu Asn Ala Ala Asp Lys Leu Ala Val Leu
65                  70                  75                  80

Ile Gly Ala Glu Ile Thr Lys Val Val Pro Gly Arg Ile Ser Thr Glu
                85                  90                  95

Val Asp Ala Arg Leu Ser Phe Asn Ile Asp Ala Met Ile Ala Lys Gly
                100                 105                 110

Arg Lys Leu Ile Lys Leu Tyr Glu Glu Ser Gly Ile Ser Lys Asp Arg
            115                 120                 125

Val Leu Ile Lys Leu Ala Ser Thr Trp Glu Gly Ile Lys Ala Gly Glu
        130                 135                 140

Gln Leu Glu Lys Glu Gly Ile Gln Cys Asn Leu Thr Leu Leu Phe Gly
145                 150                 155                 160

Phe Gly Gln Ala Arg Ala Cys Ala Glu Ala Gly Val Phe Leu Ile Ser
                165                 170                 175

Pro Phe Val Gly Arg Ile Leu Asp Trp Tyr Lys Ala Lys Asn Pro Gly
                180                 185                 190

Thr Glu Tyr Thr Gln Glu Thr Asp Pro Gly Val Val Ser Val Arg Ala
            195                 200                 205

Ile Tyr Gln Tyr Tyr Lys Glu His Gly Tyr Lys Thr Val Val Met Gly
        210                 215                 220

Ala Ser Phe Arg Asn Thr Gly Glu Leu Ile Ala Leu Ala Gly Cys Asp
225                 230                 235                 240

Arg Leu Thr Val Ser Pro Asn Leu Leu Gln Glu Leu Ala Ala Thr Glu
                245                 250                 255
```

```
Gly Thr Leu Ala Gln Val Leu Lys Asp Gly Lys Thr Lys Asp Val
            260                 265                 270

Pro Ala Lys Met Thr Glu Glu Phe Arg Phe Gln Leu Asn Gln Asp
        275                 280                 285

Ala Met Ala Thr Glu Lys Leu Ala Glu Gly Ile Arg Gly Phe Val Ala
        290                 295                 300

Asp Gln Lys Lys Leu Glu Asp Ala Leu Ala Lys Leu
305                 310                 315

<210> SEQ ID NO 19
<211> LENGTH: 1017
<212> TYPE: DNA
<213> ORGANISM: Methylophilus methylotrophus
<220> FEATURE:
<221> NAME/KEY: CDS
<222> LOCATION: (1)..(1017)
<223> OTHER INFORMATION:

<400> SEQUENCE: 19 gtg aca tgt ggc cac att tgc tta atc cat aaa ggt att gcc atg caa      48
Val Thr Cys Gly His Ile Cys Leu Ile His Lys Gly Ile Ala Met Gln
1               5                   10                  15 ttg gac gtg ttt tta aaa aag gtt tct atc aat cat gcc ctt aat acg     96
Leu Asp Val Phe Leu Lys Lys Val Ser Ile Asn His Ala Leu Asn Thr
            20                  25                  30 ctg atc tgg cat att gcc gag gcg ggc att gag att gct gcg ctg gtc    144
Leu Ile Trp His Ile Ala Glu Ala Gly Ile Glu Ile Ala Ala Leu Val
        35                  40                  45 agg cag ggc gca ttg gcg ggg gtc acc gaa aaa atg acc agt acc aat    192
Arg Gln Gly Ala Leu Ala Gly Val Thr Glu Lys Met Thr Ser Thr Asn
    50                  55                  60 gtg cag ggt gaa aca cag atg cat ctg gat atc cgt agt cac gaa gtg    240
Val Gln Gly Glu Thr Gln Met His Leu Asp Ile Arg Ser His Glu Val
65                  70                  75                  80 gcg ctg gcc cag tta cgg acc tct gca gtg gta gct gct gtg tta tct    288
Ala Leu Ala Gln Leu Arg Thr Ser Ala Val Val Ala Ala Val Leu Ser
                85                  90                  95 gaa gaa gag gat cag cct gtg ttg ttt gaa aca ttg gag gcg cct ttc    336
Glu Glu Glu Asp Gln Pro Val Leu Phe Glu Thr Leu Glu Ala Pro Phe
            100                 105                 110 ctg gtc agc atg gat cct ttg gac ggt tct tcc aac ctg gcg att aac    384
Leu Val Ser Met Asp Pro Leu Asp Gly Ser Ser Asn Leu Ala Ile Asn
        115                 120                 125 ggt gtg gtg ggt agt att ttc tcg gta ttg ccc aat act ggc ctg gca    432
Gly Val Val Gly Ser Ile Phe Ser Val Leu Pro Asn Thr Gly Leu Ala
    130                 135                 140 acc ctt ggc gag cag gct ttt tta cag ccg ggc aag gat cag cgt gcg    480
Thr Leu Gly Glu Gln Ala Phe Leu Gln Pro Gly Lys Asp Gln Arg Ala
145                 150                 155                 160 gcg gct tat atc atg tat ggg cca gcg act ttg ctg gtg ctg acg att    528
Ala Ala Tyr Ile Met Tyr Gly Pro Ala Thr Leu Leu Val Leu Thr Ile
                165                 170                 175 ggt cag ggc acg cat gtg ttt aca ttg gac cat agc agc cag gcg ttt    576
Gly Gln Gly Thr His Val Phe Thr Leu Asp His Ser Ser Gln Ala Phe
            180                 185                 190 gta ttg aca caa caa aca gtc aaa gtc ccc gaa gaa acc aca gag ttt    624
Val Leu Thr Gln Gln Thr Val Lys Val Pro Glu Glu Thr Thr Glu Phe
        195                 200                 205 gcc atc aat gcc agt aat cag cgt tat tgg caa ccc gcc atg cag cgc    672
Ala Ile Asn Ala Ser Asn Gln Arg Tyr Trp Gln Pro Ala Met Gln Arg
    210                 215                 220
```

```
tat att atg gaa tgt ctg caa ggt tta gaa ggg ccg cgt gga cgc gac       720
Tyr Ile Met Glu Cys Leu Gln Gly Leu Glu Gly Pro Arg Gly Arg Asp
225                 230                 235                 240 ttt aat atg cgc tgg tgt gca agt atg gtg atg gat gta cat cgg atc       768
Phe Asn Met Arg Trp Cys Ala Ser Met Val Met Asp Val His Arg Ile
            245                 250                 255 ctg acg cgt gga ggg gtg ttc ctt tat ccg cgt gat agc aag caa ccg       816
Leu Thr Arg Gly Gly Val Phe Leu Tyr Pro Arg Asp Ser Lys Gln Pro
        260                 265                 270 gtg aaa gcc ggg agg tta aga ttg ttg tat gaa gcc aac ccc atg agc       864
Val Lys Ala Gly Arg Leu Arg Leu Leu Tyr Glu Ala Asn Pro Met Ser
    275                 280                 285 ttg ctg gtg acg cag gcg ggc ggc gaa agt ata gac ggg ctg caa gag       912
Leu Leu Val Thr Gln Ala Gly Gly Glu Ser Ile Asp Gly Leu Gln Glu
290                 295                 300 gtt ctg acc atc gca ccg gat agc tgc cat cag cgc gtg cca gtg ttg       960
Val Leu Thr Ile Ala Pro Asp Ser Cys His Gln Arg Val Pro Val Leu
305                 310                 315                 320 cta ggc tca aaa cag gaa att cag cgc ttg cgc gac tat cat cag caa      1008
Leu Gly Ser Lys Gln Glu Ile Gln Arg Leu Arg Asp Tyr His Gln Gln
            325                 330                 335 gcc gat tag                                                          1017
Ala Asp <210> SEQ ID NO 20
<211> LENGTH: 338
<212> TYPE: PRT
<213> ORGANISM: Methylophilus methylotrophus

<400> SEQUENCE: 20

Val Thr Cys Gly His Ile Cys Leu Ile His Lys Gly Ile Ala Met Gln
1               5                   10                  15

Leu Asp Val Phe Leu Lys Lys Val Ser Ile Asn His Ala Leu Asn Thr
            20                  25                  30

Leu Ile Trp His Ile Ala Glu Ala Gly Ile Glu Ile Ala Ala Leu Val
        35                  40                  45

Arg Gln Gly Ala Leu Ala Gly Val Thr Glu Lys Met Thr Ser Thr Asn
    50                  55                  60

Val Gln Gly Glu Thr Gln Met His Leu Asp Ile Arg Ser His Glu Val
65                  70                  75                  80

Ala Leu Ala Gln Leu Arg Thr Ser Ala Val Ala Ala Val Leu Ser
            85                  90                  95

Glu Glu Glu Asp Gln Pro Val Leu Phe Glu Thr Leu Glu Ala Pro Phe
            100                 105                 110

Leu Val Ser Met Asp Pro Leu Asp Gly Ser Ser Asn Leu Ala Ile Asn
        115                 120                 125

Gly Val Gly Ser Ile Phe Ser Val Leu Pro Asn Thr Gly Leu Ala
    130                 135                 140

Thr Leu Gly Glu Gln Ala Phe Leu Gln Pro Gly Lys Asp Gln Arg Ala
145                 150                 155                 160

Ala Ala Tyr Ile Met Tyr Gly Pro Ala Thr Leu Val Leu Thr Ile
            165                 170                 175

Gly Gln Gly Thr His Val Phe Thr Leu Asp His Ser Ser Gln Ala Phe
        180                 185                 190

Val Leu Thr Gln Gln Thr Val Lys Val Pro Glu Glu Thr Thr Glu Phe
    195                 200                 205
```

```
Ala Ile Asn Ala Ser Asn Gln Arg Tyr Trp Gln Pro Ala Met Gln Arg
        210                 215                 220

Tyr Ile Met Glu Cys Leu Gln Gly Leu Glu Gly Pro Arg Gly Arg Asp
225                 230                 235                 240

Phe Asn Met Arg Trp Cys Ala Ser Met Val Met Asp Val His Arg Ile
                245                 250                 255

Leu Thr Arg Gly Gly Val Phe Leu Tyr Pro Arg Asp Ser Lys Gln Pro
            260                 265                 270

Val Lys Ala Gly Arg Leu Arg Leu Leu Tyr Glu Ala Asn Pro Met Ser
        275                 280                 285

Leu Leu Val Thr Gln Ala Gly Gly Glu Ser Ile Asp Gly Leu Gln Glu
    290                 295                 300

Val Leu Thr Ile Ala Pro Asp Ser Cys His Gln Arg Val Pro Val Leu
305                 310                 315                 320

Leu Gly Ser Lys Gln Glu Ile Gln Arg Leu Arg Asp Tyr His Gln Gln
                325                 330                 335

Ala Asp

<210> SEQ ID NO 21
<211> LENGTH: 1035
<212> TYPE: DNA
<213> ORGANISM: Methylophilus methylotrophus
<220> FEATURE:
<221> NAME/KEY: CDS
<222> LOCATION: (1)..(1035)
<223> OTHER INFORMATION:

<400> SEQUENCE: 21
```

| | | | | | | | | | | | | | | | | |
|---|---|---|---|---|---|---|---|---|---|---|---|---|---|---|---|---|
| atg gca ttg atc tca ctc agg cag ttg ctg gac cac gct gcg gaa cat | | | | | | | | | | | | | | | | 48 |
| Met Ala Leu Ile Ser Leu Arg Gln Leu Leu Asp His Ala Ala Glu His | | | | | | | | | | | | | | | | |
| 1 | | | | 5 | | | | | 10 | | | | | 15 | | |
| agt tat ggt tac ccg gca ttc aat atc aat aat atg gag cag ata ctc | | | | | | | | | | | | | | | | 96 |
| Ser Tyr Gly Tyr Pro Ala Phe Asn Ile Asn Asn Met Glu Gln Ile Leu | | | | | | | | | | | | | | | | |
| | | | 20 | | | | | 25 | | | | | 30 | | | |
| tcc atc atg aaa gcc gct gat gaa gta gat agt gcg gtg att ttg cag | | | | | | | | | | | | | | | | 144 |
| Ser Ile Met Lys Ala Ala Asp Glu Val Asp Ser Ala Val Ile Leu Gln | | | | | | | | | | | | | | | | |
| | | 35 | | | | | 40 | | | | | 45 | | | | |
| gcg tcg gct ggt gca aga ggc tat gct ggt gag tca ttc ctg cgc aag | | | | | | | | | | | | | | | | 192 |
| Ala Ser Ala Gly Ala Arg Gly Tyr Ala Gly Glu Ser Phe Leu Arg Lys | | | | | | | | | | | | | | | | |
| 50 | | | | | 55 | | | | | 60 | | | | | | |
| atg gtg gaa gct gcc att gag caa tac ccg cat att cca gtc tgt atg | | | | | | | | | | | | | | | | 240 |
| Met Val Glu Ala Ala Ile Glu Gln Tyr Pro His Ile Pro Val Cys Met | | | | | | | | | | | | | | | | |
| 65 | | | | | 70 | | | | | 75 | | | | | 80 | |
| cac cag gat cat gga act tcg ccc aag att tgc cag atg gcg ata cgc | | | | | | | | | | | | | | | | 288 |
| His Gln Asp His Gly Thr Ser Pro Lys Ile Cys Gln Met Ala Ile Arg | | | | | | | | | | | | | | | | |
| | | | | 85 | | | | | 90 | | | | | 95 | | |
| agc ggg ttt tcc agc gtg atg atg gat ggc tct ttg aaa gaa gat cat | | | | | | | | | | | | | | | | 336 |
| Ser Gly Phe Ser Ser Val Met Met Asp Gly Ser Leu Lys Glu Asp His | | | | | | | | | | | | | | | | |
| | | | 100 | | | | | 105 | | | | | 110 | | | |
| aaa acg cca gcc agt tat gat tac aat gtg gat gtc acg cgt cgt gtt | | | | | | | | | | | | | | | | 384 |
| Lys Thr Pro Ala Ser Tyr Asp Tyr Asn Val Asp Val Thr Arg Arg Val | | | | | | | | | | | | | | | | |
| | | 115 | | | | | 120 | | | | | 125 | | | | |
| gtc gag ttt gcc cat gcg gtg ggg gtt tcg gta gaa ggc gag ctt ggt | | | | | | | | | | | | | | | | 432 |
| Val Glu Phe Ala His Ala Val Gly Val Ser Val Glu Gly Glu Leu Gly | | | | | | | | | | | | | | | | |
| 130 | | | | | 135 | | | | | 140 | | | | | | |
| gta ctc ggc tcg ctt gaa act ggc atg gca ggc gag gag gat ggg gta | | | | | | | | | | | | | | | | 480 |
| Val Leu Gly Ser Leu Glu Thr Gly Met Ala Gly Glu Glu Asp Gly Val | | | | | | | | | | | | | | | | |
| 145 | | | | | 150 | | | | | 155 | | | | | 160 | |
| ggg gca gaa ggt aag ctg gat gaa tcc caa ttg ctg acc gac ccc gac | | | | | | | | | | | | | | | | 528 |

-continued

| | | |
|---|---|---|
| Gly Ala Glu Gly Lys Leu Asp Glu Ser Gln Leu Leu Thr Asp Pro Asp<br>165 170 175 | | |
| gaa gcc gct gct ttt gtt gaa gcg acc aag gtc gat gca ctg gcc att<br>Glu Ala Ala Ala Phe Val Glu Ala Thr Lys Val Asp Ala Leu Ala Ile<br>180 185 190 | 576 | |
| gcc att ggc acc agt cat ggc gcc tat aaa ttc acg cgc cca cct tca<br>Ala Ile Gly Thr Ser His Gly Ala Tyr Lys Phe Thr Arg Pro Pro Ser<br>195 200 205 | 624 | |
| gct gat acg ctg tcg att gaa cgt atc cgg gaa att cat gcc aaa atc<br>Ala Asp Thr Leu Ser Ile Glu Arg Ile Arg Glu Ile His Ala Lys Ile<br>210 215 220 | 672 | |
| cct aac acg cac ttg gtg atg cat ggt tct tcg agt gtg ccg caa tcc<br>Pro Asn Thr His Leu Val Met His Gly Ser Ser Ser Val Pro Gln Ser<br>225 230 235 240 | 720 | |
| ttg ctg gaa caa atc agg cac tat ggc ggc aat atc aag gaa act tac<br>Leu Leu Glu Gln Ile Arg His Tyr Gly Gly Asn Ile Lys Glu Thr Tyr<br>245 250 255 | 768 | |
| ggt gtt ccg gtt tcg caa att gtc gaa ggg att aaa aac ggc gtg cgt<br>Gly Val Pro Val Ser Gln Ile Val Glu Gly Ile Lys Asn Gly Val Arg<br>260 265 270 | 816 | |
| aag gtc aat att gat acc gat atc cgc ctg gcc atg acc gct gct atc<br>Lys Val Asn Ile Asp Thr Asp Ile Arg Leu Ala Met Thr Ala Ala Ile<br>275 280 285 | 864 | |
| cgt gcg cat ttg gcg gag tat cca gag caa ttt gat ccg cga caa tat<br>Arg Ala His Leu Ala Glu Tyr Pro Glu Gln Phe Asp Pro Arg Gln Tyr<br>290 295 300 | 912 | |
| ttt aaa gaa gct act att gca gcc cag cat ttg tgt aaa gaa cgc ttc<br>Phe Lys Glu Ala Thr Ile Ala Ala Gln His Leu Cys Lys Glu Arg Phe<br>305 310 315 320 | 960 | |
| gag gcc ttt ggt agt gcc gga caa gcg agt aag ata aag gtt gtt cca<br>Glu Ala Phe Gly Ser Ala Gly Gln Ala Ser Lys Ile Lys Val Val Pro<br>325 330 335 | 1008 | |
| ctt gaa aaa atg gca gcc atc tac taa<br>Leu Glu Lys Met Ala Ala Ile Tyr<br>340 | 1035 | |

<210> SEQ ID NO 22
<211> LENGTH: 344
<212> TYPE: PRT
<213> ORGANISM: Methylophilus methylotrophus

<400> SEQUENCE: 22

Met Ala Leu Ile Ser Leu Arg Gln Leu Leu Asp His Ala Ala Glu His
1               5                   10                  15

Ser Tyr Gly Tyr Pro Ala Phe Asn Ile Asn Asn Met Glu Gln Ile Leu
            20                  25                  30

Ser Ile Met Lys Ala Ala Asp Glu Val Asp Ser Ala Val Ile Leu Gln
        35                  40                  45

Ala Ser Ala Gly Ala Arg Gly Tyr Ala Gly Glu Ser Phe Leu Arg Lys
    50                  55                  60

Met Val Glu Ala Ala Ile Glu Gln Tyr Pro His Ile Pro Val Cys Met
65                  70                  75                  80

His Gln Asp His Gly Thr Ser Pro Lys Ile Cys Gln Met Ala Ile Arg
                85                  90                  95

Ser Gly Phe Ser Ser Val Met Met Asp Gly Ser Leu Lys Glu Asp His
            100                 105                 110

Lys Thr Pro Ala Ser Tyr Asp Tyr Asn Val Asp Val Thr Arg Arg Val
        115                 120                 125

```
Val Glu Phe Ala His Ala Val Gly Val Ser Val Glu Gly Glu Leu Gly
    130                 135                 140
Val Leu Gly Ser Leu Glu Thr Gly Met Ala Gly Glu Glu Asp Gly Val
145                 150                 155                 160
Gly Ala Glu Gly Lys Leu Asp Glu Ser Gln Leu Leu Thr Asp Pro Asp
                165                 170                 175
Glu Ala Ala Ala Phe Val Glu Ala Thr Lys Val Asp Ala Leu Ala Ile
            180                 185                 190
Ala Ile Gly Thr Ser His Gly Ala Tyr Lys Phe Thr Arg Pro Pro Ser
        195                 200                 205
Ala Asp Thr Leu Ser Ile Glu Arg Ile Arg Glu Ile His Ala Lys Ile
    210                 215                 220
Pro Asn Thr His Leu Val Met His Gly Ser Ser Val Pro Gln Ser
225                 230                 235                 240
Leu Leu Glu Gln Ile Arg His Tyr Gly Gly Asn Ile Lys Glu Thr Tyr
                245                 250                 255
Gly Val Pro Val Ser Gln Ile Val Glu Gly Ile Lys Asn Gly Val Arg
            260                 265                 270
Lys Val Asn Ile Asp Thr Asp Ile Arg Leu Ala Met Thr Ala Ala Ile
        275                 280                 285
Arg Ala His Leu Ala Glu Tyr Pro Glu Gln Phe Asp Pro Arg Gln Tyr
    290                 295                 300
Phe Lys Glu Ala Thr Ile Ala Ala Gln His Leu Cys Lys Glu Arg Phe
305                 310                 315                 320
Glu Ala Phe Gly Ser Ala Gly Gln Ala Ser Lys Ile Lys Val Val Pro
                325                 330                 335
Leu Glu Lys Met Ala Ala Ile Tyr
            340

<210> SEQ ID NO 23
<211> LENGTH: 795
<212> TYPE: DNA
<213> ORGANISM: Methylophilus methylotrophus
<220> FEATURE:
<221> NAME/KEY: CDS
<222> LOCATION: (1)..(795)
<223> OTHER INFORMATION:

<400> SEQUENCE: 23 atg tcc cgt tct gat aca acc ctt cct tcc cca cac aaa att gtg gtt     48
Met Ser Arg Ser Asp Thr Thr Leu Pro Ser Pro His Lys Ile Val Val
1               5                   10                  15 gcc aac tgg aaa atg cat ggc aat ctt gcc cgt aac cac acg ctt gtt     96
Ala Asn Trp Lys Met His Gly Asn Leu Ala Arg Asn His Thr Leu Val
            20                  25                  30 gat ggc tat ctg caa ggc ttg aaa tca ttg tcc caa gcc gat gtc gtt    144
Asp Gly Tyr Leu Gln Gly Leu Lys Ser Leu Ser Gln Ala Asp Val Val
        35                  40                  45 atc tgt gtg cct tat cct tat ctg gcg caa ata cag tct ttg ttg tct    192
Ile Cys Val Pro Tyr Pro Tyr Leu Ala Gln Ile Gln Ser Leu Leu Ser
    50                  55                  60 gag act cac gtc gcc tgg ggt gcg cag aat ctt gcc aag tac gag gaa    240
Glu Thr His Val Ala Trp Gly Ala Gln Asn Leu Ala Lys Tyr Glu Glu
65                  70                  75                  80 ggt gct tat acc ggt gag gtg agc gcg ggg atg ttg tgc gat ttt ggg    288
Gly Ala Tyr Thr Gly Glu Val Ser Ala Gly Met Leu Cys Asp Phe Gly
                85                  90                  95 gcg caa tat gtg att atc ggc cac tcc gag cga agt act gct tat tgc    336
```

-continued

```
              Ala Gln Tyr Val Ile Ile Gly His Ser Glu Arg Ser Thr Ala Tyr Cys
                              100                 105                 110 gag tcg gat gaa aat att gcc gaa aaa ttc atg atg gcc aag cgg cat                    384
Glu Ser Asp Glu Asn Ile Ala Glu Lys Phe Met Met Ala Lys Arg His
            115                 120                 125 ggg tta acg cca att ctg tgt gtt gga gag acc ttg ctt gaa cgc gag                    432
Gly Leu Thr Pro Ile Leu Cys Val Gly Glu Thr Leu Leu Glu Arg Glu
        130                 135                 140 gct ggt gtc atg gag cgt gtt gtc ggt aaa caa ctg gaa acc att att                    480
Ala Gly Val Met Glu Arg Val Val Gly Lys Gln Leu Glu Thr Ile Ile
145                 150                 155                 160 cgt ctg ttt ggc gga gag gcc ttc gca aat agc atc gtt tca tat gag                    528
Arg Leu Phe Gly Gly Glu Ala Phe Ala Asn Ser Ile Val Ser Tyr Glu
                165                 170                 175 ccg att tgg gca att gga acc ggc ctt gca gct tca gca gag cag gcg                    576
Pro Ile Trp Ala Ile Gly Thr Gly Leu Ala Ala Ser Ala Glu Gln Ala
            180                 185                 190 gtg gct atg cac cag ttt atc cgt gac acc gta tca gcc gca gat aag                    624
Val Ala Met His Gln Phe Ile Arg Asp Thr Val Ser Ala Ala Asp Lys
        195                 200                 205 agc gcc gcg gac acg cta aaa atc ctc tac ggg ggc agc gta aac ccg                    672
Ser Ala Ala Asp Thr Leu Lys Ile Leu Tyr Gly Gly Ser Val Asn Pro
210                 215                 220 caa aat gcg gta caa tta tta aat cag cag gaa att gat ggc gcg ctg                    720
Gln Asn Ala Val Gln Leu Leu Asn Gln Gln Glu Ile Asp Gly Ala Leu
225                 230                 235                 240 gtc ggc cgt tgc tcc ctc aat gcg gag caa ttt ata aaa atc tgt cag                    768
Val Gly Arg Cys Ser Leu Asn Ala Glu Gln Phe Ile Lys Ile Cys Gln
                245                 250                 255 gcc gtc cct gaa aat agc gtc gtc tag                                                795
Ala Val Pro Glu Asn Ser Val Val
            260

<210> SEQ ID NO 24
<211> LENGTH: 264
<212> TYPE: PRT
<213> ORGANISM: Methylophilus methylotrophus

<400> SEQUENCE: 24

Met Ser Arg Ser Asp Thr Thr Leu Pro Ser Pro His Lys Ile Val
1               5                   10                  15

Ala Asn Trp Lys Met His Gly Asn Leu Ala Arg Asn His Thr Leu Val
            20                  25                  30

Asp Gly Tyr Leu Gln Gly Leu Lys Ser Leu Ser Gln Ala Asp Val Val
        35                  40                  45

Ile Cys Val Pro Tyr Pro Tyr Leu Ala Gln Ile Gln Ser Leu Leu Ser
    50                  55                  60

Glu Thr His Val Ala Trp Gly Ala Gln Asn Leu Ala Lys Tyr Glu Glu
65                  70                  75                  80

Gly Ala Tyr Thr Gly Glu Val Ser Ala Gly Met Leu Cys Asp Phe Gly
                85                  90                  95

Ala Gln Tyr Val Ile Ile Gly His Ser Glu Arg Ser Thr Ala Tyr Cys
            100                 105                 110

Glu Ser Asp Glu Asn Ile Ala Glu Lys Phe Met Met Ala Lys Arg His
        115                 120                 125

Gly Leu Thr Pro Ile Leu Cys Val Gly Glu Thr Leu Leu Glu Arg Glu
    130                 135                 140

Ala Gly Val Met Glu Arg Val Val Gly Lys Gln Leu Glu Thr Ile Ile
```

```
                145                 150                 155                 160
Arg Leu Phe Gly Gly Glu Ala Phe Ala Asn Ser Ile Val Ser Tyr Glu
                    165                 170                 175

Pro Ile Trp Ala Ile Gly Thr Gly Leu Ala Ala Ser Ala Glu Gln Ala
            180                 185                 190

Val Ala Met His Gln Phe Ile Arg Asp Thr Val Ser Ala Ala Asp Lys
        195                 200                 205

Ser Ala Ala Asp Thr Leu Lys Ile Leu Tyr Gly Gly Ser Val Asn Pro
    210                 215                 220

Gln Asn Ala Val Gln Leu Leu Asn Gln Gln Glu Ile Asp Gly Ala Leu
225                 230                 235                 240

Val Gly Arg Cys Ser Leu Asn Ala Glu Gln Phe Ile Lys Ile Cys Gln
                    245                 250                 255

Ala Val Pro Glu Asn Ser Val Val
                260

<210> SEQ ID NO 25
<211> LENGTH: 783
<212> TYPE: DNA
<213> ORGANISM: Methylophilus methylotrophus
<220> FEATURE:
<221> NAME/KEY: CDS
<222> LOCATION: (1)..(783)
<223> OTHER INFORMATION:

<400> SEQUENCE: 25 atg aca aat cgc tcc aag ctg gtg gtt gcc aac cgc aaa atg cac ggc      48
Met Thr Asn Arg Ser Lys Leu Val Val Ala Asn Arg Lys Met His Gly
1               5                   10                  15 aac ttg cca gac aat cag cag ttt atg caa acg cta ttg caa caa acc      96
Asn Leu Pro Asp Asn Gln Gln Phe Met Gln Thr Leu Leu Gln Gln Thr
                20                  25                  30 cgc cat cat aag gca cgt tat gcg gta tgc ccg ccg cat ccg tac ctg     144
Arg His His Lys Ala Arg Tyr Ala Val Cys Pro Pro His Pro Tyr Leu
            35                  40                  45 ttc cag gca cag caa gtg ctg caa gac agc cat att gcc tgg ggt ggg     192
Phe Gln Ala Gln Gln Val Leu Gln Asp Ser His Ile Ala Trp Gly Gly
        50                  55                  60 caa aac atg agc cgc tat gaa aaa ggc gcc tat acg ggc tcg gtc tca     240
Gln Asn Met Ser Arg Tyr Glu Lys Gly Ala Tyr Thr Gly Ser Val Ser
65                  70                  75                  80 ccg ctc atg ctc aag gag ttt ggc tgc agc tat gtg att atc ggt cac     288
Pro Leu Met Leu Lys Glu Phe Gly Cys Ser Tyr Val Ile Ile Gly His
                    85                  90                  95 tca gaa cgg cgt caa cgc ggt cac gat agt gat gaa acc tgc gga gaa     336
Ser Glu Arg Arg Gln Arg Gly His Asp Ser Asp Glu Thr Cys Gly Glu
                100                 105                 110 cgt ttt gaa gcc gcg ctc aag gcc ggc ctc acg ccc att ttg tgc atc     384
Arg Phe Glu Ala Ala Leu Lys Ala Gly Leu Thr Pro Ile Leu Cys Ile
            115                 120                 125 ggt gaa acc ttg gaa gaa tac gag caa ggc gaa act gac ctt gtc gtg     432
Gly Glu Thr Leu Glu Glu Tyr Glu Gln Gly Glu Thr Asp Leu Val Val
        130                 135                 140 gta cgg caa ctc aac ccg gtg att gcg cat gtc ggc atc gag gcg cta     480
Val Arg Gln Leu Asn Pro Val Ile Ala His Val Gly Ile Glu Ala Leu
145                 150                 155                 160 tca aaa ggc gtg att gcc tat gag cca gtg tgg gcc ata ggt aca ggc     528
Ser Lys Gly Val Ile Ala Tyr Glu Pro Val Trp Ala Ile Gly Thr Gly
                    165                 170                 175
```

```
aga gca gcc act cca cag cat gca caa gcc att ttg tct ttt atc cgt     576
Arg Ala Ala Thr Pro Gln His Ala Gln Ala Ile Leu Ser Phe Ile Arg
            180                 185                 190 ggc cat att gaa tta ctg gac aca aaa gcc gcc gag gac att acc ttg     624
Gly His Ile Glu Leu Leu Asp Thr Lys Ala Ala Glu Asp Ile Thr Leu
        195                 200                 205 ctg tat ggt ggc agt atg aat cct ggc aat gcc gca caa cta ttg agc     672
Leu Tyr Gly Gly Ser Met Asn Pro Gly Asn Ala Ala Gln Leu Leu Ser
    210                 215                 220 atg ccc gat gta gat ggc ggc ctg atc ggc ggc gcc tcc ctg gta gca     720
Met Pro Asp Val Asp Gly Gly Leu Ile Gly Gly Ala Ser Leu Val Ala
225                 230                 235                 240 gac gac ttt atc cgc atc tgc cag att gcc aac gaa ttg acc ccg ctc     768
Asp Asp Phe Ile Arg Ile Cys Gln Ile Ala Asn Glu Leu Thr Pro Leu
                245                 250                 255 aaa acc gca gcc tga                                                  783
Lys Thr Ala Ala
            260

<210> SEQ ID NO 26
<211> LENGTH: 260
<212> TYPE: PRT
<213> ORGANISM: Methylophilus methylotrophus

<400> SEQUENCE: 26

Met Thr Asn Arg Ser Lys Leu Val Val Ala Asn Arg Lys Met His Gly
1               5                   10                  15

Asn Leu Pro Asp Asn Gln Gln Phe Met Gln Thr Leu Leu Gln Gln Thr
            20                  25                  30

Arg His His Lys Ala Arg Tyr Ala Val Cys Pro Pro His Pro Tyr Leu
        35                  40                  45

Phe Gln Ala Gln Gln Val Leu Gln Asp Ser His Ile Ala Trp Gly Gly
    50                  55                  60

Gln Asn Met Ser Arg Tyr Glu Lys Gly Ala Tyr Thr Gly Ser Val Ser
65                  70                  75                  80

Pro Leu Met Leu Lys Glu Phe Gly Cys Ser Tyr Val Ile Ile Gly His
                85                  90                  95

Ser Glu Arg Arg Gln Arg Gly His Asp Ser Asp Glu Thr Cys Gly Glu
            100                 105                 110

Arg Phe Glu Ala Ala Leu Lys Ala Gly Leu Thr Pro Ile Leu Cys Ile
        115                 120                 125

Gly Glu Thr Leu Glu Glu Tyr Glu Gln Gly Glu Thr Asp Leu Val Val
    130                 135                 140

Val Arg Gln Leu Asn Pro Val Ile Ala His Val Gly Ile Glu Ala Leu
145                 150                 155                 160

Ser Lys Gly Val Ile Ala Tyr Glu Pro Val Trp Ala Ile Gly Thr Gly
                165                 170                 175

Arg Ala Ala Thr Pro Gln His Ala Gln Ala Ile Leu Ser Phe Ile Arg
            180                 185                 190

Gly His Ile Glu Leu Leu Asp Thr Lys Ala Ala Glu Asp Ile Thr Leu
        195                 200                 205

Leu Tyr Gly Gly Ser Met Asn Pro Gly Asn Ala Ala Gln Leu Leu Ser
    210                 215                 220

Met Pro Asp Val Asp Gly Gly Leu Ile Gly Gly Ala Ser Leu Val Ala
225                 230                 235                 240

Asp Asp Phe Ile Arg Ile Cys Gln Ile Ala Asn Glu Leu Thr Pro Leu
                245                 250                 255
```

```
Lys Thr Ala Ala
        260
```

<210> SEQ ID NO 27
<211> LENGTH: 825
<212> TYPE: DNA
<213> ORGANISM: Methylophilus methylotrophus
<220> FEATURE:
<221> NAME/KEY: CDS
<222> LOCATION: (1)..(825)
<223> OTHER INFORMATION:

<400> SEQUENCE: 27

```
atg cga caa aaa tta gtc att ggt aac tgg aag ctg cat ggc ggc ctg      48
Met Arg Gln Lys Leu Val Ile Gly Asn Trp Lys Leu His Gly Gly Leu
1               5                   10                  15 ctt gaa aat cag ggc ctg ttg aat cgt ctc aag caa gag ttg cac gat      96
Leu Glu Asn Gln Gly Leu Leu Asn Arg Leu Lys Gln Glu Leu His Asp
            20                  25                  30 cta cct ggc gtg gat gcc gcg gtg tgt tta ccc tat gta tac ctg ttc     144
Leu Pro Gly Val Asp Ala Ala Val Cys Leu Pro Tyr Val Tyr Leu Phe
        35                  40                  45 cag gca caa acc ctg cta caa gat tcc cat att gcc tgg ggc gcc caa     192
Gln Ala Gln Thr Leu Leu Gln Asp Ser His Ile Ala Trp Gly Ala Gln
    50                  55                  60 aac gtc agt caa ttc acc gaa ggt gcg ttt acc tcc tgc att tca gcc     240
Asn Val Ser Gln Phe Thr Glu Gly Ala Phe Thr Ser Cys Ile Ser Ala
65                  70                  75                  80 aaa atg gta gcc gaa ttt ggc tgc acc tat acc atc att ggc cat tct     288
Lys Met Val Ala Glu Phe Gly Cys Thr Tyr Thr Ile Ile Gly His Ser
                85                  90                  95 gag cgt cgc gcc ctc aag ctc gaa agt aac cag gtc gcc acc aaa cgc     336
Glu Arg Arg Ala Leu Lys Leu Glu Ser Asn Gln Val Ala Thr Lys Arg
            100                 105                 110 ctg ctt aat gcc ctg cat gcc ggg ctc acg cct att ttc tgt gtc ggt     384
Leu Leu Asn Ala Leu His Ala Gly Leu Thr Pro Ile Phe Cys Val Gly
        115                 120                 125 gaa acg cag gat gaa cgc gat ggc aat atg gct gag ctg att gtg cgc     432
Glu Thr Gln Asp Glu Arg Asp Gly Asn Met Ala Glu Leu Ile Val Arg
    130                 135                 140 aac cag atg ctg aat gtc gtc tac ggt ctg gat gat gaa gcg ttt gcc     480
Asn Gln Met Leu Asn Val Val Tyr Gly Leu Asp Asp Glu Ala Phe Ala
145                 150                 155                 160 ctt gcc aaa aaa ttt aat atg gtg att gcc tat gaa ccg gta tgg gcc     528
Leu Ala Lys Lys Phe Asn Met Val Ile Ala Tyr Glu Pro Val Trp Ala
                165                 170                 175 att ggt acg ggc gag cat gcc agc ccg gaa cag gcg caa cgc atg cat     576
Ile Gly Thr Gly Glu His Ala Ser Pro Glu Gln Ala Gln Arg Met His
            180                 185                 190 gcc ttt atc cgc atg atg att gcc gag cgc gac cgc gag ttt gca gat     624
Ala Phe Ile Arg Met Met Ile Ala Glu Arg Asp Arg Glu Phe Ala Asp
        195                 200                 205 cgc atc cgt att gtc tat ggt ggc agt atg acc cca aaa aac gcg cac     672
Arg Ile Arg Ile Val Tyr Gly Gly Ser Met Thr Pro Lys Asn Ala His
    210                 215                 220 agc ctg ctc agc atg ccg gat atc gat ggt ggt ttg ctg ggc cgc gca     720
Ser Leu Leu Ser Met Pro Asp Ile Asp Gly Gly Leu Leu Gly Arg Ala
225                 230                 235                 240 gcc ttg gtg gca gaa gat ttt gtt gaa atc tgc aga att tcc agc cgt     768
Ala Leu Val Ala Glu Asp Phe Val Glu Ile Cys Arg Ile Ser Ser Arg
                245                 250                 255
```

```
tgc tac atg caa aaa aca gcg ttc agg gaa ccc tcg ccc gtc atg cca         816
Cys Tyr Met Gln Lys Thr Ala Phe Arg Glu Pro Ser Pro Val Met Pro
        260                 265                 270 gtc att tga                                                              825
Val Ile
```

<210> SEQ ID NO 28
<211> LENGTH: 274
<212> TYPE: PRT
<213> ORGANISM: Methylophilus methylotrophus

<400> SEQUENCE: 28

```
Met Arg Gln Lys Leu Val Ile Gly Asn Trp Lys Leu His Gly Gly Leu
1               5                   10                  15

Leu Glu Asn Gln Gly Leu Leu Asn Arg Leu Lys Gln Glu Leu His Asp
            20                  25                  30

Leu Pro Gly Val Asp Ala Ala Val Cys Leu Pro Tyr Val Tyr Leu Phe
        35                  40                  45

Gln Ala Gln Thr Leu Leu Gln Asp Ser His Ile Ala Trp Gly Ala Gln
    50                  55                  60

Asn Val Ser Gln Phe Thr Glu Gly Ala Phe Thr Ser Cys Ile Ser Ala
65                  70                  75                  80

Lys Met Val Ala Glu Phe Gly Cys Thr Tyr Thr Ile Ile Gly His Ser
                85                  90                  95

Glu Arg Arg Ala Leu Lys Leu Glu Ser Asn Gln Val Ala Thr Lys Arg
            100                 105                 110

Leu Leu Asn Ala Leu His Ala Gly Leu Thr Pro Ile Phe Cys Val Gly
        115                 120                 125

Glu Thr Gln Asp Glu Arg Asp Gly Asn Met Ala Glu Leu Ile Val Arg
    130                 135                 140

Asn Gln Met Leu Asn Val Val Tyr Gly Leu Asp Asp Glu Ala Phe Ala
145                 150                 155                 160

Leu Ala Lys Lys Phe Asn Met Val Ile Ala Tyr Glu Pro Val Trp Ala
                165                 170                 175

Ile Gly Thr Gly Glu His Ala Ser Pro Glu Gln Ala Gln Arg Met His
            180                 185                 190

Ala Phe Ile Arg Met Met Ile Ala Glu Arg Asp Arg Glu Phe Ala Asp
        195                 200                 205

Arg Ile Arg Ile Val Tyr Gly Gly Ser Met Thr Pro Lys Asn Ala His
    210                 215                 220

Ser Leu Leu Ser Met Pro Asp Ile Asp Gly Gly Leu Leu Gly Arg Ala
225                 230                 235                 240

Ala Leu Val Ala Glu Asp Phe Val Glu Ile Cys Arg Ile Ser Ser Arg
                245                 250                 255

Cys Tyr Met Gln Lys Thr Ala Phe Arg Glu Pro Ser Pro Val Met Pro
            260                 265                 270

Val Ile
```

<210> SEQ ID NO 29
<211> LENGTH: 1002
<212> TYPE: DNA
<213> ORGANISM: Methylophilus methylotrophus
<220> FEATURE:
<221> NAME/KEY: CDS
<222> LOCATION: (1)..(1002)
<223> OTHER INFORMATION:

<400> SEQUENCE: 29

```
atg tca gtc aag gta ggc att aac ggg ttt gga cga att ggc cgt atg      48
Met Ser Val Lys Val Gly Ile Asn Gly Phe Gly Arg Ile Gly Arg Met
1               5                  10                  15 gcg tta cgt gcg gcg att gag caa gca gag ttc agc aat atc gaa gtg      96
Ala Leu Arg Ala Ala Ile Glu Gln Ala Glu Phe Ser Asn Ile Glu Val
            20                  25                  30 gtc gct att aat agc tca tat gat gtt gaa tac atg atg tat ttg ctt     144
Val Ala Ile Asn Ser Ser Tyr Asp Val Glu Tyr Met Met Tyr Leu Leu
        35                  40                  45 aaa tat gac tct gtg cat ggc cgt ttt aat gct aag gtt gaa gct gac     192
Lys Tyr Asp Ser Val His Gly Arg Phe Asn Ala Lys Val Glu Ala Asp
    50                  55                  60 aat ggt gcg ctg gtg gtg aat ggc aag cgt atc cat tta acg gca gag     240
Asn Gly Ala Leu Val Val Asn Gly Lys Arg Ile His Leu Thr Ala Glu
65                  70                  75                  80 cga gat cca aac aat att gac tgg cgt aaa gga ggg gct gag gtg gtg     288
Arg Asp Pro Asn Asn Ile Asp Trp Arg Lys Gly Gly Ala Glu Val Val
                85                  90                  95 att gaa tct acc ggt gcc ttt tta acg cag gac aac tgc cag ccg cac     336
Ile Glu Ser Thr Gly Ala Phe Leu Thr Gln Asp Asn Cys Gln Pro His
            100                 105                 110 ctc aac ggt ggt gcc atc aaa gtg gtg cag tct gca ccc ggc aaa gac     384
Leu Asn Gly Gly Ala Ile Lys Val Val Gln Ser Ala Pro Gly Lys Asp
        115                 120                 125 gat acg ccg atg ttt gtc tat ggc gtg aac cac acc gaa tat gct ggc     432
Asp Thr Pro Met Phe Val Tyr Gly Val Asn His Thr Glu Tyr Ala Gly
    130                 135                 140 cag gca att att tca gca gca tct tgc act act aac ggg ttg gca ccc     480
Gln Ala Ile Ile Ser Ala Ala Ser Cys Thr Thr Asn Gly Leu Ala Pro
145                 150                 155                 160 ctg gca aaa gtg ttg cat gat acc ttt ggt gtc aag cgc ggc ctg atg     528
Leu Ala Lys Val Leu His Asp Thr Phe Gly Val Lys Arg Gly Leu Met
                165                 170                 175 acc acg att cat gct gcc acg gca tcc caa ctg acc gta gat ggc acc     576
Thr Thr Ile His Ala Ala Thr Ala Ser Gln Leu Thr Val Asp Gly Thr
            180                 185                 190 tcc aaa aaa gac tgg cgc ggc gga cgc agt gtc ttt gaa aac att att     624
Ser Lys Lys Asp Trp Arg Gly Gly Arg Ser Val Phe Glu Asn Ile Ile
        195                 200                 205 cct tcg agt acg ggt gca gcc aag gca gtg ggt aag gta atc ccg gcc     672
Pro Ser Ser Thr Gly Ala Ala Lys Ala Val Gly Lys Val Ile Pro Ala
    210                 215                 220 ttg aac aag aag tta aca ggg atg tcc atg cgc gtg cct tct gcg gat     720
Leu Asn Lys Lys Leu Thr Gly Met Ser Met Arg Val Pro Ser Ala Asp
225                 230                 235                 240 gtg tcg gtg gtt gac ctg acc gtg gaa ctt aat agc gag gct act tat     768
Val Ser Val Val Asp Leu Thr Val Glu Leu Asn Ser Glu Ala Thr Tyr
                245                 250                 255 gag gcg att tgc aca gcc atg caa caa gcg gcc gat ggc ccg cta aaa     816
Glu Ala Ile Cys Thr Ala Met Gln Gln Ala Ala Asp Gly Pro Leu Lys
            260                 265                 270 ggc gtg ctg gag tat acc aat gac aaa gtc gtt tcc agt gac ttc cgc     864
Gly Val Leu Glu Tyr Thr Asn Asp Lys Val Val Ser Ser Asp Phe Arg
        275                 280                 285 agc agc cct gct gcc agc gtg ttt gat gca gat gcc ggt atc atg ctc     912
Ser Ser Pro Ala Ala Ser Val Phe Asp Ala Asp Ala Gly Ile Met Leu
    290                 295                 300 gac ccg act ttt gtt aaa gtg gtt ggc tgg tac gac aac gag tac ggt     960
Asp Pro Thr Phe Val Lys Val Val Gly Trp Tyr Asp Asn Glu Tyr Gly
```

```
Asp Pro Thr Phe Val Lys Val Val Gly Trp Tyr Asp Asn Glu Tyr Gly
305                 310                 315                 320 tat acc tgt aac ctg ctg cgc ctg gtt caa cac att gct taa            1002
Tyr Thr Cys Asn Leu Leu Arg Leu Val Gln His Ile Ala
                325                 330
```

<210> SEQ ID NO 30
<211> LENGTH: 333
<212> TYPE: PRT
<213> ORGANISM: Methylophilus methylotrophus

<400> SEQUENCE: 30

```
Met Ser Val Lys Val Gly Ile Asn Gly Phe Gly Arg Ile Gly Arg Met
1               5                   10                  15

Ala Leu Arg Ala Ala Ile Glu Gln Ala Glu Phe Ser Asn Ile Glu Val
                20                  25                  30

Val Ala Ile Asn Ser Ser Tyr Asp Val Glu Tyr Met Met Tyr Leu Leu
            35                  40                  45

Lys Tyr Asp Ser Val His Gly Arg Phe Asn Ala Lys Val Glu Ala Asp
        50                  55                  60

Asn Gly Ala Leu Val Val Asn Gly Lys Arg Ile His Leu Thr Ala Glu
65                  70                  75                  80

Arg Asp Pro Asn Asn Ile Asp Trp Arg Lys Gly Gly Ala Glu Val Val
                85                  90                  95

Ile Glu Ser Thr Gly Ala Phe Leu Thr Gln Asp Asn Cys Gln Pro His
            100                 105                 110

Leu Asn Gly Gly Ala Ile Lys Val Val Gln Ser Ala Pro Gly Lys Asp
        115                 120                 125

Asp Thr Pro Met Phe Val Tyr Gly Val Asn His Thr Glu Tyr Ala Gly
    130                 135                 140

Gln Ala Ile Ile Ser Ala Ala Ser Cys Thr Thr Asn Gly Leu Ala Pro
145                 150                 155                 160

Leu Ala Lys Val Leu His Asp Thr Phe Gly Val Lys Arg Gly Leu Met
                165                 170                 175

Thr Thr Ile His Ala Ala Thr Ala Ser Gln Leu Thr Val Asp Gly Thr
            180                 185                 190

Ser Lys Lys Asp Trp Arg Gly Gly Arg Ser Val Phe Glu Asn Ile Ile
        195                 200                 205

Pro Ser Ser Thr Gly Ala Ala Lys Ala Val Gly Lys Val Ile Pro Ala
    210                 215                 220

Leu Asn Lys Lys Leu Thr Gly Met Ser Met Arg Val Pro Ser Ala Asp
225                 230                 235                 240

Val Ser Val Val Asp Leu Thr Val Glu Leu Asn Ser Glu Ala Thr Tyr
                245                 250                 255

Glu Ala Ile Cys Thr Ala Met Gln Gln Ala Ala Asp Gly Pro Leu Lys
            260                 265                 270

Gly Val Leu Glu Tyr Thr Asn Asp Lys Val Val Ser Ser Asp Phe Arg
        275                 280                 285

Ser Ser Pro Ala Ala Ser Val Phe Asp Ala Asp Ala Gly Ile Met Leu
    290                 295                 300

Asp Pro Thr Phe Val Lys Val Val Gly Trp Tyr Asp Asn Glu Tyr Gly
305                 310                 315                 320

Tyr Thr Cys Asn Leu Leu Arg Leu Val Gln His Ile Ala
                325                 330
```

```
<210> SEQ ID NO 31
<211> LENGTH: 1062
<212> TYPE: DNA
<213> ORGANISM: Methylophilus methylotrophus
<220> FEATURE:
<221> NAME/KEY: CDS
<222> LOCATION: (1)..(1062)
<223> OTHER INFORMATION:

<400> SEQUENCE: 31 atg ggc att aga gtg ggc att aac ggg ttt ggc cgt att ggc cgg atg      48
Met Gly Ile Arg Val Gly Ile Asn Gly Phe Gly Arg Ile Gly Arg Met
1               5                   10                  15 gtg ctg cgc gcc gca tta aat cag gca gag ttc aag gat atc gag gtt      96
Val Leu Arg Ala Ala Leu Asn Gln Ala Glu Phe Lys Asp Ile Glu Val
                20                  25                  30 gtt gcc att aac ggc atc gaa gaa cct gaa cat atg ctg tat atg ctc     144
Val Ala Ile Asn Gly Ile Glu Glu Pro Glu His Met Leu Tyr Met Leu
            35                  40                  45 aaa tat gac tct gtg cac gga aga ctg gca cag gaa gct cat tta gag     192
Lys Tyr Asp Ser Val His Gly Arg Leu Ala Gln Glu Ala His Leu Glu
        50                  55                  60 ggc ggt ttc ctg gtg att gat ggt aaa aaa atc cgt ctc act gca cat     240
Gly Gly Phe Leu Val Ile Asp Gly Lys Lys Ile Arg Leu Thr Ala His
65              70                  75                  80 gcc aaa ccg gca gac att gac tgg cgg tct gag cat gtc gat gtc gtg     288
Ala Lys Pro Ala Asp Ile Asp Trp Arg Ser Glu His Val Asp Val Val
                85                  90                  95 gtg gaa tgt acg ggt gtt ttc ctg acc cag gaa agc tgt gct gcc cat     336
Val Glu Cys Thr Gly Val Phe Leu Thr Gln Glu Ser Cys Ala Ala His
                100                 105                 110 att gca ggt ggt gca cgt atc gta gtc cag tcc gcg cct ggc aaa gac     384
Ile Ala Gly Gly Ala Arg Ile Val Val Gln Ser Ala Pro Gly Lys Asp
            115                 120                 125 gat acg cca atg ttt gtc tat ggt gtc aat cat tac cac tac cgc gga     432
Asp Thr Pro Met Phe Val Tyr Gly Val Asn His Tyr His Tyr Arg Gly
        130                 135                 140 gaa gat att gtc tcg gca gcg tct tgt acg act aat ggc ttg gcg ccc     480
Glu Asp Ile Val Ser Ala Ala Ser Cys Thr Thr Asn Gly Leu Ala Pro
145                 150                 155                 160 att gtt aag gtg tta cat gac aat ttt ggg gtc aag cgt ggc ttg atg     528
Ile Val Lys Val Leu His Asp Asn Phe Gly Val Lys Arg Gly Leu Met
                165                 170                 175 act acc ata cac gca gcg act gcc acc cag aaa acg gtt gat ggt act     576
Thr Thr Ile His Ala Ala Thr Ala Thr Gln Lys Thr Val Asp Gly Thr
                180                 185                 190 tct aac aaa gac tgg cgt ggc ggt cga ggt gtt ttc gat aac att att     624
Ser Asn Lys Asp Trp Arg Gly Gly Arg Gly Val Phe Asp Asn Ile Ile
            195                 200                 205 cct tcc agc act ggt gcg gcc aag gcg gtt ggt aaa gta atc ccg gca     672
Pro Ser Ser Thr Gly Ala Ala Lys Ala Val Gly Lys Val Ile Pro Ala
        210                 215                 220 ctt aac aaa aaa ctc acc ggg atg tcc atg cgt att cct tcc gcg gat     720
Leu Asn Lys Lys Leu Thr Gly Met Ser Met Arg Ile Pro Ser Ala Asp
225                 230                 235                 240 gtg tct gtg gtt gat tta acg gta gag ttg caa cag agc acc act tat     768
Val Ser Val Val Asp Leu Thr Val Glu Leu Gln Gln Ser Thr Thr Tyr
                245                 250                 255 gaa gaa att tgc gcc gtc atg caa tat gca gcc gag cgc gac ctg aaa     816
Glu Glu Ile Cys Ala Val Met Gln Tyr Ala Ala Glu Arg Asp Leu Lys
                260                 265                 270
```

-continued

```
ggc gtg cta ggc tat acc gat gaa gcc gtc gtt tcc agt gat ttt agg      864
Gly Val Leu Gly Tyr Thr Asp Glu Ala Val Val Ser Ser Asp Phe Arg
        275                 280                 285 ggt tat ccg gcc gcc agt gtg ttt gat gcc agt gca ggc atc atg ctg      912
Gly Tyr Pro Ala Ala Ser Val Phe Asp Ala Ser Ala Gly Ile Met Leu
    290                 295                 300 gac ccc acc ttt gtc aag ctg ata ggc tgg tat gac aac gag tat ggc      960
Asp Pro Thr Phe Val Lys Leu Ile Gly Trp Tyr Asp Asn Glu Tyr Gly
305                 310                 315                 320 tat acc tgc aat ctg ttg cgc tta acg cgt tat gtc ggt tat gcc aag     1008
Tyr Thr Cys Asn Leu Leu Arg Leu Thr Arg Tyr Val Gly Tyr Ala Lys
                325                 330                 335 ctg tcg atg acg gat ttg ccg caa act gag cag caa gag gcc gtt gcc     1056
Leu Ser Met Thr Asp Leu Pro Gln Thr Glu Gln Gln Glu Ala Val Ala
            340                 345                 350 gct tga                                                              1062
Ala
```

<210> SEQ ID NO 32
<211> LENGTH: 353
<212> TYPE: PRT
<213> ORGANISM: Methylophilus methylotrophus

<400> SEQUENCE: 32

```
Met Gly Ile Arg Val Gly Ile Asn Gly Phe Gly Arg Ile Gly Arg Met
1               5                  10                  15

Val Leu Arg Ala Ala Leu Asn Gln Ala Glu Phe Lys Asp Ile Glu Val
            20                  25                  30

Val Ala Ile Asn Gly Ile Glu Glu Pro Glu His Met Leu Tyr Met Leu
        35                  40                  45

Lys Tyr Asp Ser Val His Gly Arg Leu Ala Gln Glu Ala His Leu Glu
    50                  55                  60

Gly Gly Phe Leu Val Ile Asp Gly Lys Lys Ile Arg Leu Thr Ala His
65                  70                  75                  80

Ala Lys Pro Ala Asp Ile Asp Trp Arg Ser Glu His Val Asp Val Val
                85                  90                  95

Val Glu Cys Thr Gly Val Phe Leu Thr Gln Glu Ser Cys Ala Ala His
            100                 105                 110

Ile Ala Gly Gly Ala Arg Ile Val Val Gln Ser Ala Pro Gly Lys Asp
        115                 120                 125

Asp Thr Pro Met Phe Val Tyr Gly Val Asn His Tyr His Tyr Arg Gly
    130                 135                 140

Glu Asp Ile Val Ser Ala Ala Ser Cys Thr Thr Asn Gly Leu Ala Pro
145                 150                 155                 160

Ile Val Lys Val Leu His Asp Asn Phe Gly Val Lys Arg Gly Leu Met
                165                 170                 175

Thr Thr Ile His Ala Ala Thr Ala Thr Gln Lys Thr Val Asp Gly Thr
            180                 185                 190

Ser Asn Lys Asp Trp Arg Gly Gly Arg Gly Val Phe Asp Asn Ile Ile
        195                 200                 205

Pro Ser Ser Thr Gly Ala Ala Lys Ala Val Gly Lys Val Ile Pro Ala
    210                 215                 220

Leu Asn Lys Lys Leu Thr Gly Met Ser Met Arg Ile Pro Ser Ala Asp
225                 230                 235                 240

Val Ser Val Val Asp Leu Thr Val Glu Leu Gln Gln Ser Thr Thr Tyr
                245                 250                 255
```

```
Glu Glu Ile Cys Ala Val Met Gln Tyr Ala Ala Glu Arg Asp Leu Lys
            260                 265                 270

Gly Val Leu Gly Tyr Thr Asp Glu Ala Val Val Ser Ser Asp Phe Arg
            275                 280                 285

Gly Tyr Pro Ala Ala Ser Val Phe Asp Ala Ser Ala Gly Ile Met Leu
            290                 295                 300

Asp Pro Thr Phe Val Lys Leu Ile Gly Trp Tyr Asp Asn Glu Tyr Gly
305                 310                 315                 320

Tyr Thr Cys Asn Leu Leu Arg Leu Thr Arg Tyr Val Gly Tyr Ala Lys
                325                 330                 335

Leu Ser Met Thr Asp Leu Pro Gln Thr Glu Gln Gln Glu Ala Val Ala
            340                 345                 350

Ala

<210> SEQ ID NO 33
<211> LENGTH: 1194
<212> TYPE: DNA
<213> ORGANISM: Methylophilus methylotrophus
<220> FEATURE:
<221> NAME/KEY: CDS
<222> LOCATION: (1)..(1194)
<223> OTHER INFORMATION:

<400> SEQUENCE: 33 atg aaa ttt atc aaa atg act gac ctc gac ttg cgt ggt aaa cgt gtg      48
Met Lys Phe Ile Lys Met Thr Asp Leu Asp Leu Arg Gly Lys Arg Val
1               5                   10                  15 ttc atc cgc gcc gac ctc aat gtg ccg gta aaa gat ggc gtg gtg acc      96
Phe Ile Arg Ala Asp Leu Asn Val Pro Val Lys Asp Gly Val Val Thr
                20                  25                  30 agt gat gcc aga att gta gcc agc atg ccc acc att gaa tac gcc ttg     144
Ser Asp Ala Arg Ile Val Ala Ser Met Pro Thr Ile Glu Tyr Ala Leu
            35                  40                  45 aaa gcg ggc gct aaa gtc atg gtg act tcg cat ctt ggc cgc cca gaa     192
Lys Ala Gly Ala Lys Val Met Val Thr Ser His Leu Gly Arg Pro Glu
        50                  55                  60 gaa ggc gtt tac agt gaa gaa aac tca ttg agg cca gtg gcg gat gta     240
Glu Gly Val Tyr Ser Glu Glu Asn Ser Leu Arg Pro Val Ala Asp Val
65                  70                  75                  80 atg agc aag ctg ctg ggg cag cca gta cgc ctg gtg aaa aac tgg ctg     288
Met Ser Lys Leu Leu Gly Gln Pro Val Arg Leu Val Lys Asn Trp Leu
                85                  90                  95 gcc ccc aat gcg cct gaa gac agc ctg acc aca gca gat ggt cag ctc     336
Ala Pro Asn Ala Pro Glu Asp Ser Leu Thr Thr Ala Asp Gly Gln Leu
                100                 105                 110 att ttg ctg gaa aac tgc cgg ttt aat gta ggc gaa aag aaa aat aat     384
Ile Leu Leu Glu Asn Cys Arg Phe Asn Val Gly Glu Lys Lys Asn Asn
            115                 120                 125 gat gat ctg gcc aaa aaa tac gcc gcc ttg tgc gat gta ttt gtc atg     432
Asp Asp Leu Ala Lys Lys Tyr Ala Ala Leu Cys Asp Val Phe Val Met
        130                 135                 140 gat gct ttt ggc act gca cac cgc gca gaa gcc tct aca cat ggc att     480
Asp Ala Phe Gly Thr Ala His Arg Ala Glu Ala Ser Thr His Gly Ile
145                 150                 155                 160 gcc aaa ttt gcg cct gtg gcc tgt gcc gga att ctg ctc act gaa gag     528
Ala Lys Phe Ala Pro Val Ala Cys Ala Gly Ile Leu Leu Thr Glu Glu
                165                 170                 175 ctg gat gca ttg agc aaa gcc ttg ctg gcg ccc gcc cgc ccg ctg gta     576
Leu Asp Ala Leu Ser Lys Ala Leu Leu Ala Pro Ala Arg Pro Leu Val
                180                 185                 190
```

```
gcg att gtg ggg ggc tca aaa gtc tcg acc aaa ctg acc gtg ctt gaa    624
Ala Ile Val Gly Gly Ser Lys Val Ser Thr Lys Leu Thr Val Leu Glu
        195                 200                 205 agt ttg tct gac aaa gtg gat cag ttg gtg gta ggc ggt att gct        672
Ser Leu Ser Asp Lys Val Asp Gln Leu Val Val Gly Gly Ile Ala
210                 215                 220 aac acc ttc ctc aag gct tct ggt cag gaa gtc ggt aag tct ttg tgt    720
Asn Thr Phe Leu Lys Ala Ser Gly Gln Glu Val Gly Lys Ser Leu Cys
225                 230                 235                 240 gag gat gac ctg gtg gat acc gcg aag tgc ctg atg gat aaa atg gcg    768
Glu Asp Asp Leu Val Asp Thr Ala Lys Cys Leu Met Asp Lys Met Ala
                245                 250                 255 gcg cgt ggt gcc tgt gtg cct att gct aaa gat gtg gtg gtt ggc aag    816
Ala Arg Gly Ala Cys Val Pro Ile Ala Lys Asp Val Val Val Gly Lys
            260                 265                 270 cag ttt gat gcc aat gaa cct gct gtc aaa aaa tca gca aca gaa gtt    864
Gln Phe Asp Ala Asn Glu Pro Ala Val Lys Lys Ser Ala Thr Glu Val
        275                 280                 285 gcc gta gac gaa atg att ttt gat att ggg tca caa tca gca gct gag    912
Ala Val Asp Glu Met Ile Phe Asp Ile Gly Ser Gln Ser Ala Ala Glu
290                 295                 300 ctg gtg gac atc att atg aaa gct ggc act gtc gta tgg aat ggt ccg    960
Leu Val Asp Ile Ile Met Lys Ala Gly Thr Val Val Trp Asn Gly Pro
305                 310                 315                 320 gtg ggt gtg ttt gag ttt gac cag ttt ggt gaa ggt act aaa acc att    1008
Val Gly Val Phe Glu Phe Asp Gln Phe Gly Glu Gly Thr Lys Thr Ile
                325                 330                 335 gcc aag gcc atc gct gaa acc aag gcc ttt acg ctg gca ggt ggg ggt    1056
Ala Lys Ala Ile Ala Glu Thr Lys Ala Phe Thr Leu Ala Gly Gly Gly
            340                 345                 350 gac acc att gcg gcc atc cag aag tac gac att tat gac aag gta tct    1104
Asp Thr Ile Ala Ala Ile Gln Lys Tyr Asp Ile Tyr Asp Lys Val Ser
        355                 360                 365 tac atc tcg acg gct ggc ggg gct ttc ctg gag ttt ctc gaa ggc aag    1152
Tyr Ile Ser Thr Ala Gly Gly Ala Phe Leu Glu Phe Leu Glu Gly Lys
370                 375                 380 act ctg ccg gct gtg gct att ctg gaa gag cgc gcc cgt taa            1194
Thr Leu Pro Ala Val Ala Ile Leu Glu Glu Arg Ala Arg
385                 390                 395
```

<210> SEQ ID NO 34
<211> LENGTH: 397
<212> TYPE: PRT
<213> ORGANISM: Methylophilus methylotrophus

<400> SEQUENCE: 34

```
Met Lys Phe Ile Lys Met Thr Asp Leu Asp Leu Arg Gly Lys Arg Val
1               5                   10                  15

Phe Ile Arg Ala Asp Leu Asn Val Pro Val Lys Asp Gly Val Val Thr
                20                  25                  30

Ser Asp Ala Arg Ile Val Ala Ser Met Pro Thr Ile Glu Tyr Ala Leu
            35                  40                  45

Lys Ala Gly Ala Lys Val Met Val Thr Ser His Leu Gly Arg Pro Glu
        50                  55                  60

Glu Gly Val Tyr Ser Glu Glu Asn Ser Leu Arg Pro Val Ala Asp Val
65                  70                  75                  80

Met Ser Lys Leu Leu Gly Gln Pro Val Arg Leu Val Lys Asn Trp Leu
                85                  90                  95
```

```
Ala Pro Asn Ala Pro Glu Asp Ser Leu Thr Thr Ala Asp Gly Gln Leu
        100                 105                 110

Ile Leu Leu Glu Asn Cys Arg Phe Asn Val Gly Glu Lys Lys Asn Asn
            115                 120                 125

Asp Asp Leu Ala Lys Lys Tyr Ala Ala Leu Cys Asp Val Phe Val Met
        130                 135                 140

Asp Ala Phe Gly Thr Ala His Arg Ala Glu Ala Ser Thr His Gly Ile
145                 150                 155                 160

Ala Lys Phe Ala Pro Val Ala Cys Ala Gly Ile Leu Leu Thr Glu Glu
                165                 170                 175

Leu Asp Ala Leu Ser Lys Ala Leu Leu Ala Pro Ala Arg Pro Leu Val
            180                 185                 190

Ala Ile Val Gly Gly Ser Lys Val Ser Thr Lys Leu Thr Val Leu Glu
        195                 200                 205

Ser Leu Ser Asp Lys Val Asp Gln Leu Val Val Gly Gly Gly Ile Ala
        210                 215                 220

Asn Thr Phe Leu Lys Ala Ser Gly Gln Glu Val Gly Lys Ser Leu Cys
225                 230                 235                 240

Glu Asp Asp Leu Val Asp Thr Ala Lys Cys Leu Met Asp Lys Met Ala
                245                 250                 255

Ala Arg Gly Ala Cys Val Pro Ile Ala Lys Asp Val Val Gly Lys
            260                 265                 270

Gln Phe Asp Ala Asn Glu Pro Ala Val Lys Lys Ser Ala Thr Glu Val
        275                 280                 285

Ala Val Asp Glu Met Ile Phe Asp Ile Gly Ser Gln Ser Ala Ala Glu
        290                 295                 300

Leu Val Asp Ile Ile Met Lys Ala Gly Thr Val Val Trp Asn Gly Pro
305                 310                 315                 320

Val Gly Val Phe Glu Phe Asp Gln Phe Gly Glu Gly Thr Lys Thr Ile
                325                 330                 335

Ala Lys Ala Ile Ala Glu Thr Lys Ala Phe Thr Leu Ala Gly Gly Gly
            340                 345                 350

Asp Thr Ile Ala Ala Ile Gln Lys Tyr Asp Ile Tyr Asp Lys Val Ser
        355                 360                 365

Tyr Ile Ser Thr Ala Gly Gly Ala Phe Leu Glu Phe Leu Glu Gly Lys
        370                 375                 380

Thr Leu Pro Ala Val Ala Ile Leu Glu Glu Arg Ala Arg
385                 390                 395

<210> SEQ ID NO 35
<211> LENGTH: 1551
<212> TYPE: DNA
<213> ORGANISM: Methylophilus methylotrophus
<220> FEATURE:
<221> NAME/KEY: CDS
<222> LOCATION: (1)..(1551)
<223> OTHER INFORMATION:

<400> SEQUENCE: 35 atg cct atc aaa cct gtt att ttg ctg att ctc gat ggt ttt ggt cac     48
Met Pro Ile Lys Pro Val Ile Leu Leu Ile Leu Asp Gly Phe Gly His
1               5                   10                  15 agc gag acc gtt gaa ttc aat gcc gtc ctg caa gcg aac acc ccc aac     96
Ser Glu Thr Val Glu Phe Asn Ala Val Leu Gln Ala Asn Thr Pro Asn
                20                  25                  30 ctg gac aga ctt aga gcg acg tac ccg cat agc ttg atc aat gcc tct    144
Leu Asp Arg Leu Arg Ala Thr Tyr Pro His Ser Leu Ile Asn Ala Ser
```

-continued

|  | 35 |  |  |  | 40 |  |  |  | 45 |  |  |  |  |
|---|---|---|---|---|---|---|---|---|---|---|---|---|---|

| gaa | cac | tac | gtt | ggc | ctg | ccg | gac | gga | cag | atg | ggc | aac | tca | gaa | gtg | 192 |
| Glu | His | Tyr | Val | Gly | Leu | Pro | Asp | Gly | Gln | Met | Gly | Asn | Ser | Glu | Val |  |
|  | 50 |  |  |  | 55 |  |  |  | 60 |  |  |  |  |

| ggc | cac | ttg | aat | att | ggg | gcg | gga | cgt | atc | gtc | ttt | caa | gac | ttc | gag | 240 |
| Gly | His | Leu | Asn | Ile | Gly | Ala | Gly | Arg | Ile | Val | Phe | Gln | Asp | Phe | Glu |  |
| 65 |  |  |  |  | 70 |  |  |  | 75 |  |  |  |  | 80 |

| cgc | att | aat | aac | agc | ata | cac | acc | ggt | gag | ttt | ttc | cag | tta | ccc | gca | 288 |
| Arg | Ile | Asn | Asn | Ser | Ile | His | Thr | Gly | Glu | Phe | Phe | Gln | Leu | Pro | Ala |  |
|  |  |  |  | 85 |  |  |  |  | 90 |  |  |  |  | 95 |

| ctg | gtg | aat | gcc | atg | caa | gac | ctc | aaa | gcc | aac | gac | aaa | gcc | ctg | cac | 336 |
| Leu | Val | Asn | Ala | Met | Gln | Asp | Leu | Lys | Ala | Asn | Asp | Lys | Ala | Leu | His |  |
|  |  |  | 100 |  |  |  |  | 105 |  |  |  |  | 110 |

| atc | ctg | ggc | ctg | ctg | tct | gac | ggt | ggc | gta | cac | agc | tac | cag | cca | cac | 384 |
| Ile | Leu | Gly | Leu | Leu | Ser | Asp | Gly | Gly | Val | His | Ser | Tyr | Gln | Pro | His |  |
|  |  | 115 |  |  |  |  | 120 |  |  |  |  | 125 |

| att | cac | gcc | atg | ctc | gat | atg | gcc | aaa | cag | caa | ggc | ctg | aac | aaa | gtg | 432 |
| Ile | His | Ala | Met | Leu | Asp | Met | Ala | Lys | Gln | Gln | Gly | Leu | Asn | Lys | Val |  |
| 130 |  |  |  |  | 135 |  |  |  |  | 140 |

| tat | gtg | cat | gcc | ttc | cta | gat | ggc | cgt | gac | aca | ccg | cca | aag | agc | gcg | 480 |
| Tyr | Val | His | Ala | Phe | Leu | Asp | Gly | Arg | Asp | Thr | Pro | Pro | Lys | Ser | Ala |  |
| 145 |  |  |  |  | 150 |  |  |  |  | 155 |  |  |  |  | 160 |

| caa | cct | tac | ctg | caa | gca | ctc | gaa | gat | cac | ctg | aaa | acc | ctt | ggc | gta | 528 |
| Gln | Pro | Tyr | Leu | Gln | Ala | Leu | Glu | Asp | His | Leu | Lys | Thr | Leu | Gly | Val |  |
|  |  |  | 165 |  |  |  |  | 170 |  |  |  |  | 175 |

| ggc | aaa | gtg | gcc | tct | gtg | ggt | ggc | cgt | ttc | tat | ggc | atg | gac | agg | gac | 576 |
| Gly | Lys | Val | Ala | Ser | Val | Gly | Gly | Arg | Phe | Tyr | Gly | Met | Asp | Arg | Asp |  |
|  |  |  | 180 |  |  |  |  | 185 |  |  |  |  | 190 |

| aaa | cgc | tgg | gag | cgc | gtt | tcg | gtc | gcg | tat | gag | tta | ctg | gtc | aat | ggc | 624 |
| Lys | Arg | Trp | Glu | Arg | Val | Ser | Val | Ala | Tyr | Glu | Leu | Leu | Val | Asn | Gly |  |
|  |  | 195 |  |  |  |  | 200 |  |  |  |  | 205 |

| att | gca | gac | cat | gtt | gca | ccc | gat | agc | ctc | acc | gca | tta | cta | cag | gct | 672 |
| Ile | Ala | Asp | His | Val | Ala | Pro | Asp | Ser | Leu | Thr | Ala | Leu | Leu | Gln | Ala |  |
|  | 210 |  |  |  |  | 215 |  |  |  |  | 220 |

| tat | gcg | cgt | gat | gag | agt | gac | gag | ttt | gtc | aaa | tgc | acc | gcc | atc | cgc | 720 |
| Tyr | Ala | Arg | Asp | Glu | Ser | Asp | Glu | Phe | Val | Lys | Cys | Thr | Ala | Ile | Arg |  |
| 225 |  |  |  |  | 230 |  |  |  |  | 235 |  |  |  |  | 240 |

| gcc | gcc | aat | gac | gcc | ccg | atc | cgg | atg | gag | gac | ggt | gac | tgc | ctg | gtg | 768 |
| Ala | Ala | Asn | Asp | Ala | Pro | Ile | Arg | Met | Glu | Asp | Gly | Asp | Cys | Leu | Val |  |
|  |  |  | 245 |  |  |  |  | 250 |  |  |  |  | 255 |

| ttt | atg | aac | ttc | agg | agt | gat | cgc | gcc | cgc | caa | ttg | act | gac | gcc | ttg | 816 |
| Phe | Met | Asn | Phe | Arg | Ser | Asp | Arg | Ala | Arg | Gln | Leu | Thr | Asp | Ala | Leu |  |
|  |  |  | 260 |  |  |  |  | 265 |  |  |  |  | 270 |

| ctc | aac | cag | caa | ttt | acc | ggt | ttt | tcc | cgt | agc | cgc | atc | cct | cac | ttc | 864 |
| Leu | Asn | Gln | Gln | Phe | Thr | Gly | Phe | Ser | Arg | Ser | Arg | Ile | Pro | His | Phe |  |
|  |  | 275 |  |  |  |  | 280 |  |  |  |  | 285 |

| agt | cac | tac | ttt | acg | ctg | acc | cag | tat | gac | aaa | aac | cag | acg | ctg | gct | 912 |
| Ser | His | Tyr | Phe | Thr | Leu | Thr | Gln | Tyr | Asp | Lys | Asn | Gln | Thr | Leu | Ala |  |
|  | 290 |  |  |  |  | 295 |  |  |  |  | 300 |

| gaa | ccg | att | ttt | gcc | ccc | tac | acg | gtt | cct | aac | acg | ttt | ggt | gag | tac | 960 |
| Glu | Pro | Ile | Phe | Ala | Pro | Tyr | Thr | Val | Pro | Asn | Thr | Phe | Gly | Glu | Tyr |  |
| 305 |  |  |  |  | 310 |  |  |  |  | 315 |  |  |  |  | 320 |

| gtc | tcc | aag | ctt | ggc | ctc | aaa | caa | cta | cgt | atc | gcc | gag | acc | gag | aaa | 1008 |
| Val | Ser | Lys | Leu | Gly | Leu | Lys | Gln | Leu | Arg | Ile | Ala | Glu | Thr | Glu | Lys |  |
|  |  |  | 325 |  |  |  |  | 330 |  |  |  |  | 335 |

| tat | ccg | cac | gtg | aca | ttt | ttc | ttc | aat | ggc | ggt | gaa | gaa | acg | gta | ttt | 1056 |
| Tyr | Pro | His | Val | Thr | Phe | Phe | Phe | Asn | Gly | Gly | Glu | Glu | Thr | Val | Phe |  |
|  |  |  | 340 |  |  |  |  | 345 |  |  |  |  | 350 |

| gat | ggt | gaa | gac | cgt | atc | ctg | gtc | cct | tcg | cct | aaa | gtc | gcc | act | tac | 1104 |

-continued

```
Asp Gly Glu Asp Arg Ile Leu Val Pro Ser Pro Lys Val Ala Thr Tyr
            355                 360                 365 gac ttg caa cct gaa atg agc gca cct gaa gtc acc gac aaa ctg gtg      1152
Asp Leu Gln Pro Glu Met Ser Ala Pro Glu Val Thr Asp Lys Leu Val
    370                 375                 380 gcc gca att gag tct ggg caa tac cag gcg gtg ata tgc aac tat gcc      1200
Ala Ala Ile Glu Ser Gly Gln Tyr Gln Ala Val Ile Cys Asn Tyr Ala
385                 390                 395                 400 aat ggc gac atg gtc ggc cat acc ggc aac ctg cag gcg gcg att aaa      1248
Asn Gly Asp Met Val Gly His Thr Gly Asn Leu Gln Ala Ala Ile Lys
                405                 410                 415 gct gtg gaa aca ctg gat acc tgt att ggc cgt gtg gta gcc gct gcg      1296
Ala Val Glu Thr Leu Asp Thr Cys Ile Gly Arg Val Val Ala Ala Ala
            420                 425                 430 cag aaa atg ggt gca gaa gtg att att acc gca gac cac ggc aat gca      1344
Gln Lys Met Gly Ala Glu Val Ile Ile Thr Ala Asp His Gly Asn Ala
        435                 440                 445 gaa agc atg ttt gac cat gcc agc gat cag gca cac acg cag cac acc      1392
Glu Ser Met Phe Asp His Ala Ser Asp Gln Ala His Thr Gln His Thr
    450                 455                 460 acc aac ctg gtg ccg ttt att tat att ggc cgc cca ggg agc att gct      1440
Thr Asn Leu Val Pro Phe Ile Tyr Ile Gly Arg Pro Gly Ser Ile Ala
465                 470                 475                 480 gca ggt ggt gcg ctt tct gat att gcg ccg acg ttg ctg tca ctg atg      1488
Ala Gly Gly Ala Leu Ser Asp Ile Ala Pro Thr Leu Leu Ser Leu Met
                485                 490                 495 ggc att ccc caa cct tca gaa atg aca ggc aag aac ttg atc acc ctc      1536
Gly Ile Pro Gln Pro Ser Glu Met Thr Gly Lys Asn Leu Ile Thr Leu
            500                 505                 510 aat gca atg gct taa                                                   1551
Asn Ala Met Ala
        515
```

<210> SEQ ID NO 36
<211> LENGTH: 516
<212> TYPE: PRT
<213> ORGANISM: Methylophilus methylotrophus

<400> SEQUENCE: 36

```
Met Pro Ile Lys Pro Val Ile Leu Ile Leu Asp Gly Phe Gly His
1               5                   10                  15

Ser Glu Thr Val Glu Phe Asn Ala Val Leu Gln Ala Asn Thr Pro Asn
            20                  25                  30

Leu Asp Arg Leu Arg Ala Thr Tyr Pro His Ser Leu Ile Asn Ala Ser
        35                  40                  45

Glu His Tyr Val Gly Leu Pro Asp Gly Gln Met Gly Asn Ser Glu Val
    50                  55                  60

Gly His Leu Asn Ile Gly Ala Gly Arg Ile Val Phe Gln Asp Phe Glu
65                  70                  75                  80

Arg Ile Asn Asn Ser Ile His Thr Gly Glu Phe Phe Gln Leu Pro Ala
                85                  90                  95

Leu Val Asn Ala Met Gln Asp Leu Lys Ala Asn Asp Lys Ala Leu His
                100                 105                 110

Ile Leu Gly Leu Leu Ser Asp Gly Gly Val His Ser Tyr Gln Pro His
            115                 120                 125

Ile His Ala Met Leu Asp Met Ala Lys Gln Gln Gly Leu Asn Lys Val
        130                 135                 140

Tyr Val His Ala Phe Leu Asp Gly Arg Asp Thr Pro Pro Lys Ser Ala
```

```
                145                 150                 155                 160
Gln Pro Tyr Leu Gln Ala Leu Glu Asp His Leu Lys Thr Leu Gly Val
                    165                 170                 175
Gly Lys Val Ala Ser Val Gly Gly Arg Phe Tyr Gly Met Asp Arg Asp
                180                 185                 190
Lys Arg Trp Glu Arg Val Ser Val Ala Tyr Glu Leu Leu Val Asn Gly
            195                 200                 205
Ile Ala Asp His Val Ala Pro Asp Ser Leu Thr Ala Leu Leu Gln Ala
        210                 215                 220
Tyr Ala Arg Asp Glu Ser Asp Glu Phe Val Lys Cys Thr Ala Ile Arg
225                 230                 235                 240
Ala Ala Asn Asp Ala Pro Ile Arg Met Glu Asp Gly Asp Cys Leu Val
                245                 250                 255
Phe Met Asn Phe Arg Ser Asp Arg Ala Arg Gln Leu Thr Asp Ala Leu
                260                 265                 270
Leu Asn Gln Gln Phe Thr Gly Phe Ser Arg Ser Arg Ile Pro His Phe
            275                 280                 285
Ser His Tyr Phe Thr Leu Thr Gln Tyr Asp Lys Asn Gln Thr Leu Ala
        290                 295                 300
Glu Pro Ile Phe Ala Pro Tyr Thr Val Pro Asn Thr Phe Gly Glu Tyr
305                 310                 315                 320
Val Ser Lys Leu Gly Leu Lys Gln Leu Arg Ile Ala Glu Thr Glu Lys
                325                 330                 335
Tyr Pro His Val Thr Phe Phe Asn Gly Gly Glu Gly Thr Val Phe
                340                 345                 350
Asp Gly Glu Asp Arg Ile Leu Val Pro Ser Pro Lys Val Ala Thr Tyr
            355                 360                 365
Asp Leu Gln Pro Glu Met Ser Ala Pro Glu Val Thr Asp Lys Leu Val
        370                 375                 380
Ala Ala Ile Glu Ser Gly Gln Tyr Gln Ala Val Ile Cys Asn Tyr Ala
385                 390                 395                 400
Asn Gly Asp Met Val Gly His Thr Gly Asn Leu Gln Ala Ala Ile Lys
                405                 410                 415
Ala Val Glu Thr Leu Asp Thr Cys Ile Gly Arg Val Val Ala Ala Ala
                420                 425                 430
Gln Lys Met Gly Ala Glu Val Ile Ile Thr Ala Asp His Gly Asn Ala
            435                 440                 445
Glu Ser Met Phe Asp His Ala Ser Asp Gln Ala His Thr Gln His Thr
        450                 455                 460
Thr Asn Leu Val Pro Phe Ile Tyr Ile Gly Arg Pro Gly Ser Ile Ala
465                 470                 475                 480
Ala Gly Gly Ala Leu Ser Asp Ile Ala Pro Thr Leu Leu Ser Leu Met
                485                 490                 495
Gly Ile Pro Gln Pro Ser Glu Met Thr Gly Lys Asn Leu Ile Thr Leu
            500                 505                 510
Asn Ala Met Ala
            515

<210> SEQ ID NO 37
<211> LENGTH: 1287
<212> TYPE: DNA
<213> ORGANISM: Methylophilus methylotrophus
<220> FEATURE:
<221> NAME/KEY: CDS
<222> LOCATION: (1)..(1287)
```

<223> OTHER INFORMATION:

<400> SEQUENCE: 37

```
atg agc gct att gta gat att atc gcc cgc gaa att atg gat tca cgc      48
Met Ser Ala Ile Val Asp Ile Ile Ala Arg Glu Ile Met Asp Ser Arg
1               5                   10                  15 ggc aac ccg acg gtt gaa gtg gac gta ttg ctg gaa agc ggt gtg att      96
Gly Asn Pro Thr Val Glu Val Asp Val Leu Leu Glu Ser Gly Val Ile
                20                  25                  30 ggt cgt gcg gct gtg cct tct ggc gct tcc aca ggc act aaa gaa gcg     144
Gly Arg Ala Ala Val Pro Ser Gly Ala Ser Thr Gly Thr Lys Glu Ala
            35                  40                  45 gtt gaa ctg cgt gac ggc gat aaa agc cgt tat tta ggt aag ggt gta     192
Val Glu Leu Arg Asp Gly Asp Lys Ser Arg Tyr Leu Gly Lys Gly Val
        50                  55                  60 ttg aat gcg gtt gaa aac gtc aat act gaa atc act gaa gcg atc att     240
Leu Asn Ala Val Glu Asn Val Asn Thr Glu Ile Thr Glu Ala Ile Ile
65                  70                  75                  80 ggc cta gat gct gaa gag caa agt ttt att gat aaa acg ctg att gag     288
Gly Leu Asp Ala Glu Glu Gln Ser Phe Ile Asp Lys Thr Leu Ile Glu
                85                  90                  95 ctg gac ggc aca gaa aac aag gac cgc ctg ggc gcg aat gca ata ctt     336
Leu Asp Gly Thr Glu Asn Lys Asp Arg Leu Gly Ala Asn Ala Ile Leu
                100                 105                 110 ggc gtg tcc atg gct tgt gcc cgt gcc gca gct gaa gag agt ggc ctg     384
Gly Val Ser Met Ala Cys Ala Arg Ala Ala Ala Glu Glu Ser Gly Leu
            115                 120                 125 ccg ttg tat cgc tat ctg ggc ggt tcc gcg ttc atg cag ttg cct acg     432
Pro Leu Tyr Arg Tyr Leu Gly Gly Ser Ala Phe Met Gln Leu Pro Thr
        130                 135                 140 ccg atg atg aac atc atc aac ggt ggt gca cat gcg gac aac tcc gta     480
Pro Met Met Asn Ile Ile Asn Gly Gly Ala His Ala Asp Asn Ser Val
145                 150                 155                 160 gat att caa gag ttc atg att gtg cca gct ggt ttg cca act ttt cgt     528
Asp Ile Gln Glu Phe Met Ile Val Pro Ala Gly Leu Pro Thr Phe Arg
                165                 170                 175 gag gcc ctg cgc gca ggt gca gaa gtg ttc cat gcc ttg aag aaa acc     576
Glu Ala Leu Arg Ala Gly Ala Glu Val Phe His Ala Leu Lys Lys Thr
                180                 185                 190 ctg cat gcc aag ggc ttg gct act acc gta ggt gat gaa ggc ggt ttt     624
Leu His Ala Lys Gly Leu Ala Thr Thr Val Gly Asp Glu Gly Gly Phe
            195                 200                 205 gcg cct aac ctg cca tcc aat gaa tct gcc ctg caa ttg atc atg gaa     672
Ala Pro Asn Leu Pro Ser Asn Glu Ser Ala Leu Gln Leu Ile Met Glu
        210                 215                 220 tcg att gaa gct gcg ggt tat gag cca ggc aaa gac atc tac ctg ggc     720
Ser Ile Glu Ala Ala Gly Tyr Glu Pro Gly Lys Asp Ile Tyr Leu Gly
225                 230                 235                 240 ctg gat tgc gcc agt acc gag ttt tac aag gat ggt aaa tac cat ctg     768
Leu Asp Cys Ala Ser Thr Glu Phe Tyr Lys Asp Gly Lys Tyr His Leu
                245                 250                 255 gag tca gag ggt gca tcg ctg act tca caa cag ttt tca gat tac ctg     816
Glu Ser Glu Gly Ala Ser Leu Thr Ser Gln Gln Phe Ser Asp Tyr Leu
                260                 265                 270 gcg aca ttg gct gac aaa tac ccc atc att act att gaa gac ggg atg     864
Ala Thr Leu Ala Asp Lys Tyr Pro Ile Ile Thr Ile Glu Asp Gly Met
            275                 280                 285 agt gag ttt gac tgg gag ggc tgg gat atc ctg acc aaa cgc ctg ggt     912
Ser Glu Phe Asp Trp Glu Gly Trp Asp Ile Leu Thr Lys Arg Leu Gly
        290                 295                 300
```

```
aaa acc acg cag ctg gtg ggt gac gac ctg ttt gtg act aac cct aaa    960
Lys Thr Thr Gln Leu Val Gly Asp Asp Leu Phe Val Thr Asn Pro Lys
305                 310                 315                 320 atc ctg cgt gaa ggc atc cag aag ggc gct gcc aac tca gtg ctg atc   1008
Ile Leu Arg Glu Gly Ile Gln Lys Gly Ala Ala Asn Ser Val Leu Ile
                325                 330                 335 aag gtg aac cag att ggt acc ttg acc gaa acc ttc cag act atc gaa   1056
Lys Val Asn Gln Ile Gly Thr Leu Thr Glu Thr Phe Gln Thr Ile Glu
            340                 345                 350 atg gct aaa cgt gca aac tac acc gct gtc gtt tca cat cgt tct ggt   1104
Met Ala Lys Arg Ala Asn Tyr Thr Ala Val Val Ser His Arg Ser Gly
        355                 360                 365 gag act gaa gat aca acg att gct gat atc tct gtc gcc acc aac gcg   1152
Glu Thr Glu Asp Thr Thr Ile Ala Asp Ile Ser Val Ala Thr Asn Ala
370                 375                 380 ttg cag atc aag acc ggt tca ttg tgc cgt tcc gag cgc gta gcc aag   1200
Leu Gln Ile Lys Thr Gly Ser Leu Cys Arg Ser Glu Arg Val Ala Lys
385                 390                 395                 400 tac aac cag ttg ctg cgt att gaa gaa gaa ctg ggc gat gca acc agc   1248
Tyr Asn Gln Leu Leu Arg Ile Glu Glu Glu Leu Gly Asp Ala Thr Ser
                405                 410                 415 tat gct ggc ttg tct gct ttc tac cag tta ttc aag taa               1287
Tyr Ala Gly Leu Ser Ala Phe Tyr Gln Leu Phe Lys
            420                 425
```

<210> SEQ ID NO 38
<211> LENGTH: 428
<212> TYPE: PRT
<213> ORGANISM: Methylophilus methylotrophus

<400> SEQUENCE: 38

```
Met Ser Ala Ile Val Asp Ile Ile Ala Arg Glu Ile Met Asp Ser Arg
1               5                   10                  15

Gly Asn Pro Thr Val Glu Val Asp Val Leu Leu Glu Ser Gly Val Ile
            20                  25                  30

Gly Arg Ala Ala Val Pro Ser Gly Ala Ser Thr Gly Thr Lys Glu Ala
        35                  40                  45

Val Glu Leu Arg Asp Gly Asp Lys Ser Arg Tyr Leu Gly Lys Gly Val
    50                  55                  60

Leu Asn Ala Val Glu Asn Val Asn Thr Glu Ile Thr Glu Ala Ile Ile
65                  70                  75                  80

Gly Leu Asp Ala Glu Gln Ser Phe Ile Asp Lys Thr Leu Ile Glu
                85                  90                  95

Leu Asp Gly Thr Glu Asn Lys Asp Arg Leu Gly Ala Asn Ala Ile Leu
            100                 105                 110

Gly Val Ser Met Ala Cys Ala Arg Ala Ala Glu Glu Ser Gly Leu
        115                 120                 125

Pro Leu Tyr Arg Tyr Leu Gly Gly Ser Ala Phe Met Gln Leu Pro Thr
    130                 135                 140

Pro Met Met Asn Ile Ile Asn Gly Gly Ala His Ala Asp Asn Ser Val
145                 150                 155                 160

Asp Ile Gln Glu Phe Met Ile Val Pro Ala Gly Leu Pro Thr Phe Arg
                165                 170                 175

Glu Ala Leu Arg Ala Gly Ala Glu Val Phe His Ala Leu Lys Lys Thr
            180                 185                 190

Leu His Ala Lys Gly Leu Ala Thr Thr Val Gly Asp Glu Gly Gly Phe
        195                 200                 205
```

```
Ala Pro Asn Leu Pro Ser Asn Glu Ser Ala Leu Gln Leu Ile Met Glu
            210                 215                 220

Ser Ile Glu Ala Ala Gly Tyr Glu Pro Gly Lys Asp Ile Tyr Leu Gly
225                 230                 235                 240

Leu Asp Cys Ala Ser Thr Glu Phe Tyr Lys Asp Gly Lys Tyr His Leu
                245                 250                 255

Glu Ser Glu Gly Ala Ser Leu Thr Ser Gln Gln Phe Ser Asp Tyr Leu
            260                 265                 270

Ala Thr Leu Ala Asp Lys Tyr Pro Ile Ile Thr Ile Glu Asp Gly Met
        275                 280                 285

Ser Glu Phe Asp Trp Glu Gly Trp Asp Ile Leu Thr Lys Arg Leu Gly
    290                 295                 300

Lys Thr Thr Gln Leu Val Gly Asp Asp Leu Phe Val Thr Asn Pro Lys
305                 310                 315                 320

Ile Leu Arg Glu Gly Ile Gln Lys Gly Ala Ala Asn Ser Val Leu Ile
                325                 330                 335

Lys Val Asn Gln Ile Gly Thr Leu Thr Glu Thr Phe Gln Thr Ile Glu
            340                 345                 350

Met Ala Lys Arg Ala Asn Tyr Thr Ala Val Val Ser His Arg Ser Gly
        355                 360                 365

Glu Thr Glu Asp Thr Thr Ile Ala Asp Ile Ser Val Ala Thr Asn Ala
    370                 375                 380

Leu Gln Ile Lys Thr Gly Ser Leu Cys Arg Ser Glu Arg Val Ala Lys
385                 390                 395                 400

Tyr Asn Gln Leu Leu Arg Ile Glu Glu Glu Leu Gly Asp Ala Thr Ser
                405                 410                 415

Tyr Ala Gly Leu Ser Ala Phe Tyr Gln Leu Phe Lys
            420                 425

<210> SEQ ID NO 39
<211> LENGTH: 906
<212> TYPE: DNA
<213> ORGANISM: Methylophilus methylotrophus
<220> FEATURE:
<221> NAME/KEY: CDS
<222> LOCATION: (1)..(906)
<223> OTHER INFORMATION:

<400> SEQUENCE: 39 atg aaa tta gca atg att ggc ttg ggc aaa atg ggc ggc aac atg gct      48
Met Lys Leu Ala Met Ile Gly Leu Gly Lys Met Gly Gly Asn Met Ala
1               5                  10                  15 gca cgc ttg ctg cgt cac aaa atc aac gta gtt ggc ttt gac ttc aac      96
Ala Arg Leu Leu Arg His Lys Ile Asn Val Val Gly Phe Asp Phe Asn
            20                  25                  30 acc gaa ttc gtt aac aga ctg gtt aaa gaa gaa ggc atg gaa gcg gca     144
Thr Glu Phe Val Asn Arg Leu Val Lys Glu Glu Gly Met Glu Ala Ala
        35                  40                  45 acc tct gtg gcg gat gct gta agc aaa ctc gaa ggc caa aaa att gtc     192
Thr Ser Val Ala Asp Ala Val Ser Lys Leu Glu Gly Gln Lys Ile Val
    50                  55                  60 tgg ctg atg ttg cct gct ggc gaa atc acc gaa aat caa atc aaa gat     240
Trp Leu Met Leu Pro Ala Gly Glu Ile Thr Glu Asn Gln Ile Lys Asp
65                  70                  75                  80 ttg att cca atg ctg aac aaa ggc gac atc atc gtc gat ggc ggc aac     288
Leu Ile Pro Met Leu Asn Lys Gly Asp Ile Ile Val Asp Gly Gly Asn
                85                  90                  95
```

| | | |
|---|---|---|
| tct aac tac aaa cac agt cag cgt cgc ggt gca atg ttg gct gag cac<br>Ser Asn Tyr Lys His Ser Gln Arg Arg Gly Ala Met Leu Ala Glu His<br>　　　　　100　　　　　　　　　105　　　　　　　　　110 | | 336 |
| ggt atc ggc ttt atc gat tgc ggt act tct ggc ggt gtt tgg ggc ctt<br>Gly Ile Gly Phe Ile Asp Cys Gly Thr Ser Gly Gly Val Trp Gly Leu<br>　　　115　　　　　　　　　120　　　　　　　　　125 | | 384 |
| gaa aac ggc tac tgc ctg atg tac ggc ggt gaa aaa caa tat gca gat<br>Glu Asn Gly Tyr Cys Leu Met Tyr Gly Gly Glu Lys Gln Tyr Ala Asp<br>130　　　　　　　　　135　　　　　　　　　140 | | 432 |
| gta ttg gca cct tac gca cag gca ctg act cac gca gac cgt ggt tgg<br>Val Leu Ala Pro Tyr Ala Gln Ala Leu Thr His Ala Asp Arg Gly Trp<br>145　　　　　　　　　150　　　　　　　　　155　　　　　　　　　160 | | 480 |
| gca cac gtg ggt cca gtc ggc tcc ggc cac ttc aca aaa atg atc cat<br>Ala His Val Gly Pro Val Gly Ser Gly His Phe Thr Lys Met Ile His<br>　　　　　　　　　165　　　　　　　　　170　　　　　　　　　175 | | 528 |
| aac ggt atc gaa tac ggc atg atg caa gcg ttt gct gaa ggt ctg gac<br>Asn Gly Ile Glu Tyr Gly Met Met Gln Ala Phe Ala Glu Gly Leu Asp<br>　　　　　180　　　　　　　　　185　　　　　　　　　190 | | 576 |
| ctg atc aaa ggt aaa gaa gac ttc aac ctg gat ctg gca caa atc act<br>Leu Ile Lys Gly Lys Glu Asp Phe Asn Leu Asp Leu Ala Gln Ile Thr<br>　　　195　　　　　　　　　200　　　　　　　　　205 | | 624 |
| gaa ttg tgg cgt cat ggt tcc gtg gtt cgc agc tgg ttg ctg gat ctg<br>Glu Leu Trp Arg His Gly Ser Val Val Arg Ser Trp Leu Leu Asp Leu<br>210　　　　　　　　　215　　　　　　　　　220 | | 672 |
| act gct gaa gca ctg aaa ggt gac cag aag ctg gaa gcc atc gct cct<br>Thr Ala Glu Ala Leu Lys Gly Asp Gln Lys Leu Glu Ala Ile Ala Pro<br>225　　　　　　　　　230　　　　　　　　　235　　　　　　　　　240 | | 720 |
| tat gtt gct gac tcc ggc gaa ggc cgc tgg aca gtg gtt gaa gcg gtt<br>Tyr Val Ala Asp Ser Gly Glu Gly Arg Trp Thr Val Val Glu Ala Val<br>　　　　　　　　　245　　　　　　　　　250　　　　　　　　　255 | | 768 |
| gaa caa ggt gtt gct gcg cca gta ctg act gtt gca ttg caa gcc cgt<br>Glu Gln Gly Val Ala Ala Pro Val Leu Thr Val Ala Leu Gln Ala Arg<br>　　　　　260　　　　　　　　　265　　　　　　　　　270 | | 816 |
| ttc cgc agc cag gac tcc aaa ggt tac agc tac aaa ctg ttg tca ctg<br>Phe Arg Ser Gln Asp Ser Lys Gly Tyr Ser Tyr Lys Leu Leu Ser Leu<br>　　　275　　　　　　　　　280　　　　　　　　　285 | | 864 |
| atg cgt aat gca ttt ggt ggc cac gca gtt aaa acc aag taa<br>Met Arg Asn Ala Phe Gly Gly His Ala Val Lys Thr Lys<br>290　　　　　　　　　295　　　　　　　　　300 | | 906 |

<210> SEQ ID NO 40
<211> LENGTH: 301
<212> TYPE: PRT
<213> ORGANISM: Methylophilus methylotrophus

<400> SEQUENCE: 40

Met Lys Leu Ala Met Ile Gly Leu Gly Lys Met Gly Gly Asn Met Ala
1　　　　　　　　　5　　　　　　　　　　10　　　　　　　　　15

Ala Arg Leu Leu Arg His Lys Ile Asn Val Val Gly Phe Asp Phe Asn
　　　　　　　　　20　　　　　　　　　25　　　　　　　　　30

Thr Glu Phe Val Asn Arg Leu Val Lys Glu Glu Gly Met Glu Ala Ala
　　　　　35　　　　　　　　　40　　　　　　　　　45

Thr Ser Val Ala Asp Ala Val Ser Lys Leu Glu Gly Gln Lys Ile Val
　　　50　　　　　　　　　55　　　　　　　　　60

Trp Leu Met Leu Pro Ala Gly Glu Ile Thr Glu Asn Gln Ile Lys Asp
65　　　　　　　　　70　　　　　　　　　75　　　　　　　　　80

Leu Ile Pro Met Leu Asn Lys Gly Asp Ile Ile Val Asp Gly Gly Asn
　　　　　　　　　85　　　　　　　　　90　　　　　　　　　95

Ser Asn Tyr Lys His Ser Gln Arg Arg Gly Ala Met Leu Ala Glu His

```
                    100                 105                 110
            Gly Ile Gly Phe Ile Asp Cys Gly Thr Ser Gly Gly Val Trp Gly Leu
                    115                 120                 125

Glu Asn Gly Tyr Cys Leu Met Tyr Gly Gly Glu Lys Gln Tyr Ala Asp
                130                 135                 140

Val Leu Ala Pro Tyr Ala Gln Ala Leu Thr His Ala Asp Arg Gly Trp
            145                 150                 155                 160

Ala His Val Gly Pro Val Gly Ser Gly His Phe Thr Lys Met Ile His
                            165                 170                 175

Asn Gly Ile Glu Tyr Gly Met Met Gln Ala Phe Ala Glu Gly Leu Asp
                        180                 185                 190

Leu Ile Lys Gly Lys Glu Asp Phe Asn Leu Asp Leu Ala Gln Ile Thr
                    195                 200                 205

Glu Leu Trp Arg His Gly Ser Val Val Arg Ser Trp Leu Leu Asp Leu
                210                 215                 220

Thr Ala Glu Ala Leu Lys Gly Asp Gln Lys Leu Glu Ala Ile Ala Pro
            225                 230                 235                 240

Tyr Val Ala Asp Ser Gly Glu Gly Arg Trp Thr Val Val Glu Ala Val
                            245                 250                 255

Glu Gln Gly Val Ala Ala Pro Val Leu Thr Val Ala Leu Gln Ala Arg
                        260                 265                 270

Phe Arg Ser Gln Asp Ser Lys Gly Tyr Ser Tyr Lys Leu Leu Ser Leu
                    275                 280                 285

Met Arg Asn Ala Phe Gly Gly His Ala Val Lys Thr Lys
                290                 295                 300

<210> SEQ ID NO 41
<211> LENGTH: 1515
<212> TYPE: DNA
<213> ORGANISM: Methylophilus methylotrophus
<220> FEATURE:
<221> NAME/KEY: CDS
<222> LOCATION: (1)..(1515)
<223> OTHER INFORMATION:

<400> SEQUENCE: 41 atg act aca aaa aat gcg gat att gga ttg gta gga ttg gca gtg atg      48
Met Thr Thr Lys Asn Ala Asp Ile Gly Leu Val Gly Leu Ala Val Met
1               5                   10                  15 ggc caa aac ctg gcg ctt aac att gct gat cac ggc tat acc atc gcg      96
Gly Gln Asn Leu Ala Leu Asn Ile Ala Asp His Gly Tyr Thr Ile Ala
            20                  25                  30 gtc tat aac cgt gat ccg aaa aaa atg ctg aac ttc atc gag gag tgc     144
Val Tyr Asn Arg Asp Pro Lys Lys Met Leu Asn Phe Ile Glu Glu Cys
        35                  40                  45 aaa aag aac gag cct tcc cac gag cgt gtg gtg ggt cat gcc gat ctg     192
Lys Lys Asn Glu Pro Ser His Glu Arg Val Val Gly His Ala Asp Leu
    50                  55                  60 gcg tct ttt gta ttg agc atc aag cgt cct cgc aag att gtg ttg ctg     240
Ala Ser Phe Val Leu Ser Ile Lys Arg Pro Arg Lys Ile Val Leu Leu
65                  70                  75                  80 gta aaa gcc ggt agc gcg acc gat gtg acg att aac gcc ttg ctg cct     288
Val Lys Ala Gly Ser Ala Thr Asp Val Thr Ile Asn Ala Leu Leu Pro
                85                  90                  95 ttc ctg gag cag ggc gac att att att gat ggc ggt aat gcg ctg tgg     336
Phe Leu Glu Gln Gly Asp Ile Ile Ile Asp Gly Gly Asn Ala Leu Trp
            100                 105                 110 act gac acc atc cgc cgt gaa aaa gag ctg gcc gcc aaa ggc att gag     384
```

```
            Thr Asp Thr Ile Arg Arg Glu Lys Glu Leu Ala Ala Lys Gly Ile Glu
                    115                 120                 125 ttt att ggc tca ggt gtt tcc ggt ggc gaa acc ggt gcc cgt ttc ggc              432
Phe Ile Gly Ser Gly Val Ser Gly Gly Glu Thr Gly Ala Arg Phe Gly
130                 135                 140 cca tcg ctg atg cct tca ggc acg cgc aag gcc tgg gca agc ctg gag              480
Pro Ser Leu Met Pro Ser Gly Thr Arg Lys Ala Trp Ala Ser Leu Glu
145                 150                 155                 160 ccc atc tgg cgt gat att gct gcc aag gtc gat cct gtc acc ggt acg              528
Pro Ile Trp Arg Asp Ile Ala Ala Lys Val Asp Pro Val Thr Gly Thr
                    165                 170                 175 cca tta gaa ggc ggc gct ccc ggc aaa ccg gta gaa ggc ggc ttt tcc              576
Pro Leu Glu Gly Gly Ala Pro Gly Lys Pro Val Glu Gly Gly Phe Ser
                180                 185                 190 tgt gct gaa tat atc ggc ccg gat ggc gca ggt cac tat gtg aaa atg              624
Cys Ala Glu Tyr Ile Gly Pro Asp Gly Ala Gly His Tyr Val Lys Met
            195                 200                 205 gtg cac aac ggt atc gaa tac atc gat atg caa ttg atc tgc gaa gcc              672
Val His Asn Gly Ile Glu Tyr Ile Asp Met Gln Leu Ile Cys Glu Ala
        210                 215                 220 tac tgg ctc atg aaa aac ctg ctc ggc atg cca gca gac gaa att ggt              720
Tyr Trp Leu Met Lys Asn Leu Leu Gly Met Pro Ala Asp Glu Ile Gly
225                 230                 235                 240 aaa gta ttt gcc gag tgg aac aag ggc gag ctg tcc agc ttc ctg att              768
Lys Val Phe Ala Glu Trp Asn Lys Gly Glu Leu Ser Ser Phe Leu Ile
                    245                 250                 255 gaa atc acg gca gat atc ctg caa cag aaa gac cca tca ggc aaa ggt              816
Glu Ile Thr Ala Asp Ile Leu Gln Gln Lys Asp Pro Ser Gly Lys Gly
                260                 265                 270 ttc ctg gtc gac aat att ctg gat aca gca ggc cag aag ggt acc ggc              864
Phe Leu Val Asp Asn Ile Leu Asp Thr Ala Gly Gln Lys Gly Thr Gly
            275                 280                 285 cag tgg acg gcc gcc aac gcg ctt gaa ctg ggc gca cct gct aac gcg              912
Gln Trp Thr Ala Ala Asn Ala Leu Glu Leu Gly Ala Pro Ala Asn Ala
        290                 295                 300 att gca gcg gcg gtg tat gcg cgt gcc ttg tcc agc ttg aaa gag gag              960
Ile Ala Ala Ala Val Tyr Ala Arg Ala Leu Ser Ser Leu Lys Glu Glu
305                 310                 315                 320 cgt gta gaa gcg agc aag atc ctc aag ggg cca gcc att gtg caa gaa             1008
Arg Val Glu Ala Ser Lys Ile Leu Lys Gly Pro Ala Ile Val Gln Glu
                    325                 330                 335 aaa gac aag gca ggt att att gag gcg atc aga aat gct ttg tat tgc             1056
Lys Asp Lys Ala Gly Ile Ile Glu Ala Ile Arg Asn Ala Leu Tyr Cys
                340                 345                 350 tcc aaa atc tgc gct tac gca caa ggc ttc cag ctc atc gac aaa gcg             1104
Ser Lys Ile Cys Ala Tyr Ala Gln Gly Phe Gln Leu Ile Asp Lys Ala
            355                 360                 365 cag gtg gct tac aac tgg aaa ctc aac ttc ggt gag att gcc cag atc             1152
Gln Val Ala Tyr Asn Trp Lys Leu Asn Phe Gly Glu Ile Ala Gln Ile
        370                 375                 380 tgg cgt ggt ggt tgt atc atc cga gcc cgc ttc ctg caa aaa atc act             1200
Trp Arg Gly Gly Cys Ile Ile Arg Ala Arg Phe Leu Gln Lys Ile Thr
385                 390                 395                 400 gat gct tac gca ttg aac tca cgt ttg aaa aat ctg atg ctg gac cct             1248
Asp Ala Tyr Ala Leu Asn Ser Arg Leu Lys Asn Leu Met Leu Asp Pro
                    405                 410                 415 tat ttc aca aat gcc atg aac gaa ggt cag gct ggc tgg cgt aaa gtg             1296
Tyr Phe Thr Asn Ala Met Asn Glu Gly Gln Ala Gly Trp Arg Lys Val
                420                 425                 430
```

-continued

```
att gcg ctg gca gtg acc aat ggt atc ccc gcg caa ggt ttt gct gcg    1344
Ile Ala Leu Ala Val Thr Asn Gly Ile Pro Ala Gln Gly Phe Ala Ala
        435                 440                 445 gcg ctg gct tac tac gat ggt tac aga agc gct gat ttg cca gct aac    1392
Ala Leu Ala Tyr Tyr Asp Gly Tyr Arg Ser Ala Asp Leu Pro Ala Asn
450                 455                 460 tta ctg caa ggc cag cgt gac tac ttt ggc gca cat act tat gag cgt    1440
Leu Leu Gln Gly Gln Arg Asp Tyr Phe Gly Ala His Thr Tyr Glu Arg
465                 470                 475                 480 aaa gac cag cca cgt ggc cag ttc ttc cac ctc gat tgg cca gaa gca    1488
Lys Asp Gln Pro Arg Gly Gln Phe Phe His Leu Asp Trp Pro Glu Ala
            485                 490                 495 ggt cgt ccg caa ttg acg att gaa tag                                1515
Gly Arg Pro Gln Leu Thr Ile Glu
            500
```

<210> SEQ ID NO 42
<211> LENGTH: 504
<212> TYPE: PRT
<213> ORGANISM: Methylophilus methylotrophus

<400> SEQUENCE: 42

```
Met Thr Thr Lys Asn Ala Asp Ile Gly Leu Val Gly Leu Ala Val Met
1               5                   10                  15

Gly Gln Asn Leu Ala Leu Asn Ile Ala Asp His Gly Tyr Thr Ile Ala
            20                  25                  30

Val Tyr Asn Arg Asp Pro Lys Lys Met Leu Asn Phe Ile Glu Glu Cys
        35                  40                  45

Lys Lys Asn Glu Pro Ser His Glu Arg Val Val Gly His Ala Asp Leu
    50                  55                  60

Ala Ser Phe Val Leu Ser Ile Lys Arg Pro Arg Lys Ile Val Leu Leu
65                  70                  75                  80

Val Lys Ala Gly Ser Ala Thr Asp Val Thr Ile Asn Ala Leu Leu Pro
                85                  90                  95

Phe Leu Glu Gln Gly Asp Ile Ile Ile Asp Gly Gly Asn Ala Leu Trp
            100                 105                 110

Thr Asp Thr Ile Arg Arg Glu Lys Glu Leu Ala Ala Lys Gly Ile Glu
        115                 120                 125

Phe Ile Gly Ser Gly Val Ser Gly Gly Glu Thr Gly Ala Arg Phe Gly
    130                 135                 140

Pro Ser Leu Met Pro Ser Gly Thr Arg Lys Ala Trp Ala Ser Leu Glu
145                 150                 155                 160

Pro Ile Trp Arg Asp Ile Ala Ala Lys Val Asp Pro Val Thr Gly Thr
                165                 170                 175

Pro Leu Glu Gly Gly Ala Pro Gly Lys Pro Val Glu Gly Gly Phe Ser
            180                 185                 190

Cys Ala Glu Tyr Ile Gly Pro Asp Gly Ala Gly His Tyr Val Lys Met
        195                 200                 205

Val His Asn Gly Ile Glu Tyr Ile Asp Met Gln Leu Ile Cys Glu Ala
    210                 215                 220

Tyr Trp Leu Met Lys Asn Leu Leu Gly Met Pro Ala Asp Glu Ile Gly
225                 230                 235                 240

Lys Val Phe Ala Glu Trp Asn Lys Gly Glu Leu Ser Ser Phe Leu Ile
                245                 250                 255

Glu Ile Thr Ala Asp Ile Leu Gln Gln Lys Asp Pro Ser Gly Lys Gly
            260                 265                 270
```

-continued

```
Phe Leu Val Asp Asn Ile Leu Asp Thr Ala Gly Gln Lys Gly Thr Gly
            275                 280                 285

Gln Trp Thr Ala Ala Asn Ala Leu Glu Leu Gly Ala Pro Ala Asn Ala
        290                 295                 300

Ile Ala Ala Ala Val Tyr Ala Arg Ala Leu Ser Ser Leu Lys Glu Glu
305                 310                 315                 320

Arg Val Glu Ala Ser Lys Ile Leu Lys Gly Pro Ala Ile Val Gln Glu
                325                 330                 335

Lys Asp Lys Ala Gly Ile Ile Glu Ala Ile Arg Asn Ala Leu Tyr Cys
                340                 345                 350

Ser Lys Ile Cys Ala Tyr Ala Gln Gly Phe Gln Leu Ile Asp Lys Ala
            355                 360                 365

Gln Val Ala Tyr Asn Trp Lys Leu Asn Phe Gly Glu Ile Ala Gln Ile
            370                 375                 380

Trp Arg Gly Gly Cys Ile Ile Arg Ala Arg Phe Leu Gln Lys Ile Thr
385                 390                 395                 400

Asp Ala Tyr Ala Leu Asn Ser Arg Leu Lys Asn Leu Met Leu Asp Pro
                405                 410                 415

Tyr Phe Thr Asn Ala Met Asn Glu Gly Gln Ala Gly Trp Arg Lys Val
                420                 425                 430

Ile Ala Leu Ala Val Thr Asn Gly Ile Pro Ala Gln Gly Phe Ala Ala
            435                 440                 445

Ala Leu Ala Tyr Tyr Asp Gly Tyr Arg Ser Ala Asp Leu Pro Ala Asn
    450                 455                 460

Leu Leu Gln Gly Gln Arg Asp Tyr Phe Gly Ala His Thr Tyr Glu Arg
465                 470                 475                 480

Lys Asp Gln Pro Arg Gly Gln Phe Phe His Leu Asp Trp Pro Glu Ala
                485                 490                 495

Gly Arg Pro Gln Leu Thr Ile Glu
                500
```